US011858963B2

(12) United States Patent
Hernandez et al.

(10) Patent No.: US 11,858,963 B2
(45) Date of Patent: *Jan. 2, 2024

(54) PCV2 ORF2 PROTEIN VARIANT AND VIRUS LIKE PARTICLES COMPOSED THEREOF

(71) Applicant: Boehringer Ingelheim Animal Health USA Inc., Duluth, GA (US)

(72) Inventors: Luis Alejandro Hernandez, Story City, IA (US); Christine Margaret Muehlenthaler, Ames, IA (US); Eric Martin Vaughn, Ames, IA (US); Gregory Haiwick, Ankeny, IA (US)

(*) Notice: Subject to any disclaimer, the term of this patent is extended or adjusted under 35 U.S.C. 154(b) by 262 days.

This patent is subject to a terminal disclaimer.

(21) Appl. No.: 17/215,636

(22) Filed: Mar. 29, 2021

(65) Prior Publication Data

US 2021/0221852 A1     Jul. 22, 2021

Related U.S. Application Data

(63) Continuation of application No. 16/154,294, filed on Oct. 8, 2018, now Pat. No. 10,961,281, which is a
(Continued)

(51) Int. Cl.
*C07K 14/005*     (2006.01)
*C12N 7/00*     (2006.01)
(Continued)

(52) U.S. Cl.
CPC ............ *C07K 14/005* (2013.01); *A61K 39/12* (2013.01); *C12N 7/00* (2013.01); *C12P 21/02* (2013.01);
(Continued)

(58) Field of Classification Search
None
See application file for complete search history.

(56) References Cited

U.S. PATENT DOCUMENTS 2,909,462 A    10/1959   Warfield et al.
5,026,543 A     6/1991   Rijke
(Continued)

FOREIGN PATENT DOCUMENTS

CA     2264953 A1    2/1998
CA     2305623 A1    4/1999
(Continued)

OTHER PUBLICATIONS

Davies et al. (Virus Research. 2016; 217: 32-37)).*
(Continued)

*Primary Examiner* — Shanon A. Foley
(74) *Attorney, Agent, or Firm* — Suzanne Seavello Shope

(57) ABSTRACT

Vaccination methods to control PCV2 infection with different PCV2 subtypes are disclosed. Specifically, a PCV2 subtype b (PCV2b) ORF2 proteins or immunogenic compositions comprising a PCV2b ORF2 protein are used in a method for the treatment or prevention of an infection with PCV2 of the same PCV2b and/or different subtype; the reduction, prevention or treatment of clinical signs caused by an infection with PCV2 of the same PCV2b or a different subtype; and/or the prevention or treatment of a disease caused by an infection with PCV2 of the same PCV2b and/or a different subtype. The present invention in particular relates to PCV2 subtype b (PCV2b) ORF2 proteins characterized in that they contain at least one mutation in the BC loop that such that the expressed protein is preferably expressed in a higher amount compared to a PCV2 ORF2 protein that does not contain such mutation.

43 Claims, 8 Drawing Sheets

Specification includes a Sequence Listing.

Related U.S. Application Data continuation of application No. 15/295,053, filed on Oct. 17, 2016, now Pat. No. 10,131,696, which is a continuation of application No. 14/504,839, filed on Oct. 2, 2014, now Pat. No. 9,505,808.

(60) Provisional application No. 61/885,871, filed on Oct. 2, 2013.

(51) Int. Cl.
*A61K 39/12* (2006.01)
*C12P 21/02* (2006.01)
*A61K 39/00* (2006.01)

(52) U.S. Cl.
CPC ...... *A61K 39/00* (2013.01); *A61K 2039/5256* (2013.01); *A61K 2039/5258* (2013.01); *A61K 2039/53* (2013.01); *C12N 2710/14043* (2013.01); *C12N 2750/10022* (2013.01); *C12N 2750/10023* (2013.01); *C12N 2750/10034* (2013.01); *C12N 2750/10051* (2013.01); *C12N 2799/026* (2013.01)

(56) References Cited

U.S. PATENT DOCUMENTS

| | | |
|---|---|---|
| 5,155,037 A | 10/1992 | Summers |
| 5,202,430 A | 4/1993 | Brian et al. |
| 5,322,774 A | 6/1994 | Peakman et al. |
| 5,436,001 A | 7/1995 | Kramer |
| 5,476,778 A | 12/1995 | Chladek et al. |
| 5,565,205 A | 10/1996 | Petersen et al. |
| 5,580,557 A | 12/1996 | Kramer |
| 5,733,555 A | 3/1998 | Chu |
| 5,885,823 A | 3/1999 | Knittel et al. |
| 5,925,359 A | 7/1999 | Van Woensel et al. |
| 5,968,525 A | 10/1999 | Fitzgerald et al. |
| 6,217,883 B1 | 4/2001 | Allan et al. |
| 6,287,856 B1 | 9/2001 | Poet et al. |
| 6,294,176 B1 | 9/2001 | Cochran et al. |
| 6,368,601 B1 | 4/2002 | Allan et al. |
| 6,391,314 B1 | 5/2002 | Allan et al. |
| 6,497,883 B1 | 12/2002 | Bublot et al. |
| 6,517,843 B1 | 2/2003 | Ellis et al. |
| 6,660,272 B2 | 12/2003 | Allan et al. |
| 6,703,023 B1 | 3/2004 | Jestin et al. |
| 6,794,163 B2 | 9/2004 | Liu et al. |
| 6,808,900 B2 | 10/2004 | Simonsen |
| 6,841,364 B2 | 1/2005 | Yuan et al. |
| 6,846,477 B2 | 1/2005 | Keich et al. |
| 6,943,152 B1 | 9/2005 | Audonnet et al. |
| 6,953,581 B2 | 10/2005 | Allan et al. |
| 7,018,638 B2 | 3/2006 | Chu et al. |
| 7,109,025 B1 | 9/2006 | Eloit et al. |
| 7,122,192 B2 | 10/2006 | Allan et al. |
| 7,144,698 B2 | 12/2006 | Wang et al. |
| 7,148,015 B2 | 12/2006 | Jestin et al. |
| 7,169,394 B2 | 1/2007 | Chu et al. |
| 7,172,899 B2 | 2/2007 | Liu et al. |
| 7,179,472 B2 | 2/2007 | Jestin et al. |
| 7,192,594 B2 | 3/2007 | Haines et al. |
| 7,211,379 B2 | 5/2007 | Ellis et al. |
| 7,223,407 B2 | 5/2007 | Jestin et al. |
| 7,223,594 B2 | 5/2007 | Jestin et al. |
| 7,244,433 B2 | 7/2007 | Jestin et al. |
| 7,258,865 B2 | 8/2007 | Jestin et al. |
| 7,261,898 B2 | 8/2007 | Jestin et al. |
| 7,273,617 B2 | 9/2007 | Yuan et al. |
| 7,276,353 B2 | 10/2007 | Meng et al. |
| 7,279,166 B2 | 10/2007 | Meng et al. |
| 7,297,537 B2 | 11/2007 | Jestin et al. |
| 7,300,785 B2 | 11/2007 | Meerts et al. |
| 7,312,065 B2 | 12/2007 | Roof et al. |
| 7,314,628 B2 | 1/2008 | Jestin et al. |
| 7,323,330 B2 | 1/2008 | Jestin et al. |
| 7,335,361 B2 | 2/2008 | Liao et al. |
| 7,358,075 B2 | 4/2008 | Allibert et al. |
| 7,368,117 B2 | 5/2008 | Fetzer et al. |
| 7,371,395 B2 | 5/2008 | Parisot et al. |
| 7,390,494 B2 | 6/2008 | Jestin et al. |
| 7,405,075 B2 | 7/2008 | Jestin et al. |
| 7,407,803 B2 | 8/2008 | Jestin et al. |
| 7,425,444 B2 | 9/2008 | Jestin et al. |
| 7,700,285 B1 | 4/2010 | Eichmeyer et al. |
| 7,758,865 B2 | 7/2010 | Jestin et al. |
| 7,829,101 B2 | 11/2010 | Eichmeyer et al. |
| 7,829,273 B2 | 11/2010 | Roof et al. |
| 7,829,274 B2 | 11/2010 | Fachinger et al. |
| 7,833,707 B2 | 11/2010 | Eichmeyer et al. |
| 7,838,213 B2 | 11/2010 | Roof et al. |
| 7,838,214 B2 | 11/2010 | Roof et al. |
| 7,910,306 B2 | 3/2011 | Eichmeyer et al. |
| 7,914,992 B2 | 3/2011 | Fachinger et al. |
| 7,943,298 B2 | 5/2011 | Fachinger et al. |
| 7,951,907 B2 | 5/2011 | Jestin et al. |
| 7,968,285 B2 | 6/2011 | Roof et al. |
| 8,025,888 B2 | 9/2011 | Eichmeyer et al. |
| 8,119,143 B2 | 2/2012 | Roof et al. |
| 8,475,805 B2 | 7/2013 | Fachinger et al. |
| 8,496,940 B2 | 7/2013 | Fachinger et al. |
| 8,852,613 B2 | 10/2014 | Ohnesorge et al. |
| 8,865,183 B2 | 10/2014 | Fachinger et al. |
| 9,011,868 B2 | 4/2015 | Roof et al. |
| 9,011,872 B2 | 4/2015 | Eichmeyer et al. |
| 9,132,187 B2 | 9/2015 | Fachinger et al. |
| 9,505,808 B2 * | 11/2016 | Hernandez ............... C12N 7/00 |
| 9,517,260 B2 | 12/2016 | Fachinger et al. |
| 9,522,182 B2 | 12/2016 | Fachinger et al. |
| 9,555,092 B2 | 1/2017 | Fachinger et al. |
| 9,669,087 B2 | 6/2017 | Roof et al. |
| 10,131,696 B2 * | 11/2018 | Hernandez ............. A61K 39/12 |
| 10,555,994 B2 | 2/2020 | Hernandez et al. |
| 10,961,281 B2 * | 3/2021 | Hernandez ............... C12N 7/00 |
| 2002/0146431 A1 | 10/2002 | Allan et al. |
| 2003/0096377 A1 | 5/2003 | Meng et al. |
| 2003/0170270 A1 | 9/2003 | Meng et al. |
| 2003/0199581 A1 | 10/2003 | Seligson et al. |
| 2003/0215455 A1 | 11/2003 | Reynolds et al. |
| 2004/0062775 A1 | 4/2004 | Jestin et al. |
| 2004/0076635 A1 | 4/2004 | Jestin et al. |
| 2004/0091502 A1 | 5/2004 | Jestin et al. |
| 2004/0132178 A1 | 7/2004 | Haines et al. |
| 2004/0161410 A1 | 8/2004 | Jestin et al. |
| 2004/0208901 A1 | 10/2004 | Ellsworth et al. |
| 2004/0253270 A1 | 12/2004 | Meng et al. |
| 2004/0258715 A1 | 12/2004 | Allan et al. |
| 2004/0265848 A1 | 12/2004 | Jestin et al. |
| 2005/0008651 A1 | 1/2005 | Jestin et al. |
| 2005/0013823 A1 | 1/2005 | Keich et al. |
| 2005/0031647 A1 | 2/2005 | Roof et al. |
| 2005/0058653 A1 | 3/2005 | Ellis et al. |
| 2005/0079185 A1 | 4/2005 | Parisot et al. |
| 2005/0084497 A1 | 4/2005 | Jestin et al. |
| 2005/0147966 A1 | 7/2005 | Meng et al. |
| 2005/0238662 A1 | 10/2005 | Jestin et al. |
| 2006/0002952 A1 | 1/2006 | Haines et al. |
| 2006/0029617 A1 | 2/2006 | Charreyre et al. |
| 2006/0083756 A1 | 4/2006 | Jestin et al. |
| 2006/0115489 A1 | 6/2006 | Birkett et al. |
| 2006/0204522 A1 | 9/2006 | Kroll et al. |
| 2006/0222659 A1 | 10/2006 | Jestin et al. |
| 2006/0228373 A1 | 10/2006 | Chu et al. |
| 2006/0233831 A1 | 10/2006 | Parisot et al. |
| 2006/0246425 A1 | 11/2006 | Allibert et al. |
| 2006/0286123 A1 | 12/2006 | Fetzer et al. |
| 2007/0196879 A1 | 8/2007 | Chabriere et al. |
| 2008/0181910 A1 | 7/2008 | Roof et al. |
| 2008/0226669 A1 | 9/2008 | Roof et al. |
| 2008/0233147 A1 | 9/2008 | Jestin et al. |
| 2008/0261887 A1 | 10/2008 | Roof et al. |
| 2008/0267995 A1 | 10/2008 | Roof et al. |
| 2008/0279875 A1 | 11/2008 | Roof et al. |
| 2008/0279876 A1 | 11/2008 | Roof et al. |

(56) References Cited

U.S. PATENT DOCUMENTS

| | | |
|---|---|---|
| 2008/0279889 A1 | 11/2008 | Roof et al. |
| 2009/0016992 A1 | 1/2009 | Eichmeyer et al. |
| 2009/0017064 A1 | 1/2009 | Wu et al. |
| 2009/0022751 A1 | 1/2009 | Eichmeyer et al. |
| 2009/0042245 A1 | 2/2009 | Eichmeyer et al. |
| 2010/0136060 A1 | 6/2010 | Kolb |
| 2010/0184016 A1 | 7/2010 | Lefebvre et al. |
| 2010/0189743 A1 | 7/2010 | Jestin et al. |
| 2011/0033495 A1 | 2/2011 | Roof et al. |
| 2011/0059126 A1 | 3/2011 | Kohler et al. |
| 2011/0091499 A1 | 4/2011 | Fachinger et al. |
| 2011/0217327 A1 | 9/2011 | Roof et al. |
| 2011/0274710 A1 | 11/2011 | Eichmeyer et al. |
| 2011/0305725 A1 | 12/2011 | Wu |
| 2013/0030320 A1 | 1/2013 | Maier |
| 2013/0115236 A1 | 5/2013 | Fachinger et al. |
| 2013/0230558 A1 | 9/2013 | Ohnesorge et al. |
| 2013/0273099 A1 | 10/2013 | Fachinger et al. |
| 2013/0302370 A1 | 11/2013 | Fachinger et al. |
| 2014/0322267 A1 | 10/2014 | Haiwick et al. |
| 2014/0377298 A1 | 12/2014 | Fachinger et al. |
| 2015/0093404 A1 | 4/2015 | Hernandez et al. |
| 2015/0174233 A1 | 6/2015 | Roof et al. |
| 2019/0023747 A1 | 1/2019 | Hernandez et al. |
| 2021/0221852 A1* | 7/2021 | Hernandez ............... C12N 7/00 |

FOREIGN PATENT DOCUMENTS

| | | |
|---|---|---|
| CN | 1579553 A | 7/1920 |
| CN | 1458167 A | 11/2003 |
| CN | 103122352 A | 5/2013 |
| EP | 1050584 A1 | 11/2000 |
| EP | 1073676 A1 | 2/2001 |
| EP | 1281760 A1 | 2/2003 |
| EP | 1386617 A1 | 2/2004 |
| EP | 3052516 B1 | 1/2020 |
| JP | 2002247979 A | 9/2002 |
| JP | 2005511075 A | 4/2005 |
| WO | 1989006972 A1 | 8/1989 |
| WO | 1990007935 A1 | 7/1990 |
| WO | 1991018627 A1 | 12/1991 |
| WO | 1992003157 A1 | 3/1992 |
| WO | 1993016726 A2 | 9/1993 |
| WO | 1996036356 A1 | 11/1996 |
| WO | 1999018214 A1 | 4/1999 |
| WO | 1999029717 A3 | 6/1999 |
| WO | 1999029871 A3 | 6/1999 |
| WO | 1999057141 A1 | 11/1999 |
| WO | 2000001409 A2 | 1/2000 |
| WO | 2000047756 A1 | 8/2000 |
| WO | 2000077188 A2 | 12/2000 |
| WO | 2000077216 A2 | 12/2000 |
| WO | 2001016330 A2 | 3/2001 |
| WO | 2001017556 A1 | 3/2001 |
| WO | 2001034191 A1 | 5/2001 |
| WO | 2001045735 A2 | 6/2001 |
| WO | 2001096377 A2 | 12/2001 |
| WO | 2002049666 A2 | 6/2002 |
| WO | 2002077210 A2 | 10/2002 |
| WO | 2003003941 A2 | 1/2003 |
| WO | 2003049703 A2 | 6/2003 |
| WO | 2003068993 A1 | 8/2003 |
| WO | 2004026336 A1 | 4/2004 |
| WO | 2004058142 A2 | 7/2004 |
| WO | 2004069184 A2 | 8/2004 |
| WO | 2005009462 A2 | 2/2005 |
| WO | 2005092069 A2 | 10/2005 |
| WO | 2005112995 A1 | 12/2005 |
| WO | 2006068663 A2 | 6/2006 |
| WO | 2006072065 A2 | 7/2006 |
| WO | 2006113372 A2 | 10/2006 |
| WO | 2006113373 A2 | 10/2006 |
| WO | 2007028823 A1 | 3/2007 |
| WO | 2007076520 A2 | 7/2007 |
| WO | 2007094893 A2 | 8/2007 |
| WO | 2008073464 A2 | 6/2008 |
| WO | 2008076915 A2 | 6/2008 |
| WO | 2008081015 A1 | 7/2008 |
| WO | 2008098909 A1 | 8/2008 |
| WO | 2009030684 A2 | 3/2009 |
| WO | 2009103037 A1 | 8/2009 |
| WO | 2011116094 A2 | 9/2011 |
| WO | 2012005732 A1 | 1/2012 |
| WO | 2012033911 A2 | 3/2012 |
| WO | 2014134561 A2 | 9/2014 |
| WO | 2014179200 A1 | 11/2014 |
| WO | 2015051099 A1 | 4/2015 |
| WO | 2015169732 A1 | 11/2015 |
| WO | 2016160761 A2 | 10/2016 |

OTHER PUBLICATIONS

Seq ID 3 alignment with Geneseq db access No. AEI93481 in WO2006072065 Sep. 2006 by Eichmeyer et al.*
GenBank accession No. AEN84893.2, Apr. 17, 2012, Cadar, D et al.
Kapust et al., "*Escherichia coli* maltose-binding protein is uncommonly effective at promoting the solubility of polypeptides to which it is fused". Protein Science, vol. 8, 1999, pp. 1668-1674.
Kennedy et al., "Reproduction of Lesions of Postweaning Multisystemic Wasting Syndrome by Infection of Conventional Pigs with Porcine Circovirus Type 2 Alone or in a Combination with Porcine Parvovirus". Journal of Comparative Pathology, vol. 122, 2000, pp. 9-24.
Kim et al., "A comparison of the Lymphocyte Subpopulations of Pigs Experimentally Infected with Porcine Circovirus 2 and/or Parvovirus". 2003, The Veterinary Journal, vol. 165, pp. 325-329.
Kim et al., "Association of Porcine Circovirus 2 with Porcine Respiratory Disese Complex", The Vet. Jour., 2003, 166, pp. 251-256.
Kim et al., "Characterization of the Recombinant Proteins of Porcine Circovirus Type2 Field Isolate Expressed in the Baculovirus System". 2002, Journal of Veterinary Science, vol. 3, No. 1, pp. 19-23.
Kim et al., "Efficacy of different disinfectants in vitro against porcine circovirus type 2". The Veterinary Record, vol. 164, May 2009, pp. 599-600.
Kim et al., "Enteritis associated with procine circovirus 2 in pigs". 2004, The Canadian Journal of Veterinary Research, vol. 68, pp. 218-221.
King et al., "Insect cell culture media and maintenance of insect cell lines." The Baculovirus Expression System: A laboratory guide, First Edition, Springer-Science + Business Media, B.V., 1992, pp. 75-79.
Kiupel, M. "Postweaning Multisystemic Wasting Syndrome (PMWS) in pigs". Production diseases in Farm Animals, 12th International Conference, Section D, Wageningen Academic Publishers, The Netherlands, 2006, pp. 74-89.
Kixmoller et al., "Reduction of PMWS-associated clinical signs and co-infections by vaccination against PCV2". 2008, Vaccine, vol. 26, pp. 3443-3451.
Knudsen et al., "Child Mortality Following Standard, Medium or High Titre Measles Immunization in West Africa." International Journal of Epidemiology, vol. 25, No. 3, 1996, pp. 665-673.
Kost, et al., "Recombinant baculoviruses as mammalian cell gene-delivery vectors". Apr. 2002, Trends in Biotechnology, vol. 20, No. 4, pp. 173-180.
Kovacs et al., "The live attenuated bovine viral diarrhea virus components of a multi-valent vaccine confer protection against fetal infection". Veterinary Microbiology, vol. 96, 2003, pp. 117-131.
Krakowka et al., "Activation of the Immune System is the Pivotal Event in the Production of Wasting Disease in Pigs Infected with Porcine Circovirus-2 (PCV-2)" Veterinary Pathology, vol. 38, 2001, pp. 31-42.
Krakowka et al., "Features of porcine circovirus-2 disease: correlations between lesions, amount and distribution of virus, and clinical outcome". Journal of Veterinary Diagnostic Investigation, vol. 17, No. 3, May 2005, pp. 213-222.
Krakowka et al., "Viral Wasting Sydrome of Swine: Experimental Reproduction of Postweaning Multisystemic Wasting Syndrome in

(56) References Cited

OTHER PUBLICATIONS

Gnotobiotic Swine by Coinfection with Porcine Circovirus 2 and Porcine Parvovirus." Veterinary Pathology, vol. 37, 2000, pp. 254-263.

Kyriakis et al., "The Effects of Immuno-modulation of the Clinical and Pathological Expression of Postweaning Multisystemic Wasting Syndrome". 2002, Journal of Comparative Pathology, vol. 126, pp. 38-46.

Kyriazakis et al., "The Maintenance of Health". Whittemore's Science and Practice of Pig Production, Third Edition, Chapter 7, Blackwell Publishing Ltd., Oxford, UK, 2006, pp. 263-316.

Ladekjaer-Mikkelsen et al., "Reproduction of postweaning multisystemic wasting syndrome (PMWS) in immunostimulated and non-immunostimulated 3-week-old piglets experimentally infected with prcine circovirus type 2 (PCV2)". 2002, Veterinary Microbiology, vol. 89, pp. 97-114.

Larochelle et al., "Comparative serologic and virologic study of commerical swine herds with and without postweaning multisystemic wasting syndrom." The Canadian Journal of Veterinary Research, vol. 67, 2003, pp. 114-120.

Larochelle et al., "PCR Detection and Evidence of Shedding of Porcine Circovirus Type 2 in Boar Semen." Journal of Clinical Microbiology, vol. 38, No. 12, Dec. 2000, pp. 4629-4632.

Lekcharoensuk et al., "Epitope Mapping of the Major Capsid Protein of Type 2 Porcine Circovirus (PCV2) by Using Chimeric PCV1 and PCV2". Journal of Virology, vol. 78, No. 15, Aug. 2004, pp. 8135-8145.

Li et al., "Essential Elements of the Capsid Protein for Self-Assembly into Empty Virus-Like Particles of Hepatitis E Virus". Journal of Virology, vol. 79, No. 20, Oct. 2005, pp. 12999-13006.

Li et al., "Expression and Self-Assembly of Empty Virus-Like Particle of Hepatitis E Virus". Journal of Virology, vol. 71, No. 10, Oct. 1997, pp. 7207-7213.

Liesner et al., "Efficacy of Ingelvac CircoFLEX® in face of maternal antibodies in a field trial in France." 2008 Allen D. Leman Swine Conference—Recent Research Reports, p. 9.

Liljeqvist et al., "Production of recombinant subunit vaccines: protein immunogens, live delivery systems and nucleic acid vaccines". Journal of Biotechnology, vol. 73, 1999, pp. 1-33.

Lin et al., "Mycoplasma hyorhinis in Taiwan: Diagnosis and isolation of swine pneumonia pathogen". Veterinary Microbiology, vol. 115, 2006, pp. 111-116.

Liu et al., "Bacterial Expression of an Immunologically Reactive PCV2 ORF2 Fusion Protein". 2001, Protein Expression and Purification, vol. 21, pp. 115-120.

Liu et al., "Characterization of a Previously Unidentified Viral Protein in Porcine Circovirus Type 2-Infected Cells and Its Role in Virus-Induced Apoptosis". Jul. 2005, Journal of Virology, vol. 79, No. 13, pp. 8262-8274.

Liu et al., "Development of an ELISA Based on the Baculovirus-Expressed Capsid Protein of Porcine Circovirus Type 2 as Antigen". Journal of Veterinary Medical Science, vol. 66, No. 3, 2004, pp. 237-242.

Liu et al., "Efficient production of type 2 porcine circovirus-like particles by a recombinant baculovirus". Archives of Virology, vol. 153, 2008, pp. 2291-2295.

Mackinnon, J.D., "Vaccination Ramification? An Objective Look at How Vaccination Might Affect Post-Weaning Multisystemic Wasting Syndrome (PMWS) and Porcine Dermatitis and Nephropathy Syndrome (PDNS)". 2003, The Pig Journal, vol. 51, pp. 36-63.

Maes et al., "Effect of vaccination against Mycoplasma hyopneumoniae in pig herds with an all-in/all-out production system". Vaccine, vol. 17, 1999, pp. 1024-1034.

Magar et al., "Experimental Transmission of Porcine Circovirus Type 2 (PCV2) in Weaned Pigs: a Sequential Study." Journal of Comparative Pathology, vol. 123, 2000, pp. 258-269.

Mahe et al., "Differential recognition of ORF2 protein from type 1 and type 2 porcine circoviruses and identification of immunorelevant epitopes". 2000, Journal of General virology, vol. 81, pp. 1815-1824.

Maranga et al., "Virus-Like Particle Production at Low Multiplicities of Infection With the Baculovirus Insect Cell System". Aug. 2003, Biotechnology and Bioengineering, vol. 84, No. 2, pp. 246-253.

Martelli et al., "One dose of a porcine circovirus 2 subunit vaccine induces humoral and cell-mediated immunity and protects against porcine circovirus-associated disease under field conditions". Veterinary Microbiology, vol. 149, 2011, pp. 339-351.

Mateu et al., "A Single Amino Acid substitution Affects Multiple Overlapping Epitopes in the Major Antigenic Site of Foot-and-Mouth Disease Virus of Serotype C," Journal of General Virology, vol. 71, 1990, pp. 629-637.

Mccall et al., "Improvements to the throughput of recombinant protein expression in the baculovirus/insect cell system." Protein Expression and Purification, vol. 42, 2005, pp. 29-36.

Mckeown et al., "Effects of Porcine Circovirus Type 2 (PCV2) Maternal Antibodies on Experimental Infection of Piglets with PCV2". Clinical and Diagnostic Laboratory Immunology, vol. 12, No. 11, Nov. 2005, pp. 1347-1351.

Mcnair et al., "Interlaboratory testing of porcine sera for antibodies to porcine circovirus type 2." Journal of Veterinary Diagnositc Investigation, vol. 16, 2004, pp. 164-166.

McNeilly et al., "Evaluation of a Porcine Circovirus Type 2-Specific Antigen-Captive Enzyme-Linked Immunosorbent Assay for the Diagnosis of Postweaning Multisystemic Wasting Syndrome in Pigs: Comparison with Virus Isolation, Immunohistochemistry, and the Polymerase Chain Reaction", J. Vet Diagn. Invest, 2002, 14, pp. 106-112.

Meehan et al., "Characterization of novel circovirus DNAs associated with wasting syndromes in pigs". Journal of General Virology, vol. 79, 1998, pp. 2171-2179.

Meerts et al., "Correlation between the prsence of neutralizing antibodies against porcine circovirus 2 (PCV2) and protection against replication of the virus and development of PCV2-associated disease." BMV Veterinary Research, vol. 2, No. 6, 2006, pp.1-11.

Meerts et al., "Correlation Between Type of Adaptive Immune Response Against Porcine Circovirus Type 2 and Level of Virus Replication." Viral Immunology, vol. 18, No. 2, 2005, pp. 333-341.

Merial Animal Health Ltd., "Progressis." 2011, pp. 1-2. [Accessed at http://www.noahcompendium.co.uk/Merial_Animal Health_ltd/documents/S3834.html on Apr. 12, 2011].

Midwest Research Swine, "High Health Heard Status." pp. 1-2. [Accessed at: http://midwestresearchswine.com/herd-health/high-health-herd-status/ on Jun. 27, 2016].

Minion et al., "Then Genome Sequence of Mycoplasma hyopneumoniae Strain 232, the Agent of Swine Mycoplasmosis". Nov. 2004, Journal of Bacteriology, vol. 186, No. 21, pp. 7123-7133.

Moraes et al., "*Drosophila melanogaster* S2 cells for expression of heterologous genes: From gene cloning to bioprocess development." Biotechnology Advances, vol. 30, 2012, pp. 613-638.

Morales et al., "Serendipitous Discovery and X-Ray Structure of a Human Phosphate Binding Apolipoprotein". Mar. 2006, Structure, vol. 14, pp. 601-609.

Morris et al., "Characterization of Productive and Non-Productive ACMNPV Infection in Selected Insect Cell Lines", Viro. 197, 1993, pp. 339-348.

Mortola et al., "Efficient assembly and release of SARS coronavirus-like particles by a heterologous expression system". FEBS Letters, vol. 576, 2004, pp. 174-178.

Muirhead, Mike, "Sources of information on PMWS/PDNS". The Veterinary Record, vol. 150, No. 14, Apr. 6, 2002, p. 456.

Murakami et al., "Occurrence of Swine Salmonellosis in Postweaning Multisystemic Wasting Syndrome (PMWS) Affected Pigs Concurrently Infected with Porcine Reproduction and Respiratory Syndrome Virus (PRRSV)". Journal of Veterinary Medical Science, vol. 68, 2006, pp. 387-391.

Nawagitgul et al., "Open reading frame 2 of porcine circovirus type 2 encodes a major capsid protein". 2000, Journal of General Virology, vol. 81, pp. 2281-2287.

Nawagitgul et al., Modified Indirect Porcine Circovirus (PCV) Type 2-based and Recombinant Capsid Protein (ORF-2) Based Enzyme-

(56) References Cited

OTHER PUBLICATIONS

Linked Immunosorbent Assays for Detection of Antibodies to PCV, Clinical and Diagnostic Laboratory Imunology, Ja. 2002, vol. 9, No. 1, pp. 33-40.
Neutra et al., "Optimization of protein-production by the baculovirus expression vector system in shake flasks". Applied Microbiology and Biotechnology Journal, vol. 37, No. 1, 1992, pp. 74-78.
Ng et al., "Extracellular self-assembly of virus-like particles from secreted recombinant polyoma virus major coat protein." Protein Engineering, Design & Selection, vol. 20, No. 12, 2007, pp. 591-598.
Niewiesk, Stefan, "Maternal antibodies: clinical significance, mechansim of interference with immune responses, and possible vaccination strategies." Frontiers in Immunology, vol. 5, Article 446, Sep. 2014, pp. 1-15.
Noad et al., "Virus-like particles as immunogens" Trends in Microbiology, vol. 11, No. 9, Sep. 2003, pp. 438-444.
O'Dea et al., "Porcine circovirus-associated disease in weaner pigs in Western Australia". Australian Veterinary Journal, vol. 89, No. 4, Apr. 2011, pp. 122-130.
O'Neill, Kevin Charles, "Efficacy and impact of current commercial porcine circovirus type 2 (PCV2) vaccines in dams and growing pigs." Graduate Theses and Dissertations, Graduate College, Iowa State University, Paper 12837, 2012, pp. 1-130.
Ohnesorge et al., "Efficacy Studies—Efficacy evaluation of a mixed Mycoplasma hyopneumoniae bacterin and a porcine circovirus type 2 vaccine". 2007, 1 page. [Accessed at http://www.ingelvacflex.co.uk/mycoflex/research/efficacy.php on Jul. 31, 2012].
Okuda, et al., "Experimental Reproduction of Post-Weaning Multisystemic Wasting Syndrome in Cesarean-Derived, Colostrum-Deprived Piglets Inoculated with Porcine Circovirus Type 2 (PCV2): Investigation of Quantitative PCV2 Distribution and Antibody Responses", J. Vet Diagn. Invest, 2003, 15, pp. 107-114.
Olejnik et al. "Effect of hyperosmolarity on recombinant protein productivity in baculovirus expression system." Journal of Biotechnology, vol. 102, 2003, pp. 291-300.
Olvera et al., "Comparison of porcine circovirus type 2 load in serum quantified by a real time PCR in postweaning multisystemic wasting syndrome and porcine dermatitis and nephropathy syndrome naturally affected pigs". 2004, Journa of Virological Methods, vol. 117, pp. 75-80.
Onuki et al., "Detection of Porcine Circovirus from Lesions of a Pig with Wasting Disease in Japan." The Journal of Veterinary Medical Science, vol. 61, No. 10, Oct. 1999, pp. 1119-1123.
Opriessnig et al., "A commercial vaccine based on PCV2a and an experimental vaccine based on a variant mPCV2b are both effective in protecting pigs against challenge with a 2013 U.S. variant mPCV2b strain". Vaccine, vol. 32, No. 2, 2014, pp. 230-237.
Opriessnig et al., "A PCV2 vaccine based on genotype 2b is more effective than a 2a-based vaccine to protect against PCV2b or combined PCV2a/2b viremia in pigs with concurrent PCV2, PRRSV and PPV infection". Vaccine, vol. 31, 2013, pp. 487-494.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Derivation of porcine circovirus type 2-negative pigs from positive breeding herds". Journal of Swine Health and Production, vol. 12, No. 4, Jul. and Aug. 2004, pp. 186-191.
Opriessnig et al., "Differences in virulence among porcine circovirus type 2 isolates are unrelated to cluster type 2a or 2b and prior infection provides heterologous protection". Journal of General Virology, vol. 89, No. 10, 2008, pp. 2482-2491.
Opriessnig et al., "Effect of porcine circovirus type 2 (PCV2) vaccination on porcine reproductive and respiratory syndrome virus (PRRSV) and PCV2 coinfection". Veterinary Microbiology, vol. 131, 2008, pp. 103-114.
Opriessnig et al., "Effect of porcine parvovirus vaccination on the development of PMWS in segregated early weaned pigs coinfected with type 2 porcine circovirus and porcine parvovirus". Veterinary Microbiology, vol. 98, 2004, pp. 209-220.
Opriessnig et al., "Effect of Vaccination with Selective Bacterins on Conventional Pigs Infected with Type 2 Porcine Circovirus". Veterinary Pathology, vol. 40, 2003, pp. 521-529.
Opriessnig et al., "Effects of the timing of the administration of Mycoplasma hyopneumoniae bacterin on the development of lesions associated with porcine circovirus type 2". Veterinary Record, vol. 158, No. 5, Feb. 2006, pp. 149-154.
Opriessnig et al., "Experimental Co-Infection with Porcine Circovirus Type 2 and *Salmonella typhimurium* or Lawsonia Intracellularis". Pig Progress, Jun. 2008, 1 page. [Accessed at: http://www.pigprogress.net/public/file/IPVS-oral%20presentations/Viral%20diseases/Experimental%20co-infection%20with%20PCV2%20and%20salmonella%20Typhimurium%20or%20lawsonia%20intracellularis.pdf on Mar. 17, 2010].
Opriessnig et al., "Experimental Reproduction of Postweaning Multisystemic Wasting Syndrome in Pigs by Dual Infection with Mycoplasma hyopneumoniae and Porcine Circovirus Type 2". Veterinary Pathology, vol. 41, No. 6, Nov. 2004, pp. 624-640.
Opriessnig et al., "Influence of anti-PCV2 passively-acquired antibodies on efficacy of Suvaxyn® PCV2 vaccination in pigs experimentally-infected with PCV2." American Association of Swine Veterinarians, 2007, pp. 299-300.
Opriessnig et al., "Porcine Circovirus Type 2 Infection Decreases the Efficacy of a Modified Live Porcine Reproductive and Respiratory Syndrome Virus Vaccine", Clinical and Vaccine Immunology, Aug. 2006, vol. 13, No. 8, pp. 923-929.
Ostanello et al., "Experimental infection of 3-week-old conventional colostrum-fed pigs with porcine circovirus type 2 and porcine parvovirus". Veterinary Microbiology, vol. 108, No. 3-4, Jul. 2008, pp. 179-186.
Paterson, J.E., "Health and antimicrobial resistance". Manipulating Pig Production X, Chapter 2, Proceedings of the Tenth Biennial Conference of the Australasian Pig Science Association (Inc.) (APSA) held in Christchurch, New Zealand on Nov. 27 to 30, 2005, Werribee, Victoria, Australia: Australasian Pig Association (Inc.), pp. 21-74.
Patterson et al., "Baculovirus and Insect Cell Gene Expression: Review of Baculovirus Biotechnology". Environmental Health Perspectives, vol. 103, Nos. 7-8, Jul.-Aug. 1995, pp. 756-759.
Patterson et al., "Interlaboratory Comparison of Porcine Circovirus-2 Indirect Immunofluorescent Antibody Test and Enzyme-Linked Immunosorbent Assay Results on Experimentally Infected Pigs". Journal of Veterinary Diagnostic Investigation, vol. 23, 2011, pp. 206-212.
Pejawar-Gaddy et al., "Generation of a Tumor Vaccine Candidate Based on Conjugation of a MUC1 Peptide to Polyionic Papillomavirus Virus-Like Particles (VLPs)." Cancer Immunogy, Immunotherapy, vol. 59, No. 11, Nov. 2010, pp. 1648-1696.
Poljak et al., "Spread of porcine circovirus associated disease (PCVAD) in Ontario (Canada) swine herds: Part I. Exploratory spatial analysis". BMC Veterinary Research, vol. 6, No. 59, 2010, pp. 1-15.
Polo et al., "Half-life of porcine antibodies absorbed from a colostrum supplement containing porcine immunoglobulins." Journal of Animal Science, vol. 90, 2012, pp. 308-310.
Poppe et al., "*Salmonella typhimurium* DT104: A virulent and drug-resistant pathogen". Canadian Veterinary Journal, vol. 39, 1998, pp. 559-565.
Pyle et al., "Secretion of biologically active human proapolipoprotein A-I in a baculovirus-insect cell system: protection from degradation by protease inhibitors". Journal of Lipid Research, vol. 36, 1995, pp. 2355-2361.
Quintana et al., "Clinical and pathological observations on pigs with postweaning multisystemic wasting syndrome". 2001, The Veterinary Record, vol. 149, pp. 357-361.
Ragona et al., "The Transcriptional Factor Egr-1 Is Synthesized by Baculovirus-Infected Insect Cells in an Active, DNA-Binding Form". DNA and Cell Biology, vol. 10, No. 1, 1991, pp. 61-66.

(56) References Cited

OTHER PUBLICATIONS

Remington et al., "Active Immunizing Agents." Remington: The Science and Practice of Pharmacy, Twentieth Edition, 2000, p. 1569.
Reynaud et al., "Comparison of Clinical, Lesional and Virological Signs in Pigs With and Without Experimental PMWS." Proceedings of the 17th International Pig Veterinary Society Congress, Ames, Iowa, USA, Jun. 2002, vol. 1, p. 172.
Riggs et al., "Protective Monoclonal Antibody Defines a Circumsporozoite-Like Glycoprotein Exoantigen of Cryptosporidium parvum Sporozoites and Merozoites". The Journal of Immunology, vol. 158, 1997, pp. 1787-1795.
Robinson et al., "Immunofluorescence." IHC Staining Methods, Fifth Edition, Chapter 10, 2009, pp. 61-65.
Rodríguez-Arrioja et al., "Dynamics of procine circovirus type 2 infection in a herd of pigs with postweaning multisystemic wasting syndrome". American Journal of Veterinary Research, vol. 63, No. 3, Mar. 2002, pp. 354-357.
Roesler et al., "Oral vaccination of pigs with an invasive gyrA-cpxA-rpoB *Salmonella Typhimurium* mutant". Vaccine, vol. 23, No. 5, Dec. 2004, pp. 595-603.
Rossow et al., "Experimental porcine reproductive and respiratory syndrome virus infection in one-, four-, and 10-week-old pigs." Journal of Veterinary Diagnositc Investigations, vol. 6, 1994, pp. 3-12.
Rota et al., "Expression of influenza A and B virus nucleoprotein antigens in baculovirus." Journal of General Virology, vol. 71, 1990, pp. 1545-1554.
Rotto, Hans "Diagnosis, Vaccination and Field Experiences with PCV-AD". Iowa Pork Progress, 2007, pp. 1-10.
Morris et al., "Efficient assembly and release of SARS coronavirus-like particles by a heterologous expression system", Journal of Virology, vol. 66, No. 12, Dec. 1992, pp. 7397-7405.
GenBank accession No. AEY79491.1, Jan. 30, 2012, Huang et al. Sequence alignment of Seq ID No. 5 with Geneseq database access No. AWF75404 Apr. 2009.
GenBank accession No. JN639856.1, Jan. 30, 2012.
GenBank accession No. JN382179.2, Apr. 17, 2012.
Magar et al.; 2000, Can. J. Vet Res.; 64:184-186.
GenBank accession No. JN181915.1, Jun. 30, 2012.
Takada-Iwao et al., "Porcine circovirus type 2 (PCV2) vaccination reduces PCV2 in a PCV2 and *Salmonella enterica* serovar Choleraesuis coinfection model". Veterinary Microbiology, vol. 162, 2013, pp. 219-223.
Thacker et al. "Porcine Respiratory Disease Complex (PRDC)". Thai Journal of Veterinary Medicine, vol. 32, Supp., 2002, pp. 126-134.
Thacker et al., "Effect of vaccination on the potentiation of porcine reproductive and respiratory syndrom virus (PRRSV)-induced pneumonia by Mycoplama hyopneumoniae". Vaccine, vol. 18, 2000, pp. 1244-1252.
Thacker, Eileen L., "Diagnosis of Mycoplama hyopneumoniae". Journal of Swine Health Production, vol. 12, No. 5, 2004, pp. 252-254.
Thacker, Eileen L., "Mycoplasmal Diseases". Diseases of Swine, 9th Edition, Ch. 42, 2006, pp. 701-717.
Thomas et al., "Effect of PCV2 passive antibody levels on immunization with chimeric PCV1-2 vaccine and challenge with wild-type PCV2." American Association of Swine Veterinarians, 2005, pp. 23-25.
Truong et al., "Identification of an immunorelevant ORF2 epitope from porcine circovirus type 2 as a serological marker for experimental and natural infection". Archives of Virology, vol. 146, 2001, pp. 1197-1211.
UniProt Database Accession No. G3LHI3, by Cadar et al. "Detection of natural inter- and intra-genotype recombination events revealed by cap gene analysis and decreasing prevalence of PCV2 in wild boars." Inectious Genet. Evol., vol. 12, 2012, pp. 420-427, Nov. 16, 2011, p. 1.
UniProt Database Accession No. O91862 submitted Nov. 1, 1998 by Meehan et al., Characterization of novel circovirus DNAs associated iwth wasting sydromes in pigs. Journal of General Virology, 1998; 79: 2171-2179, 1 page.
UniProt Database Accession No. Q9YTB6, Direct Submission, Wang et al., May 1, 1999, 1 page.
UniProt Database Accession No. WOG6J4, by Shu et al., "Sequence analysis of complete genome of fifteen porcine circovirus type 2 strains in Jiangsu province". Mar. 19, 2014, 1 page.
Urniza et al., "Duration of Immunity Study in Pigs Vaccinated with an Inactivated/Adjuvanted Vaccine 'Chimeric Porcine Circovirus Type 1/Type 2' in Front of a Challenge with PCV2 European Strain." Proccedings of the 19th IPVS Congress, Copenhagen, Denmark, vol. 2, Abstract No. P.07-09, 2006, p. 108.
Vansickle, J., "Circovirus Grips Industry". Jul. 15, 2006, National Hog Farmer.
Vasconcelos et al., "Swine and Poultry Pathogens: the Complete Genome Sequences of Two Strains of Mycoplasma hyopneumoniae and a Strain of Mycoplasma synoviae". Aug. 2005, Journal of Bacteriology, vol. 187, No. 16, pp. 5568-5577.
Vicente et al., "Epidemiological Study on Porcine Circovirus type 2 (PCV2) Infection in The European Wild Boar (*Sus scrofa*) in Spain." Proceedings of the 18th IPVS Congress, vol. 1, Hamburg, Germany, 2004, p. 9.
Vido Swine Technical Group-Linking Knowledge to practical solutions "Vaccination Guidelines for Swine". Jun. 2004, www.vido.org.
Vidor, E. "The Nature and Consequences of Intra- and Inter-Vaccine Interference." Journal of Comparative Pathology, vol. 137, 2007, pp. S62-S66.
Vincent et al., "Dendritic Cells Harbor Infetious Porcine Circovirus Type 2 in the Abscence of Apparent Cell Modulation or Replication of the Virus". Dec. 2003, Journal of Virology, vol. 77, No. 24, pp. 13288-13300.
Viscidi et al., "Age-Specific Seroprevalence of Merkel Cell Polyomavirus, BK Virus, and JC Virus." Clinical and Vaccine Immunology, vol. 18, No. 10, Oct. 2011, pp. 1737-1743.
Walker, et al., "Development and application of a competitive enzyme-linked immunosorbent assay for the detection of serum antibodies to porcine circovirus type 2". 2000, Journal of Veterinary Diagnostic Investigation, vol. 12, pp. 400-405.
Wan et al., "Comprehensive Prevention and Control Techniques for Porcine Circovirus Type 2 Infection". Chinese Swine Industry, No. 3, 2006, pp. 42-45.
Wang et al., "Construction and immunogenicity of recombinant adenovirus expressing the capsid protein of porcine circovirus 2 (PCV2) in mice". Vaccine, vol. 24, 2006, pp. 3374-3380.
Warren et al., "Effect of Osmolality of the Cellular Microenvironment." Encyclopedia Of Industrial Biotechnology: Bioprocess, Bioseparation, and Cell Technology: Animal Cells, Hybridomas, Human Antibody Production, John Wiley & Sons, Inc., 2010, pp. 1-16.
Web site: "Does stress-free livestock mean safer food?" http://www.foodnavigator.com/Financial-Industry/Does-stress-free-livestock-mean-safer-food Accessed on: Jun. 4, 2004.
Weibel et al., "A field efficacy study with Enterisol® Ileitis and Ingelvac CircoFLEX® in Switzerland". Poster Presentations, Porcine Circovirus Associated Diseases (PCVAD-Control) (p. 113), Proceedings of the 21st IPVS Congress, Vancourver, Canada, Jul. 18-21, 2010, p. 419.
Weingartl et al., "Porcine circovirus structure and replication: a minireview". Agriculture, vol. 1, 2002, pp. 11-14.
Wikipedia "Specific-pathogen-free". Wikipedia, The Free Encyclopedia, May 28, 2016, at 04:21, pp. 1-3 [Accessed at https://en.wikipedia.org/w/index.php?title=Specific-pathogen-free&oldid=722441484 on Jun. 27, 2016.
Williams et al., "Combined vaccines and simultaneous administration: Current issues and perspectives". Annals of the New York Academy of Sciences, vol. 754, 1995, pp. xi-xv, 35-47.
Wu et al., "Replication, Integration, and Packaging of Plasmid DNA following Cotransfection with Baculovirus Viral DNA". Journal of Virology, vol. 73, No. 7, Jul. 1999, pp. 5473-5480.

(56) References Cited

OTHER PUBLICATIONS

Xia et al., "Preparation of and Immunity Tests with Canine Coronavirus BEI Inactivated Vaccine". Chinese Journal of Veterinary Medicine, vol. 37, No. 3, 2001, pp. 37-38.
Yamada et al., "Evaluation of the Efficacy of Inactivated Vaccine against *Salmonella enteritidis* Infection in Chicken". Journal of the Japanese Society on Poultry Diseases, vol. 35, No. 1, 1999, pp. 13-21. (English Summary at p. 21).
Yamaji et al., "Efficient production of Japanese encephalitis virus-like particles by recombinant lepidopteran insect cells." Applied Microbiology and Biotechnology, vol. 97, 2013, pp. 1071-1079.
Yamaji et al., "Optimal Production of Recombinant Protein by the Baculovirus-Insect Cell System in Shake-Flask Culture with Medium Replacement." Journal of Bioscience and Bioengineering, vol. 87, No. 5, 1999, pp. 636-641.
Yang, "A Survey on Porcine Circovirus Type 2 Infection and Phylogenetic Analysis of its ORF2 Gene in Hangzhou, Zhejiang Province, CN," J. Zhejiang Univ. Science B, vol. 9(2), 2008, pp. 148-153.
Yuan et al., "Immunology of the porcine respiratory disease complex". Animal Science Abroad in Pigs and Poultry, No. 5, 2002, pp. 36-38.
Zhai et al., "Co-existence of multiple strains of porcine circovirus type 2 in the same pig from China". Virology Journal, vol. 8:517, 2011, pp. 1-5.
Zhang et al., "Cytokine and chemokine mRNA expression profiles in tracheobronchial lymph nodes from pigs singularly infected or coinfected with porcine circovirus type 2 (PCV2) and Mycoplasma hyopneumoniae (MHYO)". Veterinary Immunology and Immunopathology, vol. 140, 2011, pp. 152-158.
Shi et al., "Protein N-Glycosylation in the Baculovirus-Insect Cell System." Current Drug Targets, vol. 8, No. 0, Oct. 2007, pp. 1116-1125.
Sequence Alignment of Seq ID No. 1 with UniProt database access No. A7YF28_PCV2 by Li et al 2007.
Sequence Alignment of Seq ID No. 1 with UniProt database access No. F8V1X0_PCV2 by Turcitu et al 2011.
Beach et al., "Chimeric Porcine Circoviruses (PVC) Containing Amino Acid Epitope Tags in the C Terminus of the Capsid Gene Are Infectious and Elicit both Anti-Epitope Tag Antibodies and Anti-PCV Type 2 Neutralizing Antibodies in Pigs", Journal of Virology, vol. 85, No. 9, May 2011, pp. 4591-4595.
Hu et al., "Generation and immunogenicity of porcine circovirus type 2 chimeric virus-like particles displaying porcine reproductive and respiratory syndrome virus GP5 epitope B." Vaccine, vol. 34, No. 16, 2016, pp. 1896-1903.
Database WPI, Week 201562, AN 2015-38559T, Thomson Scientific, London, GB; Jun. 10, 2015, 2 pages.
Trible et al., "Genetic variation of porcine circovirus type 2 {PCV2) and its relevance to vaccination, pathogenesis and diagnosis." Virus Research, vol. 164, 2012, pp. 68-77.
Trible et al., "Antibody Recognition of Porcine Circovirus Type 2 Capsid Protein Epitopes after Vaccination, Infection, and Disease." Clinical and Vaccine Immunology, vol. 18, No. 5, May 2011, pp. 749-757.
Khayat et al., "The 2.3-Angstrom Structure of Porcine Circovirus 2." Journal of Virology, vol. 85, No. 15, Aug. 2011, pp. 7856-7862.
3Uo et al., "Porcine circovirus type 2 {PCV2): genetic variation and newly emerging gentoypes in China." Virology Journal, vol. 7, No. 1, , 2010, pp. 1-12 (273).
Kekarainen et al., "Genetic variability of porcine circovirus 2 in vaccinating and non-vaccinating commercial farms", Journal of General Virology, vol. 95, 2014, pp. 1734-1742.
GenBank accession No. AEG89578, Dec. 6, 2011, Turcitu et al.
GenBank accession No. AEP19232, Apr. 3, 2012, Cai et al.
Rovira et al., "Experimental Inoculation of Conventional Pigs with Porcine Reproductive and Respiratory Syndrome virus and Porcine Circovirus 2", J. Virol, Apr. 2002, vol. 76, No. 7, pp. 3232-3239.
Royer et al., "Susceptibility of porcine circovirus type 2 to commercial and laboratory disinfectants". Journal of Swine Health and Production, vol. 9, No. 6, 2001, pp. 281-284.
Rueda et al., "Effect of Different Baculovirus Inactivation Procedures on the Integrity and Immunogenicity of Porcine Parvovirus-Like Particles", Vaccine, 2001, 19, pp. 726-734.
Safron et al., "The SPF Pig in Research." ILAR Journal, vol. 38, No. 1, 1997, pp. 28-31.
Schaefer et al., "Characterization and Formulation of Multiple Epitope-Specific Neutralizing Monoclonal Antibodies for Passive Immunization against Cryptosporidiosis". Infection and Immunity, vol. 68, No. 5, May 2000, pp. 2608-2616.
Sedlik et al., "Recombinanat parvovirus-like particles as an antigen carrier: A novel nonreplicative exogenous antigen to elicit protective antiviral cytotoxic T cells". Proceedings of the National Academy of Sciences, vol. 94, Jul. 1997, pp. 7503-7508.
Segales et al., "Changes in Peripheral Blood Leukocyte Populations in Pigs with Natural Postweaning Multisystemic Wasting Syndrome (PMWS)", Vet. Immunology & Immunopathology, 2001, 81, pp. 37-44.
Segales et al., "Epidemiology of Porcine Circovirus Type 2 Infection: What do we Know?", Pig News & Information, 2003, vol. 24, No. 4, pp. 103N-110N.
Segales et al., "*Granulomatous enteritis* and Lymphadenitis in Iberian Pigs Naturally Infected with Lawsonia intracellularis". Veterinary Pathology, vol. 38, No. 3, 2001, pp. 343-346.
Segales et al., "Pathological findings associated with naturally acquired porcine circovirus type 2 associated disease". Veterinary Microbiology, vol. 98, 2004, pp. 137-149.
Segales et al., "Postweaning Multisystemic Wasting Syndrome (PMWS) in Pigs, A Review", Vet. Quarterly, 2002, 24(3), pp. 109-124.
Segalés et al., "Immunosuppression in postweaning multisystemic wasting syndrome affected pigs". Veterinary Microbiology, vol. 98, 2004, pp. 151-158.
Segalés et al., "Porcine Circovirus Diseases". Diseases of Swine, 9th Edition, Chapter 14, Blackwell Publishing, Ames, Iowa, 2006, pp. 299-307.
Segalés et al., "Postweaning Multisystemic Wasting Syndrome and Porcine Circovirus Ty;e 2: The European Perspective". Trends in Emerging Viral Infections of Swine, Ch. 9.3, PMWS and PCV2: European Perspective, 2002, pp. 297-303.
Seq ID No. 11, Sequence Alignment with UniProt Database Accession No. O91862_PCV2 submitted Nov. 1998 by Meehan et al. (Journal of General Virology, 1998; 79: 2171-2179).
Seq ID No. 1 Sequence Alignment with GenEmbl Database Accession No. GQ845027 submitted Mar. 31, 2010 in Li et al., "Genetic analysis of porcine circovirus type 2 (PCV2) strains isolated between 2001 and 2009: genotype PCV2b predominate in postweaning multisystemic wasting syndrome occurrences in eastern China". Virus Genes, vol. 40, No. 2, 2010, pp. 244-251, 5 pages.
Seq ID No. 1 Sequence Alignment with GenEmbl Database Accession No. JN006448 submitted Dec. 6, 2011 in Turcitu et al., "Genetic diversity of porcine circovirus type 2 (PCV2) in the Romanian wild board population". Res. Vet. Sci., vol. 91, No. 3, 2011, E103-106, 5 pages.
Seq ID No. 1 Sequence Alignment with Geneseq Database Accession No. AWF75438 submitted Apr. 2, 2009 in US2009/0017064, 3 pages.
Seq ID No. 1 Sequence Alignment with Geneseq Database Accession No. AZR61798 submitted Feb. 16, 2012 in CN102296089, 2 pages.
Seq ID No. 11 Sequence Alignment with Geneseq Database Accession No. AAO23063 submitted Oct. 2003 in WO 2003049703, 2 pages.
Seq ID No. 13 Sequence Alignment with UniProt Database Accession No. B1PXD8_PCV2, Submitted Apr. 2008, 1 page.
Seq ID No. 15 Sequence Alignment with UniProt Database Accession No. B1PXE4_PCV2, Submitted Apr. 2008, 1 page.
Seq ID No. 2 Sequence Alignment with Geneseq Database Accession No. ARY99931 submitted Aug. 21, 2008 in WO2008/076915, 2 pages.

(56) References Cited

OTHER PUBLICATIONS

Seq ID No. 2 Sequence Alignment with Geneseq Database Accession No. AWF75438 submitted Apr. 2, 2009 in US2009/0017064, pp. 1-3.
Seq ID No. 22 Sequence Alignment with UniProt Database Accession No. I6QG49_PCV2, Submitted Oct. 2012, 1 page.
Seq ID No. 23 Sequence Alignment with UniProt Database Accession No. C9EJF3_PCV2, Submitted Nov. 2009, 1 page.
Seq ID No. 24 Sequence Alignment with UniProt Database Accession No. C9E8DC_9CIRC, Submitted Nov. 2009, 1 page.
Seq ID No. 42 Sequence Alignment with UniProt Database Accession No. H2DQN2_PCV2, Submitted Mar. 2012, 1 page.
Seq ID No. 5 Sequence Alignment with Geneseq Database Accession No. ABB99415, submitted Jan. 2003 in WO2002/77210, 2 pages.
Seq ID No. 5 Sequence Alignment with UniProt Database Accession No. Q9YTB6_PCV2 Submitted May 1999 by Fenaux et al. in Journal of Clinical Microbiology, 2000; 38: 2494-2503, 2 pages.
Seq ID No. 6 Sequence Alignment with Geneseq Database Accession No. ADA9081 submitted Nov. 2003 in USPgPUB 2003/096377, 2 pages.
Seq ID No. 6 Sequence Alignment with UniProt Database Accession No. Q9YTB6_PCV2 Submitted May 1999 by Fenaux et al. in Journal of Clinical Microbiology, 2000; 38: 2494-2503, 2 pages.
Seq ID No. 3 Sequence Alignment with Geneseq Database Accession No. ABV72527 submitted Jan. 2003, in WO2002/077210, 3 pages.
Seq ID No. 4 Sequence Alignment with Geneseq Database Accession No. ABV72527 submitted Jan. 2003, in WO2002/077210, 3 pages.
Sequence Alignment of Seq ID No. 2 with Seq ID No. 2 of parent U.S. Appl. No. 14/504,839; now U.S. Pat. No. 9505808, Oct. 2014, 1 page.
Sequence Alignment of Seq ID No. 5 with Seq ID No. 5 of parent U.S. Appl. No. 14/504,839; now U.S. Pat. No. 9505808, Oct. 2014, 1 page.
Shen et al., "Comparison of commercial and experimental porcine circovirus type 2 (PCV2) vaccines using a triple challenge with PCV2, porcine reproductive and respiratory syndrome virus (PRRSV), and porcine parvovirus (PPV)". Vaccine, vol. 28, 2010, pp. 5960-5966.
Sibila et al., "Use of a Polymerase Chain Reaction Assay and ELISA to Monitor Porcine Circovirus Type 2 Infection in Pigs From Farms with and without Postweaning Multisystemic Wasting jSyndrome", AJVR, Jan. 2004, vol. 65, No. 1, pp. 88-92.
Sico et al., "Enhanced Kinetic Extraction of Parvovirus B19 Structural Proteins." Biotechnology and Bioengineering, vol. 80, No. 3, Nov. 5, 2002, pp. 250-256.
Siebel, K. "PCV2 vaccination changing the pig industry Part 2. Global experiences from the field around one-shot vaccination". Pig Progress, vol. 26, No. 1, 2010, pp. 11-13.
Siegrist et al., "Influence of maternal antibodies on vaccine responses: inhibition of antibody but not T cell responses allows successful early prime-boost strategies in mice." European Journal of Immunology, vol. 28, 1998, pp. 4138-4148.
Siegrist, Claire-Anne, "Mechanisms by which maternal antibodies influence infant vaccine responses: review of hypotheses and definition of main determinants." Vaccine, vol. 21, 2003, pp. 3406-3412.
Sigma-Aldrich®, "Product Information for TNM-FH Insert Media", 2014, 1 page.
Smith et al., "Observations on Experimental Oral Infection with *Salmonella dublin* in Calves and *Salmonella choleraesuis* in Pigs". Journal of Pathology and Bacteriology, vol. 93, No. 1, 1967, pp. 141-156.
Sorden et al., "Development of a Polyclonal-antibody-based Immunohystochemical Method for the Detection of Type 2 Porcine circovirus in Formalin-Fixed, Paraffin-Embedded Tissue", J. Vet Diagn. Inest, 1999, 11, pp. 528-530.

Spear, Maynard L., "Specific Pathogen Free Swine." iowa State University Veterinarian, vol. 22, Iss. 3, Article 2, 1960, pp. 134, 136-137.
Spier, R.E., "Multivalent Vaccines: Prospects and Challenges". Folia Microbiologica, vol. 42, No. 2, 1997, pp. 105-112.
Stokka et al., "Modified-Live Vs. Killed Vaccines—Which is Better?" BeefMagazine.com, Oct. 2000, pp. 1-6. [Accessed at: http://beefmagazine.com/mag/beef_modifiedlive_vs_killed on Nov. 4, 2014].
Stoltenow, Charles L. "Getting the Most Out of a Vaccine Program". Proceedings, The Range Beef Cow Symposium XIX, Rapid City, SD, 2005, pp. 139-144.
Suradhat et al., "The influence of maternal immunity on the efficacy of a classical swine fever vaccine against classical swine fever virus, genogroup 2.2, infection". Veterinary Microbiology, vol. 92, 2003, pp. 187-194.
Fort et al., "Porcine circovirus type 2 (PCV2) vaccination of conventional pigs prevents viremia against PCV2 isolates of different genotypes and geographic origins". Vaccine, vol. 26, No. 8, 2008, pp. 1063-1071.
Gagrcin et al., "Complex of Swine Respiratory Diseases-Strategy of control in light of latest knowledge". Veterinarski Glasnik, vol. 58, No. 7-8, 2004, pp. 409-418. [English Abstract at p. 417.].
Genbank Accession No. AAC61738, Version AAC61738.1 GI:3661517, Sep. 29, 1998.
GenBank Accession No. AF201311, Direct Submission, submitted Feb. 23, 2000 in Mankertz et al., "Characterization of PCV-2 isolates from Spain, Germany and France", Virus Research, vol. 66, No. 1, 2000, pp. 65-77, 2 pages.
Genbank Accession# AAF87231.1, PCV2 ORF2 Protein, 2000.
Gerber et al., "Fetal infections and antibody profiles in pigs naturally infected with porcine circovirus type 2 (PCV2)." The Canadian Journal of Veterinary Research, vol. 76, 2012, pp. 38-44.
Gizurarson, Sveinbjörn, "Clinically Relevant Vaccine-Vaccine Interactions". BioDrugs, vol. 9, No. 6, Jun. 1998, pp. 443-453.
Goldenthal et al., "Overview-Combination Vaccines and Simultaneous Administration: Past, Present, and Future." Annals of the New York Academy of Sciences, vol. 754, 1995, pp. xi-xiv.
Grau-Roma et al., "Recent advances in the epidemiology, diagnosis and control of diseases caused by porcine circovirus type 2." The Veterinary Journal, vol. 187, 2011, pp. 23-32.
Groner, et al., The Biology of Baculoviruses, vol. 1, Biological Properties and Molecular Biology, 1986, Chapter 9, Specificity and Safety of Baculoviruses, pp. 177-202.
Gualandi et al., "The Ability by Different Preparations of Porcine Parvovirus to Enhance Humoral Immunity in Swine and Guinea Pigs". Microbiologica, vol. 11, No. 4, 1988, pp. 363-369.
Gualandi et al., "The Response of Pregnant Gilts Previously Given An Inactivated Preparation of Porcine Parvovirus (PPV) to Challenge Infection with a Fully Virulent PPV". Microbiologica, vol. 15, 1992, pp. 391-396.
Ha et al., "Outbreak of salmonellosis in pigs with postweaning multisystemic wasting syndrome". Veterinary Record, vol. 156, No. 18, Apr. 2005, pp. 583-584.
Haake et al., "Influence of age on the effectiveness of PCV2 vaccination in piglets with high levels of maternally derived antibodies". Veterinary Microbiology, vol. 168, 2014, pp. 272-280.
Haiwick et al., "Trivalent vaccine mixture protects against simultaneous challenge with M. hyopneumoniae, PCV2, and PRRS virus". Allen D. Leman Swine Conference, 2010, p. 176.
Halbur et al., "Porcine Circovirus Associated Disease (PCVA) . . . a "Double Bogey"." Carthage Veterinary Service ltd. 16th Annual Swine Conference, Jan. 1, 2006, 3 pages. [Accessed at http://www.prairieswine.com/porcine-circovirus-associated-disease-pcva%E2%80%A6-a-%E2%80%9Cdouble-bogey%E2%80%9D/ on Sep. 1, 2015].
Halbur et al., "Update on Porcine Circovirus Type 2 (PCV2)-Associated Diseases." Veterinary Diagnostic and Production Animal Medicine, Iowa State University, Ames, IA, 12th Annual Swine Disease Conference for Swine Practitioners, Nov. 2004, pp. 12-23.
Hallsworth et al., "Limits of life in MgCl2-containing environments: chaotropicity defines the window." Environmental Microbiology, vol. 9, No. 3, 2007, pp. 801-813.

(56) References Cited

OTHER PUBLICATIONS

Hamel et al., "Nucleotide Sequence of Porcine Circovirus Associated with Postweaning Multisystemic Wasting Syndrome in Pigs". Journal of Virology, vol. 72, No. 6, Jun. 1998, pp. 5262-5267.
Han et al., "Self-Assembly of the Recombinant Capsid Protein of a Bovine Norovirus (BoNV) into Virus-Like Particles and Evaluation of Cross-Reactivity of BoNV with Human Noroviruses." Journal of Clinical Microbiology, vol. 43, No. 2, Feb. 2005, pp. 778-785.
Harayama et al., "Maternal porcine circovirus type 2-memory T cells transfers to piglets through colostrums ingestion." Proceedings of the 5th Asian Pig Veterinary Society Congress Mar. 7-9, 2011, Pattaya, Thailand, p. P82.
Harding et al. "Dual heterologous porcine circovirus genogroup 2a/2b infection induces sever disease in germ-free pigs." Veterinary Microbiology, vol. 145, 2010 pp. 209-219.
Harding et al., "Postweaning multisystemic wasting syndrome: Epidemiology and clincial presentation." Swine Health and Production, vol. 6, No. 6, 1998, pp. 249-254.
Harding et al., "Recognizing and diagnosing postweaning multisystemic wasting syndrome (PMWS)". Swine Health and Production, vol. 5, No. 5, 1997, pp.201-203.
Harding, John C. "Post Weaning Multisystemic Wasting Syndrome (PMWS): Preliminary Epidemiology and Clinical Findings." Proceedings of the Western Canadian Association of Swine Practitioners, 1996 Annual Meeting, Oct. 1996, p. 21.
Harms et al., "Three cases of porcine respiratory disease complex associated with porcine circovirus type 2 infection". Journal of Swine Health and Production, vol. 10, No. 1, 2002, pp. 27-30.
Haruna et al., "The role of immunostimulation in the development of postweaning multisystemic wasting syndrome in pigs under field conditions". Canadian Journal of Veterinary Research, vol. 70, Oct. 2006, pp. 269-276.
Hesse et al., "Evidence for recombination between PCV2a and PCV2b in the field." Virus Research, vol. 132, 2008, pp. 201-207.
Hilgers et al., "Alkyl-esters of polyacrylic acid as vaccine adjuvants". Vaccine, vol. 16, No. 16, 1998, pp. 1575-1581.
HiMedia Laboratories Pvt. Ltd., "TNM-FH Insect Medium With Lactalbumin hydrolysate, Yeast extract, L-Glutamine and Sodium bicarbonate 1X Liquid Insect Cell Culture Medium." Revision: Jan. 2013, pp. 1-2.
Hirai et al., "Dual infection with PCV-2 and porcine epidemic diarrhoea virus in neonatal piglets". The Veterinary Record, vol. 148, 2001, pp. 482-484.
Hodgins et al., "Influence of age and maternal antibodies on antibody responses of neonatal piglets vaccinated against Mycoplasma hyopneumoniae." Journal of Swine Health and Production, vol. 12, No. 1, Jan.-Feb. 2004, pp. 10-16.
Hoogland et al., "Effects of adjuvants on porcine circovirus type 2-associated lesions". Journal of Swine Health and Production, vol. 14, No. 3, 2006, pp. 133-139.
Hu et al., "Baculovirus as a highly efficient expression vector in insect and mammalian cells." Acta Pharmacologica Sinica, vol. 26, No. 4, Apr. 2005, pp. 405-416.
Huang et al., "Porcine circovirus type 2 (PCV2) infection decreases the efficacy of an attenuated classical swine fever virus (CSFV) vaccine". Veterinary Research, vol. 42, 115, 2011, pp. 1-9.
Hulst et al., "Glycoprotein E1 of Hog Cholera Virus Expressed in Insect Cells Protects Swine from Hog Cholera." Journal of Virology, vol. 67, No. 9, Sep. 1993, pp. 5435-5442.
Hüser et al., "Baculovirus Vectors: Novel Mammalian Cell Gene-Delivery Vehicles and Their Applications". American Journal of Pharmacogenomics, vol. 3, No. 1, 2003, pp. 53-63.
Insel et al., "Potential Alterations in Immunogenicity by Combining or Simultaneously Administering Vaccine Components." Annals of the New York Academy of Sciences, vol. 754, 1995, pp. 35-47.
Intervet Schering-Plough Animal Health, "Porcilis PRRS Data Sheet." 2011, pp. 1-3. [Accessed at http://www.intervet.co.uk/Products_Public/Porcilis_PRRS/Product_Datasheet.aspx on Apr. 12, 2011.].

Inumaru et al., "Expression of biologically active recombinant porcinee GM-CSF by baculovirus gene expression system". 1998, Immunology and Cell Biology, vol. 76, pp. 195-201.
Invitrogen Life Technologies, "Growth and Maintenance of Insect Cell Lines". Insect Cell Lines Manual, Version K, Jul. 12, 2002, pp. 1-34. [Accessed at http://www.med.unc.edu/pharm/sondeklab/Lab%20Resources/manuals/insect_cell_manual.pdf on Nov. 25, 2013].
Invitrogen Life Technologies, "Guide to Baculovirus Express Vector Systems (BEVS) and Insect Cell Culture Techniques". Feb. 27, 2002, pp. 1-130. [Accessed at https://tools.thermofisher.com/content/sfs/manuals/bevtest.pdf].
Iowa State University, "Lyphoid Depletion: PCV2-Associated Lymphoid Depletion"., 2013, pp. 1-2. [Accessed at: http://vetmed.iastate.edu/research/labs/pcv2/pcv2-associated-disease/lymphoid-depleti . . . on Dec. 14, 2013].
Jensen et al., "Distinction between Porcine Circovirus Type 2 Enteritis and Porcine Proliferative Enteropathy caused by Lawsonia intracellularis ". Journal of Comparative Pathology, vol. 135, 2006, pp. 176-182.
Jensen, Poul Moesgaard, "The Danish SPF-System Developments and challenges in the future.", 2013, 18 pages. [Accessed at: http://giqs.org/fileadmin/web_giqs/content/PDFs/PDFs_Quarisma/projektplattform/PDF_neu2013/SPF-Sundhedsstyringen_2013_QUARISMA_Holland.pdf].
Jensen, Poul Moesgaard, "The Danish SPF-Sytem Developments and challenges in the future." Quarisma-Workshop, May 16, 2013, pp. 1-18. [Accessed at: http://giqs.org/fileadmin/web_giqs/content/PDFs/PDFs_Quarisma/projektplattform/PDF_neu2013/SPF-Sundhedsstyringen_2013_QUARISMA_Holland.pdf].
Jiang et al., "Expression, Self-Assembly, and Antigenicity of the Norwalk Virus Capsid Protein". Journal of Virology, vol. 66, No. 11, Nov. 1992, pp. 6527-6532.
Jiang et al., "Synthesis of rotavirus-Like Particles in Insect Cells: Comparative and Quantitative Analysis". Biotechnology and Bioengineering, vol. 60, No. 3, 1998, pp. 369-374.
Ju et al., "Immunogenicity of a recombinant pseudorabies virus expressing ORF1-ORF2 fusion protein of porcine circovirus type 2". 2005, Veterinary Microbiology, vol. 109, pp. 179-190.
Kamstrup, et al., "Immunisation against PCV2 structural protein by DNA vaccination of mice". 2004, Vaccine, vol. 22, pp. 1358-1361.
Chae, C. "A review of porcine circovirus 2-associated syndromes and diseases". The Veterinary Journal, vol. 169, No. 3, 2005, pp. 326-336.
Chae, C., "Postweaning multisystemic wasting syndrome: a review of aetiology, diagnosis and pathology". 2004, The Veterinary Journal, vol. 168, pp. 41-49.
Charbonneau, G., "Canadian Experiences with Porcine Circovirus Associated Disease". 2007, Iowa Pork Congress; 30 pages.
Charles River Laboraties International, Inc., "Indirect Fluorescent Antibody (IFA) Assay." Technical Sheet, V.2, 2011, pp. 1-2.
Charreyre et al., "Vaccination Concepts in Controlling PCV2-Associated Diseases." Merial, 18th IPVS, Hamburg (Germany), Jun. 2004, pp. 95-107.
Chen et al., "Serological survey of serum antibodies against porcine circovirus type 2 (PCV2) in swine, chicken, duck, goat and cattle fromZhejiang province, China". Revue de Médecine Vétérinaire, vol. 158, Nos. 8-9, 2007, pp. 458-462.
Cheung et al., "Kinetics of Porcine Circovirus Type 2 Replication". Archives of Virology, vol. 147, 2002, pp. 43-58.
Chevez et al., "Long-term analysis of PCV2 prevalence in a Mexican herd using Ingelvac CircoFLES®". 22nd International Pig Veterinary Society Congress, Virology and Viral Diseases-PCV2, 2012, p. 908.
Chiou, et al., "The Effect of Porcine Circovirus Infection on the Immune Response of Pigs After Vaccination Against Classical Swine Fever and Pseudorabies". 2006, Proceedings of the 19th IPVS Congress, Copenhagen, Denmark, p. 79.
Chung et al., "Real-time PCR for quantitation of porcine reproductive and respiratory syndrome virus and porcine circovirus type 2 in naturally-infected and challenged pigs". Journal of Virological Methods , vol. 124, 2005, pp. 11-19.

(56) References Cited

OTHER PUBLICATIONS

Clark, Ted, "Pathology of the Postweaning Multisystemic Wastings Syndrome in Pigs." Proceedings of the Western Canadian Association of Swine Practitioners, 1996 Annual Meeting, Oct. 1996, pp. 22-25.
Csank et al., "Dynamics of antibody response and viraemia following natural infection of porcine circovirus 2 (PCV-2) in a conentional pig herd." Acta Pathologica, Microbiologica and Immunologica Scandinavica, vol. 121, 2012, pp. 1207-1213.
Cutts et al., "Immunogenicity of high-titre AIK-C or Edmonston-Zagreb vaccines in 3.5-month-old infants, and of medium- or high-titre Edmonston-Zagreb vaccine in 6-month-old infants, in Kinshasa, Zaire." Vaccine, vol. 12, No. 14, 1994, pp. 1311-1316.
Czermak et al., "Membrane Filtration in Animal Cell Cutlure". 2007, Methods in Biotechnology, vol. 24, pp. 397-420, Humana Press, New Jersey, USA.
Darwich et al., "Cytokine profiles of peripheral blood mononuclear cells from pigs with postweaning multisystemic wasting syndrome in response to mitogen, superantigen or recall viral antigens". 2003, Journal of General Virology, vol. 84, pp. 3453-3457.
Dawson et al., "Studies of the field efficacy and safety of a single-dose Mycoplasma hyopneumoniae vaccine for pigs". Veterinary Record, vol. 151, 2002, pp. 535-538.
Dehaven, W. Ron, "Veterinary Services Memorandum No. 800.202." CVB General Licensing Considerations: Efficacy Stupies, Jun. 14, 2002, pp. 1-8.
Desrosiers et al., "Preliminary results with Ingelvac® CircoFLEX™ to protect multiple ages of Quebec Pigs against PCVAD." American Association of Swine Veterinarians, 2007, pp. 143-145.
Diamantstein et al., "Stimulation of humoral antibody formation by polyanions: I. The effect of polyacrylic acid on the primary immune response in mice immunized with sheep red blood cells." European Journal of Immunology, vol. 1, 1971, pp. 335-340.
Draganoiu et al., "Carbomer." Feb. 2009, pp. 110-114. [Retrieved at: http://drugs-nutrition.com/download/Handbook_of_excipients_6/Carbober.pdf on Sep. 23, 2015.].
Duarte et al., "Concomitant Zearalenone Ingestion and Porcine Circovirus-2 Infection". Acta Scientiae Veterinariae, vol. 41, Suppl. 1, Publication 37, 2013, pp. 1-6.
Dugdale et al., "Immune Response". Medline Plus Medicial Encyclopedia, Updated May 30, 2012, pp. 1-4. [Accessed at http://www.nlm.nih.gov/medlineplus/cncy/article/000821.htm on Mar. 19, 2014].
Eddicks et al., "Low prevalence of porcine circovirus type 2 infections in farrowing sows and corresponding pre-suckling piglets in southern German pig farms." Veterinary Microbiology, vol. 187, 2016, pp. 70-74.
Eichmeyer et al., "Evaluation of Ingelvac® 3FLEX: Demonstration of efficacy for the mixture of Ingelvac® PRRS MLV when rehydrated with Ingelvac CircoFLEX® and Ingelvac MycoFLEX®". 2010 American Association of Swine Veterinarians Annual Conference, Mar. 6-9, 2010, pp. 1-5.
Eichmeyer, Marc, "Annex 1 of PCV-2 Study" Jan. 2012, pp. 1-2.
Eichmeyer, Marc, "Efficacy of a PCV-2 Antigen in a Combination Vaccne." Boehringer Ingelheim Vetmedica, Inc., Study No. 6131-0981-05P-022, PCV2 Combination Efficacy Study, Aug. 19, 2010, pp. 1-3.
Eichmeyer, Marc, "Efficacy of PPRS Antigen in a Combination Vaccne." Boehringer Ingelheim Vetmedica, Inc., Study No. 6131-0852-06P-072, Ingelvac® PRRS MLV Combination Vaccine Efficacy Study, Aug. 19, 2010, pp. 1-4.
Eichmeyer, Marc, "PCV-2 Study." Boehringer Ingelheim Vetmedica, Inc., Jan. 2012, pp. 1-4.
Eichmeyer, Marc, "Summary of Study No. 6127-0981-08P-044 (Efficacy Study)" Boehringer Ingelheim Vetmedica, Inc., Mar. 11, 2010, pp. 1-2.
Eichmeyer, Marc, "Summary of Study No. 6131-0981-04P-047 (Overdose Study)" Boehringer Ingelheim Vetmedmica, Inc., Mar. 11, 2010, pp. 1-2.
Eisele, Simon, "Determination of the efficacy of an inactivated one-shot vaccine in piglets during the first or third week of life with Porcilis® PCV." Inaugural Dissertation for the Obstetrics of Veterinary Medicine at the Faculty of Veterinary Medicine, Ludwig-Maximilians-Universitat Munchen, Jul. 17, 2009. (Summary in English beginning at p. 69), pp. 1-88.
Ellis et al., "Lack of antibodies to porcine circovirus type 2 virus in beef and dairy cattle and horses in western Canada". Canadian Veterinary Journal, vol. 42, 2001, pp. 461-464.
Ellis et al., "Porcine circovirus-2 and concurrent infections in the field". Veterinary Microbiology, vol. 98, No. 2, Feb. 2004, pp. 159-163.
Ellis, John A., "Porcine circovirus: An old virus in a new guise causes an emerging disease thorugh a novel pathogenesis". Large Animal Veterinary Rounds, vol. 3, No. 4, Apr. 2003, pp. 1-6.
EMBL Acession No. ACA49861, Wang et al., "Porcine circovirus-2 capside protein"., Mar. 5, 2008, 1 page.
EMBL Acession No. ACA49867, Wang et al., "Porcine circovirus-2 capside protein"., Mar. 5, 2008, 1 page.
EMBL Acession No. ACV53224, Cortey et al., "Porcine circovirus-2 partial capsid protein"., Sep. 13, 2009, 1 page.
European Medical Agency, "Annex I: Summary of Product Characteristics: Suvaxyn PCV Suspension for injection for pigs". EPAR Product Information, Last Updated Jun. 4, 2017, pp. 1-22. [Accessed at: http://www.ema.europa.eu/docs/en_GB/document_library/EPAR_-_Product_Information/veterinary/000149/WC500069200.pdf].
European Medicines Agency, "I. Background information on the Procedure." 2008, 2 pages. [Accessed at: http://www.ema.europa.eu/docs/en_GB/document_library/EPAR_-_Procedural_steps_taken_before_authorisation/veterinary/000126/WC500062386.pdf].
European Medicines Agency, "Ingelvac CircoFLEX: Procedureal steps taken and scientific information after the authorisation." 2015, pp. 1-3. [http://www.ema.europa.eu/docs/en_GB/document_library/EPAR_-Procedural_steps_taken_and_scientific_information_after_authorisation/veterinary/000126/WC500062387.pdf].
European Medicines Agency, "Scientific Discussion." 2008, pp. 1-18. [Accessed at: http://www.ema.europa.eu/docs/en_GB/document_library/EPAR_-_Scientific_Discussion/veterinary/000126/WC500062385.pdf].
Fablet et al., "A Case Study of Neonatal Diarrhoea in a Farrow-to-Finish Pig Farm". International Society for Animal Hygiene, Saint Malo, 2004, p. 151.
Fachinger et al., "The effect of vaccination against porcine circovirus type 2 in pigs suffering from porcine respiratory disease complex". 2008, Vaccine, vol. 26, pp. 1488-1499.
Fan et al., "Baculovirus-Insect Expression and Immunological Studies of Porcin Circovirus Type 2 (PCV2) Capsid Protein". Proceedings of the 2nd Asian Pig Veterinary Society Congress, Sep. 19-21, 2005, Philippines, pp. 186-188.
Fan et al., "Immunogenicity of Empty Capsids of Porcine Circovirus Type 2 Produced in Insect Cells". 2007, Veterinary Research Communications, vol. 31, pp. 487-496.
Fan et al., "Preclinical study of influenza virus A M2 peptide conjugate vaccines in mice, ferrets, and rhesus monkeys". Vaccine, vol. 22, 2004, pp. 2993-3003.
Fan et al., "The Expression of Porcine Circovirus Type 2 ORF2 Gene in Insect Cells and its Character". Chinese Journal of Biotechnology, vol. 21, No. 6, Nov. 2005, pp. 975-978.
Fenaux et al., "A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Imunity Against PCV2 Infection in Pigs", J. Virol, Jun. 2004, vol. 78, No. 12, pp. 6297-6303.
Fenaux et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2". Journal of Clinical Microbiology, vol. 38, No. 7, Jul. 2000, pp. 2494-2503.
Fenaux et al., "Immunogenicity and Pathogenicity of Chimeric Infectious DNA Clones of Pathogenic Porcine Circovirus Type 2 (PCV2) and Nonpathogenic PCV1 in Weanling Pigs". Journal of Virology, vol. 77, No. 20, Oct. 2003, pp. 11232-11243.

(56) References Cited

OTHER PUBLICATIONS

"5.2.9 Evaluation of Saftey of Each Batch of Veterinary Vaccines and Immunosera." European Pharmacopoeia, 5th Edition, Strasbourg: Council of Europe, 2005, pp. 2829-2830.

"Calendar, Mar. 2007". 3rd Annual Pig Veterinary Society Congress, vol. 37, No. 2, 2007, p. 33. [Accessed at http://www.piginternational-digital.com/piginternational/2007013//Print . . . on Aug. 3, 2012].

"Directive 2001/82/EC of the European Parliament and of the Council of Nov. 6, 2001 on the Community code relating to veterinary medicinal products." Official Journal of the European Communities, L 311, Nov. 2001, pp. 1-66.

"General Methods 6xHis and GST Purification Direct Cloning". Baculovirus Expression Vector System Manual, 6th Edition, May 1999, pp. 1-108.

"H-V11-Postweaning multisystemic wasting syndrome—Lymph node—Pig". Read-Only Case Details Reviews: Mar. 2009, pp.1-4. [Accessed at http://www.askjpc.org/vspo/show_page.php?id=800 on Dec. 14, 2013].

"Killed vs. Modified Live Vaccines." DVMvac.org, 2006, pp. 1-3. [Accessed at http://dvmvac.org/killvmodified.asp on Oct. 10, 2017.].

"Reflection paper on the demonstration of a possible impact of maternally derived antibodies on vaccine efficacy in young animals." Europan Medicines Agency: Science Medicines Health, Mar. 15, 2010, pp. 1-5.

9 C.F.R. Ch. 1 (Jan. 1, 2006 Edition) §112.7(f), Animal and Plant Health Inspection Service, USDA, 1 page.

9 C.F.R. § 113.35 (2010).

Abstract in English of CN1458167, dated Nov. 26, 2003.

Albina et al., "An Experimental Model for Post-weaning Multisystenic Wasting Syndrome (PMWS) in Growing Piglets". 2001, Journal of Comparative Pathology, vol. 123, pp. 292-303.

Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.

Allan et al., "Letters, Immunostiulations, PCV-2 and PMWS", The Vet. Records, Aug. 5, 2000, pp. 170-171.

Allan et al., "Neonatal Vaccination for Mycoplasma Hyopneumoniae and Post-Weaning Multisystemic Wasting Syndrome: A Field Trial." The Pig Journal, vol. 48, 2001, pp. 34-41.

Allan et al., "Passive Transfer of Maternal Antibodies to PCV2 Protects Against Development of Post-weaning Multisystemic Wasting Syndrome (PMWS): Experiemental Infections and a Field Study". 2002, The Pig Journal, vol. 50, pp. 59-67.

Allan et al., "PCV2; ticking time bomb?" Pig Progress, vol. 18, No. 5, 2002, pp. 14-15.

Allan et al., "PMWS/PCVD: Diagnosis, Disease, and Control: What do we know?" 2006, Proceedings of the 19th IPVS Congress, Copenhagen, Denmark, vol. 1, pp. 1-9.

Allan et al., "Porcine Circoviruses; A Review", J. Vet., Diagn. Invest. 2000, 12, pp. 3-14.

Allan et al., "Reproduction of postweaning multisystemic wasting syndrome in pigs experimentally inoculated with a Swedish porcine circovirus 2 isolate". 2003, Journal of Veterinary Diagnostic Investigation, vol. 15, pp. 553-560.

Allan et al., Guest Editorial, "PCV-2 Infection in Swine; More Than Just Postweaning Multisystemic Wasting Syndrome", The Vet Journ., 2003, 166, pp. 222-223.

Bachmann et al., "The influence of virus structure on antibody responses and virus serotype formation". Immunology Today, vol. 17, No. 12, Dec. 1996, pp. 553-558.

Bahnemann, Hans G., "Inactivation of Viruses in Serum with Binary Ethyleneimine". Journal of Clinical Microbiology, vol. 3, No. 2, Feb. 1976, pp. 209-210.

Bandrick et al., "Colostral antibody-mediated and cell-mediated immunity contributes to innate and antigen-specific immunity in piglets." Developmental and Comparative Immunology, vol. 43, 2014, pp. 114-120.

Banholzer, E. "A Follow-Up: PCV2, PRRS, Mycoplasma hyopneumoniae, Improvac". IPVS Congress, Jul. 16-19, 2006, pp. 1-20.

Bassaganya-Riera et al., "Conjugated Linoleic Acid Ameliorates Viral Infectivity in a Pig Model of Virally Induced Immunosuppression". 2003, American Society for Nutritional Sciences, pp. 3204-3214.

Beach et al., "Efficacy and future prospects of commercially available and experimental vaccines against porcine circovirus type 2 (PCV2)". Virus Research, vol. 164, 2012, pp. 33-42.

Beach et al., "Novel chimeric porcine circovirus (PCV) with the capsid gene of the emerging PCV2b subtype cloned in the genomic bacbone of the non-pathogenic PCV1 is attenuated in vivo and induces protective and cross-protective immunity against PCV2b and PCV2a subtypes in pigs". Vaccine, vol. 29, 2011, pp. 221-232.

Begue et al., "Future Combined Vaccines". Journal of Infectious Diseases, vol. 173, Supp 3, 1996, pp. S295-S297.

Berinstein et al., "Mucosal and systemic immunization elicited by Newcastle disease virus (NDV) transgenic plants as antigens." Vaccine, vol. 23, 2005, pp. 5583-5589.

Beseme et al., "Vaccination strategies for the control of circoviral diseases in pigs: PMWS and PCV2-associated PRDC". Proceedings of the Japanese Pig Veterinary Society, vol. 49, 2006, pp. 15-38.

Blanchard et al., "An ORF2 protein-based ELISA for porcine circovirus type 2 antibodies in post-weaning multisystemic wasting syndrome". Veterinary Microbiology, vol. 94, 2003, pp. 183-194.

Blanchard et al., "Protection of swine against post-weaning multisystemic wasting syndrome (PMWS) by porcine circovirus type 2 (PCV2) proteins". Vaccine, vol. 21, 2003, pp. 4565-4575.

Boehringer Ingelheim Vetmedica GmbH, "Our conviction regarding PRRS—only facts count!" Oct. 2003, pp. 1-3.

Boehringer Ingelheim Vetmedica, Inc. "Ingelvac® CircoFLEX™ Symposium." Sep. 15, 2007, St. Paul, Minnesota, pp. 1-8. [Accessed at http://animal-health-online.de/circovirus_01/docs/leman_circo.pdf].

Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb. 2008, Technical Bulletin, www.bi-vetmedica.com/swine-research/MycoFLEX-Mycoplasma-immunity_TB2.pdf; 14 pages.

Boehringer Ingelheim Vetmedica, Inc., "Ingelvacâ Circoflexä Safety Data Sheet" Apr. 27, 2015, pp. 1-6.

Boehringer Ingelheim Vetmedica, Inc., "ReproCyc® PRRS-PLE", 2011, p. 1. [Accessed at: http://bi-vetmedica.com/product/reprocyc-prrs-ple on Apr. 12, 2011].

Boehringer Ingelheim, "Preventing disease: One billion pigs vaccinated with Ingelvac CircoFLEX®" Feb. 14, 2013, pp. 1-3. [Available at: https://www.boehringer-ingelheim.com/press-release/preventing-disease-one-billion-pigs-vaccinated-ingelvac-circoflex].

Boga et al., "A single dose immunization with rabbit haemorrhagic disease virus major capsid protein produced in *Saccharomyces cerevisiae* induces protection". Journal of General Virology, vol. 78, 1997, pp. 2315-2318.

Boisgerault et al., "Virus-like particles: a new family of delivery systems". Expert Review of Vaccines, vol. 1, No. 1, Jun. 2002, pp. 101-109.

Boisseson et al., "Molecular characterization of Porcine circovirus type 2 isolates from post-weaning multisystemic wasting syndrome-affected and non-affected pigs". 2004, Journal of General Virology, vol. 85, pp. 293-304.

Bolin et al., "Postweaning multisystemic wasting syndrome induced after experimental inoculation of cesarean-derived, colostrum-deprived piglets with type 2 porcine circovirus". 2001, Journal of Veterinary Diagnostice Investigation, vol. 13, pp. 185-194.

Bowie, et al., "Deciphering the Message in Protein Sequences: Tolerance to Amino Acid Substitutions," Science, vol. 247, 1990, pp. 1306-1310.

Bretey et al., "Performance benefits resulting from vaccination with Ingelvac CircoFLEX and/or Ingelvac PRRS MLV." Leman Swine Conference 2009, 1 page.

(56) References Cited

OTHER PUBLICATIONS

Brockmeier et al., "Porcine Respiratory Disease Complex." Polymicrobial Diseases, Washington (DC), ASM Press; 2002, Chapter 13, pp. 1-25. [Accessed at https://www.ncbi.nlm.nih.gov/books/NBK2481/].

Brogden, Kim A., "Polymicrobial Diseases of Animals and Humans". Polymicrobial Diseases, Chapter 1, 2002, 19 pages. [Accessed at http://www.ncbi.nlm.nih.gov/books/NBK2477/?report=printable on Jul. 8, 2014].

Bunn, Thomas O., "Vaccine Adjuvants and Carriers." Vaccines for Veterinary Applications, Oxford, Boston, Butterworth-Heinemann, 1993, pp. 295-302.

Cameo "Carbopol®". Wikipedia, The Free Encyclopedia, Jul. 24, 2013, at 06:59, pp. 1-2 [Accessed at https://http://cameo.mfa.org/index.php?title=Carbopol®&oldid=22637on Sep. 23, 2015.].

Caprioli et al., "PCR detection of porcine circovirus type 2 (PCV2) DNA in blood, tonsillar and faecal swabs from experimentally infected pigs". Research in Veterinary Sciences, vol. 81, No. 2, Oct. 2006, pp. 287-292.

Cariolet et al., "Rappel Des Différentes Méthodes D'Obtention de Porcelets Assainis: Conditions de Maintien Du Statut Sanitaire et Valorisation de ces Animaux." Journées Rech. Porcine en France, vol. 26, 1994, pp. 1-12. (Abstract in English on p. 1).

\* cited by examiner

FIG. 1

| Position | 2a | 2b |
|---|---|---|
| 59 | A | R/K |
| 63 | T | R/K |
| 88 | K | P |
| 151 | P | T |
| 191 | R | G |
| 206 | K | I |
| 232 | E | N |

Swine α-PCV2b IgG

SDS-PAGE

PCV2b ORF2 VLPs

PCV2a ORF2 VLPs

FIG. 6

| Construct | EM VLP Confirmation | VLP Yield at 1L Scale |
|---|---|---|
| ORF2a | Y | 5.5mg/L |
| ORF2b BDH | | |
| ORF2b BDH SFCO | Y | 0.4mg/L |
| ORF2b BDH K59A | Y | 0.34mg/L |
| ORF BDH R63K | | |
| ORF2b BDH R63T | Y | 3.2mg/L |
| ORF2b BDH SFCO P88K T151P | ** | ** |
| ORF2b BDH G191R | N | N/A |
| ORF2b BDH N232E | Y | 0.57mg/L |
| ORF2b BDH I206K | N | N/A |

FIG. 7A

| Construct | Concentration (µg/mL) |
|---|---|
| BaculoG/ORF2a | 5.5 |
| BaculoG/ORF2b BDH | 0.39 |
| BaculoG/ORF2b BDH R63L | 3.57 |
| BaculoG/ORF2b BDH R63G | 4.14 |
| BaculoG/ORF2b BDH R63Q | 5.31 |
| BaculoG/ORF2b BDH R63T | 7.06 |
| BaculoG/ORF2b BDH R63D | 1.71 |

FIG. 7B

SEQUENCE LISTING

```
<160> NUMBER OF SEQ ID NOS: 46

<210> SEQ ID NO 1
<211> LENGTH: 234
<212> TYPE: PRT
<213> ORGANISM: Artificial Sequence
<220> FEATURE:
<223> OTHER INFORMATION: corresponds to SEQ ID NO:2 with the
      substitution R63T

<400> SEQUENCE: 1

Met Thr Tyr Pro Arg Arg Arg Phe Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
                35                  40                  45

Leu Ser Arg Thr Ile Gly Tyr Thr Val Lys Lys Thr Thr Val Thr Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 2
<211> LENGTH: 234
<212> TYPE: PRT
<213> ORGANISM: Porcine circovirus

<400> SEQUENCE: 2

Met Thr Tyr Pro Arg Arg Arg Phe Arg Arg Arg His Arg Pro Arg
1               5                   10                  15
```

Ser His Leu Gly Gln Ile Leu Arg Arg Pro Trp Leu Val His Pro
         20                  25                  30

Arg His Arg Tyr Arg Trp Arg Arg Lys Asn Gly Ile Phe Asn Thr Arg
             35                  40                  45

Leu Ser Arg Thr Ile Gly Tyr Thr Val Lys Lys Thr Thr Val Arg Thr
 50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
             85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
            195                 200                 205

Gln Asp Tyr Asn Ile Arg Ile Thr Met Tyr Val Gln Phe Arg Glu Phe
210                 215                 220

Asn Leu Lys Asp Pro Pro Leu Asn Pro Lys
225                 230

<210> SEQ ID NO 3
<211> LENGTH: 233
<212> TYPE: PRT
<213> ORGANISM: Porcine circovirus

<400> SEQUENCE: 3

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
20 25 30

Arg His Arg Tyr Arg Trp Arg Arg Lys Asn Gly Ile Phe Asn Thr Arg
35 40 45

Leu Ser Arg Thr Phe Gly Tyr Thr Val Lys Ala Thr Thr Val Thr Thr
50 55 60

Pro Ser Trp Ala Val Asp Met Met Arg Phe Asn Ile Asp Asp Phe Val
65 70 75 80

Pro Pro Gly Gly Gly Thr Asn Lys Ile Ser Ile Pro Phe Glu Tyr Tyr
85 90 95

Arg Ile Arg Lys Val Lys Val Glu Phe Trp Pro Cys Ser Pro Ile Thr
100 105 110

Gln Gly Asp Arg Gly Val Gly Ser Thr Ala Val Ile Leu Asp Asp Asn
115 120 125

Phe Val Thr Lys Ala Thr Ala Leu Thr Tyr Asp Pro Tyr Val Asn Tyr
130 135 140

Ser Ser Arg His Thr Ile Pro Gln Pro Phe Ser Tyr His Ser Arg Tyr
145 150 155 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230

<210> SEQ ID NO 4
<211> LENGTH: 705
<212> TYPE: DNA
<213> ORGANISM: Artificial Sequence
<220> FEATURE:
<223> OTHER INFORMATION: encodes SEQ ID NO:1
<220> FEATURE:
<221> NAME/KEY: misc_feature
<222> LOCATION: (187)..(189)

<400> SEQUENCE: 4
atgacgtatc caaggaggcg tttccgcaga cgaagacacc gcccccgcag ccatcttggc      60
cagatcctcc gccgccgccc ctggctcgtc caccccgcc accgttaccg ctggagaagg      120
aaaaatggca tcttcaacac ccgcctctcc cgcaccatcg gttatactgt caagaaaacc     180
acagtcacaa cgcccctcctg gaatgtggac atgatgagat taatattaa tgattttctt    240 cccccaggag ggggctcaaa ccccctcact gtgccctttg aatactacag aataaggaag    300
gttaaggttg agttctggcc ctgctcccca atcacccagg gtgacagggg agtgggctcc    360
actgctgtta ttctagatga taactttgta acaaaggcca atgccctaac ctatgacccc    420
tatgtaaact actcctcccg ccataccata cccagccct tctcctacca ctcccggtac     480
tttaccccga aacctgtcct tgataggaca atcgattact ccaacccaa taacaaaaga     540 aatcaactct ggctgagact acaaactact ggaaatgtag accatgtagg cctcggcact    600
gcgttcgaaa acagtatata cgaccaggac tacaatatcc gtaaccat gtatgtacaa     660 ttcagagaat ttaatcttaa agaccccca cttaaccta agtga              705

<210> SEQ ID NO 5
<211> LENGTH: 233
<212> TYPE: PRT
<213> ORGANISM: Porcine circovirus

<400> SEQUENCE: 5

Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Ile Lys Arg Thr Thr Val Arg Thr
    50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Arg Ser Val Pro Phe Glu Tyr Tyr
                85                  90                  95

-continued

```
Arg Ile Arg Lys Val Lys Val Glu Phe Trp Pro Cys Ser Pro Ile Thr
            100                 105                 110

Gln Gly Asp Arg Gly Val Gly Ser Ser Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
        195                 200                 205

Gln Glu Tyr Asn Ile Arg Val Thr Met Tyr Val Gln Phe Arg Glu Phe
    210                 215                 220

Asn Leu Lys Asp Pro Pro Leu Asn Pro
225                 230
```

<210> SEQ ID NO 6
<211> LENGTH: 233
<212> TYPE: PRT
<213> ORGANISM: Porcine circovirus
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: MISC_FEATURE
<222> LOCATION: (63)..(63)
<223> OTHER INFORMATION: Xaa at position 63 is selected from the group
      consisting of Ala, Asn, Asp, Cys, Glu, Gln, Gly, His, Ile, Leu,
      Met, Phe, Pro, Ser, Thr, Trp, Tyr, and Val.
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: MISC_FEATURE
<222> LOCATION: (210)..(210)
<223> OTHER INFORMATION: Xaa at position 210 is selected from the group
      consisting of Asp and Glu.

```
<220> FEATURE:
<221> NAME/KEY: misc_feature
<222> LOCATION: (215)..(215)
<223> OTHER INFORMATION: Xaa can be any naturally occurring amino acid

<400> SEQUENCE: 6
```

Met Thr Tyr Pro Arg Arg Xaa Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
            35                  40                  45

Leu Ser Arg Thr Xaa Gly Tyr Thr Xaa Lys Arg Thr Thr Val Xaa Thr
    50                  55                  60

Pro Ser Trp Xaa Val Asp Met Met Arg Phe Asn Ile Asn Asp Phe Leu
65              70                  75                  80

Pro Pro Gly Gly Gly Ser Asn Pro Xaa Xaa Val Pro Phe Glu Tyr Tyr
            85                  90                  95

Arg Ile Arg Lys Val Lys Val Glu Phe Trp Pro Cys Ser Pro Ile Thr
            100                 105                 110

Gln Gly Asp Arg Gly Val Gly Ser Xaa Ala Val Ile Leu Asp Asp Asn
            115                 120                 125

Phe Val Thr Lys Ala Xaa Ala Leu Thr Tyr Asp Pro Tyr Val Asn Tyr
130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Xaa Thr Ile Asp Tyr Phe Gln Pro
            165                 170                 175

Asn Asn Lys Arg Asn Gln Leu Trp Leu Arg Leu Gln Thr Xaa Gly Asn
            180                 185                 190

Val Asp His Val Gly Leu Gly Thr Ala Phe Glu Asn Ser Ile Tyr Asp
            195                 200                 205

Gln Xaa Tyr Asn Ile Arg Xaa Thr Met Tyr Val Gln Phe Arg Glu Phe
    210                 215                 220

Asn Leu Lys Asp Pro Pro Leu Asn Pro
225                 230

```
<210> SEQ ID NO 7
<211> LENGTH: 233
<212> TYPE: PRT
<213> ORGANISM: Porcine circovirus
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: MISC_FEATURE
<222> LOCATION: (63)..(63)
<223> OTHER INFORMATION: Xaa at position 63 is selected from the group
      consisting of Ala, Asn, Asp, Cys, Glu, Gln, Gly, His, Ile, Leu,
      Met, Phe, Pro, Ser, Thr, Trp, Tyr, and Val.
<220> FEATURE:
<221> NAME/KEY: misc_feature
<222> LOCATION: (68)..(68)
<223> OTHER INFORMATION: Xaa can be any naturally occurring amino acid
```

```
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: MISC_FEATURE
<222> LOCATION: (210)..(210)
<223> OTHER INFORMATION: Xaa at position 210 is selected from the group
      consisting of Asp and Glu.
<220> FEATURE:
<221> NAME/KEY: misc_feature
<222> LOCATION: (215)..(215)
<223> OTHER INFORMATION: Xaa can be any naturally occurring amino acid

<400> SEQUENCE: 7

Met Thr Tyr Pro Arg Arg Xaa Arg Arg Arg His Arg Pro Arg
1               5                  10                  15

Ser His Leu Gly Gln Ile Leu Arg Arg Pro Trp Leu Val His Pro
                20                  25                  30

Arg His Arg Tyr Arg Trp Arg Arg Lys Asn Gly Ile Phe Asn Thr Arg
        35                  40                  45

Leu Ser Arg Thr Xaa Gly Tyr Thr Xaa Lys Lys Thr Thr Val Xaa Thr
    50                  55                  60

Pro Ser Trp Xaa Val Asp Met Met Arg Phe Asn Ile Asn Asp Phe Leu
65                  70                  75                  80

Pro Pro Gly Gly Gly Ser Asn Pro Xaa Xaa Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Xaa Ala Val Ile Leu Asp Asp Asn
        115                 120                 125

Phe Val Thr Lys Ala Xaa Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Xaa Thr Ile Asp Tyr Phe Gln Pro
                165                 170                 175

Asn Asn Lys Arg Asn Gln Leu Trp Leu Arg Leu Gln Thr Xaa Gly Asn
            180                 185                 190

Val Asp His Val Gly Leu Gly Thr Ala Phe Glu Asn Ser Ile Tyr Asp
        195                 200                 205

Gln Xaa Tyr Asn Ile Arg Xaa Thr Met Tyr Val Gln Phe Arg Glu Phe
    210                 215                 220

Asn Leu Lys Asp Pro Pro Leu Asn Pro
225                 230

<210> SEQ ID NO 8
```

```
<211> LENGTH: 234
<212> TYPE: PRT
<213> ORGANISM: Porcine circovirus
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: MISC_FEATURE
<222> LOCATION: (63)..(63)
<223> OTHER INFORMATION: Xaa at position 63 is selected from the group
      consisting of Ala, Asn, Asp, Cys, Glu, Gln, Gly, His, Ile, Leu,
      Met, Phe, Pro, Ser, Thr, Trp, Tyr, and Val.
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: MISC_FEATURE
<222> LOCATION: (210)..(210)
<223> OTHER INFORMATION: Xaa at position 210 is selected from the group
      consisting of Asp and Glu.
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid

<400> SEQUENCE: 8

Met Thr Tyr Pro Arg Arg Arg Xaa Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Xaa Gly Tyr Thr Xaa Lys Arg Thr Thr Val Xaa Thr
    50                  55                  60

Pro Ser Trp Xaa Val Asp Met Met Arg Phe Asn Ile Asn Asp Phe Leu
65                  70                  75                  80

Pro Pro Gly Gly Gly Ser Asn Pro Xaa Xaa Val Pro Phe Glu Tyr Tyr
                85                  90                  95
```

```
Arg Ile Arg Lys Val Lys Val Glu Phe Trp Pro Cys Ser Pro Ile Thr
                100                 105                 110

Gln Gly Asp Arg Gly Val Gly Ser Xaa Ala Val Ile Leu Asp Asp Asn
        115                 120                 125

Phe Val Thr Lys Ala Xaa Ala Leu Thr Tyr Asp Pro Tyr Val Asn Tyr
        130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Xaa Thr Ile Asp Tyr Phe Gln Pro
                165                 170                 175

Asn Asn Lys Arg Asn Gln Leu Trp Leu Arg Leu Gln Thr Xaa Gly Asn
            180                 185                 190

Val Asp His Val Gly Leu Gly Thr Ala Phe Glu Asn Ser Ile Tyr Asp
        195                 200                 205

Gln Xaa Tyr Asn Ile Arg Xaa Thr Met Tyr Val Gln Phe Arg Glu Phe
    210                 215                 220

Asn Leu Lys Asp Pro Pro Leu Asn Pro Xaa
225                 230

<210> SEQ ID NO 9
<211> LENGTH: 234
<212> TYPE: PRT
<213> ORGANISM: Porcine circovirus
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: MISC_FEATURE
<222> LOCATION: (63)..(63)
<223> OTHER INFORMATION: Xaa at position 63 is selected from the group
      consisting of Ala, Asn, Asp, Cys, Glu, Gln, Gly, His, Ile, Leu,
      Met, Phe, Pro, Ser, Thr, Trp, Tyr, and Val.
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: MISC_FEATURE
<222> LOCATION: (210)..(210)
<223> OTHER INFORMATION: Xaa at position 210 is selected from the group
      consisting of Asp and Glu.
```

```
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid

<400> SEQUENCE: 9
```

Met Thr Tyr Pro Arg Arg Xaa Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Xaa Gly Tyr Thr Xaa Lys Lys Thr Thr Val Xaa Thr
    50                  55                  60

Pro Ser Trp Xaa Val Asp Met Met Arg Phe Asn Ile Asn Asp Phe Leu
65              70                  75                  80

Pro Pro Gly Gly Gly Ser Asn Pro Xaa Xaa Val Pro Phe Glu Tyr Tyr
            85                  90                  95

Arg Ile Arg Lys Val Lys Val Glu Phe Trp Pro Cys Ser Pro Ile Thr
        100                 105                 110

Gln Gly Asp Arg Gly Val Gly Ser Xaa Ala Val Ile Leu Asp Asp Asn
    115                 120                 125

Phe Val Thr Lys Ala Xaa Ala Leu Thr Tyr Asp Pro Tyr Val Asn Tyr
130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Xaa Thr Ile Asp Tyr Phe Gln Pro
                165                 170                 175

Asn Asn Lys Arg Asn Gln Leu Trp Leu Arg Leu Gln Thr Xaa Gly Asn
            180                 185                 190

Val Asp His Val Gly Leu Gly Thr Ala Phe Glu Asn Ser Ile Tyr Asp
        195                 200                 205

Gln Xaa Tyr Asn Ile Arg Xaa Thr Met Tyr Val Gln Phe Arg Glu Phe
    210                 215                 220

Asn Leu Lys Asp Pro Pro Leu Asn Pro Xaa
225                 230

```
<210> SEQ ID NO 10
<211> LENGTH: 9
<212> TYPE: PRT
<213> ORGANISM: Porcine circovirus

<400> SEQUENCE: 10
```

Lys Arg Thr Thr Val Ala Thr Pro Ser
1               5

```
<210> SEQ ID NO 11
<211> LENGTH: 9
<212> TYPE: PRT
<213> ORGANISM: Porcine circovirus

<400> SEQUENCE: 11
```

Lys Arg Thr Thr Val Cys Thr Pro Ser
1               5

```
<210> SEQ ID NO 12
<211> LENGTH: 9
<212> TYPE: PRT
<213> ORGANISM: Porcine circovirus

<400> SEQUENCE: 12

Lys Arg Thr Thr Val Asp Thr Pro Ser
1               5

<210> SEQ ID NO 13
<211> LENGTH: 9
<212> TYPE: PRT
<213> ORGANISM: Porcine circovirus

<400> SEQUENCE: 13

Lys Arg Thr Thr Val Glu Thr Pro Ser
1               5

<210> SEQ ID NO 14
<211> LENGTH: 9
<212> TYPE: PRT
<213> ORGANISM: Porcine circovirus

<400> SEQUENCE: 14

Lys Arg Thr Thr Val Phe Thr Pro Ser
1               5

<210> SEQ ID NO 15
<211> LENGTH: 9
<212> TYPE: PRT
<213> ORGANISM: Porcine circovirus

<400> SEQUENCE: 15

Lys Arg Thr Thr Val Gly Thr Pro Ser
1               5

<210> SEQ ID NO 16
<211> LENGTH: 9
<212> TYPE: PRT
<213> ORGANISM: Porcine circovirus

<400> SEQUENCE: 16

Lys Arg Thr Thr Val His Thr Pro Ser
1               5

<210> SEQ ID NO 17
<211> LENGTH: 9
<212> TYPE: PRT
<213> ORGANISM: Porcine circovirus

<400> SEQUENCE: 17

Lys Arg Thr Thr Val Ile Thr Pro Ser
1               5

<210> SEQ ID NO 18
<211> LENGTH: 9
<212> TYPE: PRT
<213> ORGANISM: Porcine circovirus

<400> SEQUENCE: 18

Lys Arg Thr Thr Val Leu Thr Pro Ser
1               5

<210> SEQ ID NO 19
<211> LENGTH: 9
```

```
<212> TYPE: PRT
<213> ORGANISM: Porcine circovirus

<400> SEQUENCE: 19

Lys Arg Thr Thr Val Met Thr Pro Ser
1               5

<210> SEQ ID NO 20
<211> LENGTH: 9
<212> TYPE: PRT
<213> ORGANISM: Porcine circovirus

<400> SEQUENCE: 20

Lys Arg Thr Thr Val Asn Thr Pro Ser
1               5

<210> SEQ ID NO 21
<211> LENGTH: 9
<212> TYPE: PRT
<213> ORGANISM: Porcine circovirus

<400> SEQUENCE: 21

Lys Arg Thr Thr Val Pro Thr Pro Ser
1               5

<210> SEQ ID NO 22
<211> LENGTH: 9
<212> TYPE: PRT
<213> ORGANISM: Porcine circovirus

<400> SEQUENCE: 22

Lys Arg Thr Thr Val Gln Thr Pro Ser
1               5

<210> SEQ ID NO 23
<211> LENGTH: 9
<212> TYPE: PRT
<213> ORGANISM: Porcine circovirus

<400> SEQUENCE: 23

Lys Arg Thr Thr Val Ser Thr Pro Ser
1               5

<210> SEQ ID NO 24
<211> LENGTH: 9
<212> TYPE: PRT
<213> ORGANISM: Porcine circovirus

<400> SEQUENCE: 24

Lys Arg Thr Thr Val Thr Thr Pro Ser
1               5

<210> SEQ ID NO 25
<211> LENGTH: 9
<212> TYPE: PRT
<213> ORGANISM: Porcine circovirus

<400> SEQUENCE: 25

Lys Arg Thr Thr Val Val Thr Pro Ser
1               5

<210> SEQ ID NO 26
<211> LENGTH: 9
<212> TYPE: PRT
<213> ORGANISM: Porcine circovirus
```

```
<400> SEQUENCE: 26

Lys Arg Thr Thr Val Trp Thr Pro Ser
1               5

<210> SEQ ID NO 27
<211> LENGTH: 9
<212> TYPE: PRT
<213> ORGANISM: Porcine circovirus

<400> SEQUENCE: 27

Lys Arg Thr Thr Val Tyr Thr Pro Ser
1               5

<210> SEQ ID NO 28
<211> LENGTH: 9
<212> TYPE: PRT
<213> ORGANISM: Porcine circovirus

<400> SEQUENCE: 28

Lys Lys Thr Thr Val Ala Thr Pro Ser
1               5

<210> SEQ ID NO 29
<211> LENGTH: 9
<212> TYPE: PRT
<213> ORGANISM: Porcine circovirus

<400> SEQUENCE: 29

Lys Lys Thr Thr Val Cys Thr Pro Ser
1               5

<210> SEQ ID NO 30
<211> LENGTH: 9
<212> TYPE: PRT
<213> ORGANISM: Porcine circovirus

<400> SEQUENCE: 30

Lys Lys Thr Thr Val Asp Thr Pro Ser
1               5

<210> SEQ ID NO 31
<211> LENGTH: 9
<212> TYPE: PRT
<213> ORGANISM: Porcine circovirus

<400> SEQUENCE: 31

Lys Lys Thr Thr Val Glu Thr Pro Ser
1               5

<210> SEQ ID NO 32
<211> LENGTH: 9
<212> TYPE: PRT
<213> ORGANISM: Porcine circovirus

<400> SEQUENCE: 32

Lys Lys Thr Thr Val Phe Thr Pro Ser
1               5

<210> SEQ ID NO 33
<211> LENGTH: 9
<212> TYPE: PRT
<213> ORGANISM: Porcine circovirus

<400> SEQUENCE: 33
```

-continued

```
Lys Lys Thr Thr Val Gly Thr Pro Ser
1               5

<210> SEQ ID NO 34
<211> LENGTH: 9
<212> TYPE: PRT
<213> ORGANISM: Porcine circovirus

<400> SEQUENCE: 34

Lys Lys Thr Thr Val His Thr Pro Ser
1               5

<210> SEQ ID NO 35
<211> LENGTH: 9
<212> TYPE: PRT
<213> ORGANISM: Porcine circovirus

<400> SEQUENCE: 35

Lys Lys Thr Thr Val Ile Thr Pro Ser
1               5

<210> SEQ ID NO 36
<211> LENGTH: 9
<212> TYPE: PRT
<213> ORGANISM: Porcine circovirus

<400> SEQUENCE: 36

Lys Lys Thr Thr Val Leu Thr Pro Ser
1               5

<210> SEQ ID NO 37
<211> LENGTH: 9
<212> TYPE: PRT
<213> ORGANISM: Porcine circovirus

<400> SEQUENCE: 37

Lys Lys Thr Thr Val Met Thr Pro Ser
1               5

<210> SEQ ID NO 38
<211> LENGTH: 9
<212> TYPE: PRT
<213> ORGANISM: Porcine circovirus

<400> SEQUENCE: 38

Lys Lys Thr Thr Val Asn Thr Pro Ser
1               5

<210> SEQ ID NO 39
<211> LENGTH: 9
<212> TYPE: PRT
<213> ORGANISM: Porcine circovirus

<400> SEQUENCE: 39

Lys Lys Thr Thr Val Pro Thr Pro Ser
1               5

<210> SEQ ID NO 40
<211> LENGTH: 9
<212> TYPE: PRT
<213> ORGANISM: Porcine circovirus

<400> SEQUENCE: 40

Lys Lys Thr Thr Val Gln Thr Pro Ser
```

```
1               5

<210> SEQ ID NO 41
<211> LENGTH: 9
<212> TYPE: PRT
<213> ORGANISM: Porcine circovirus

<400> SEQUENCE: 41

Lys Lys Thr Thr Val Ser Thr Pro Ser
1               5

<210> SEQ ID NO 42
<211> LENGTH: 9
<212> TYPE: PRT
<213> ORGANISM: Porcine circovirus

<400> SEQUENCE: 42

Lys Lys Thr Thr Val Thr Thr Pro Ser
1               5

<210> SEQ ID NO 43
<211> LENGTH: 9
<212> TYPE: PRT
<213> ORGANISM: Porcine circovirus

<400> SEQUENCE: 43

Lys Lys Thr Thr Val Val Thr Pro Ser
1               5

<210> SEQ ID NO 44
<211> LENGTH: 9
<212> TYPE: PRT
<213> ORGANISM: Porcine circovirus

<400> SEQUENCE: 44

Lys Lys Thr Thr Val Trp Thr Pro Ser
1               5

<210> SEQ ID NO 45
<211> LENGTH: 9
<212> TYPE: PRT
<213> ORGANISM: Porcine circovirus

<400> SEQUENCE: 45

Lys Lys Thr Thr Val Tyr Thr Pro Ser
1               5

<210> SEQ ID NO 46
<211> LENGTH: 234
<212> TYPE: PRT
<213> ORGANISM: Porcine circovirus
<220> FEATURE:
<221> NAME/KEY: MISC_FEATURE
<222> LOCATION: (63)..(63)
<223> OTHER INFORMATION: Xaa at position 63 is selected from the group
      consisting of Ala, Asn, Asp, Cys, Glu, Gln, Gly, His, Ile, Leu,
      Met, Phe, Pro, Ser, Thr, Trp, Tyr, and Val.

<400> SEQUENCE: 46

Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45
```

```
Leu Ser Arg Thr Ile Gly Tyr Thr Val Lys Lys Thr Thr Val Xaa Thr
    50              55                  60

Pro Ser Trp Asn Val Asp Met Met Arg Phe Asn Ile Asn Asp Phe Leu
65              70                  75                  80

Pro Pro Gly Gly Gly Ser Asn Pro Leu Thr Val Pro Phe Glu Tyr Tyr
            85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
            165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
        210                 215                 220

Asn Leu Lys Asp Pro Pro Leu Asn Pro Lys
225                 230
```

PCV2 ORF2 PROTEIN VARIANT AND VIRUS LIKE PARTICLES COMPOSED THEREOF

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV-1). However, in contrast with PCV1, which is generally non-virulent, swine infected with PCV2 exhibit a syndrome commonly referred to as Post-weaning Multi-systemic Wasting Syndrome (PMWS). PMWS is clinically characterized by wasting, paleness of the skin, unthriftiness, respiratory distress, diarrhea, icterus, and jaundice. In some affected swine, a combination of all signs will be apparent while other swine will only have one or two of these clinical signs. During necropsy, microscopic and macroscopic lesions also appear on multiple tissues and organs, with lymphoid organs being the most common site for lesions. A strong correlation has been observed between the amount of PCV2 nucleic acid or antigen and the severity of microscopic lymphoid lesions. Mortality rates for swine infected with PCV2 can approach 80%. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia.

Currently, there are three subtypes of PCV2 known (PCV2a, PCV2b and PCV2c), which are classified according to a unified nomenclature for PCV2 genotypes (Segales, J. et al., 2008, PCV-2 genotype definition and nomenclature, Vet Rec 162:867-8). Two further subtypes (PCV2d and PCV2e) have been proposed (Wang et al. Virus Res. 2009 145(1):151-6) but, however, it was demonstrated later that they belong to the PCV2a and PCV2b clusters (Cortey et al. Vet Microbiol. 2011 149(3-4):522-32011). According to this unified nomenclature for PCV2 genotypes the orf2 gene is used to perform genotyping for pcv-2, wherein the geotyping is based on the proportion of nucleotide sites at which two sequences being compared are different (p distance). This value is obtained by dividing the number of nucleotide differences by the total number of nucleotides compared (Kumar et al. 2001 Bioinformatics 17, 1244-1245) and subsequently, the construction of a p distance/frequency histogram enables to determine potential cut-off values to distinguish different genotypes (Rogers and Harpending 1992 Molecular Biology and Evolution 9, 552-569; Biagini et al. 1999 Journal of General Virology 80, 419-424). Using this methodology, orf2 pcv-2 sequences are assigned to different genotypes when the genetic distance between them is 0-035.

US 2011/0305725 A1 describes a study planned to test a new vaccine formulation in pigs to assess its efficacy against porcine circovirus and *M. hyopneumoniae*. During the course of this study, it was observed that several of the pigs in the control and vaccinated groups exhibited clinical signs of PMWS. It was then confirmed that these pigs were exposed to environmental PCV2 prior to challenge. Molecular analysis on blood and tissue samples from these pigs revealed that they harbored a type 2B strain that was different than the strain used for challenge (paragraph [0152] of US 2011/0305725 A1).

WO2011116094 A2 discloses a chimeric porcine circovirus infectious DNA clone and live attenuated chimeric virus with the PCV2 of subtype PCV2b, and a capsid gene of subtype PCV2b integrated into a non-pathogenic PCV1 virus genome, wherein the attenuated chimeric virus can be used as a live vaccine, as well as an inactivated (killed) vaccine.

WO2013030320 A1 relates to synthetic Circovirus type capsid proteins and to methods for treating and/or preventing PCV2-associated diseases in mammals using said proteins. Two sequences were designed according to WO2013030320 A1, wherein one sequence was modified further with, among others, the following optimizations:

A potential cleavage site was eliminated at amino acid position 165.
A mutation was introduced in position 200.
A replacement was made in position 161.
A replacement was made in position 170.
The S residue in position 225 was replaced with a D.
A replacement was made at position 143.
Two replacements were made at the N-terminal of the sequence (positions 13 and 20).

However, as in practice the expression of wild type PCV2b ORF2 protein is found to be insufficient and requires further concentration steps in order to receive virus like particles (VLPs) useful to prepare a subunit vaccine, an easy modification of naturally occurring PCV2b ORF2 protein sequences is needed for enhancing the expression efficacy and for increasing the production of VLPs, thereby allowing a fast and easy production of effective PCV2 subunit vaccines.

The solution to the above technical problem is achieved by the description and the embodiments characterized in the claims.

Thus, the invention in its different aspects is implemented according to the claims.

BRIEF DESCRIPTION OF THE DRAWINGS

FIG. 1—Major Amino Acid Changes Between PCV2a and PCV2b ORF2 Amino Acid Sequences.

FIG. 6—Results of PCV2b ORF2 mutant construct evaluation. SFCO=Codon optimized for *Spodoptera frugiperda*. The native PCV2b ORF2 BDH and R63K constructs were not checked for VLP or quantitated as the R63T construct was discovered at the same time.

FIGS. 7A and 7B—Results of PCV2b ORF2 mutant construct evaluation. SFCO=Codon optimized for *Spodoptera frugiperda*. VPL quantitation of ORF2 mutant constructs represented as μg/ml.

DETAILED DESCRIPTION OF THE PREFERRED EMBODIMENT

Figure 2:
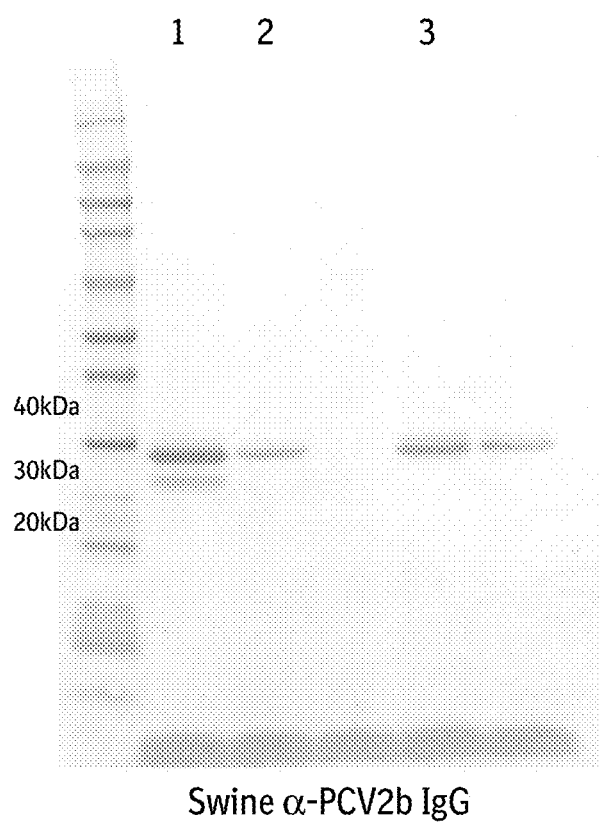
FIG. 2—Evaluation of baculovirus harvest supernatants for PCV2b ORF2. Lane 1=Circoflex WSV (PCV2a ORF2), Lane 2=PCV2b ORF2 BDH SFCO, Lane 4=PCV2b ORF2 BDH R63T, Lane 5=PCV2b ORF2 BDH R63K.

The invention is based on the surprising finding that a single mutation in the amino acid sequence of PCV2 subtype b (PCV2b) ORF2 protein is sufficient to increase the VLP production levels dramatically, thereby enabling the fast production of an effective PCV2 subunit vaccine.

In the work underlying the invention positions of major amino acid differences between PCV2a and PCV2b ORF2 sequences were identified as potential positions for mutation.

Within this context, six amino acid positions typical for the PCV2b ORF2 protein were identified, namely
  at amino acid position 59 an arginine residue or a lysine residue,
  at amino acid position 63 an arginine residue or a lysine residue,
  at amino acid position 88 a proline residue,
  at amino acid position 151 a threonine residue,
  at amino acid position 206 an isoleucine residue, and
  at amino acid position 232 an asparagine residue.

As described herein, the numbering of amino acid positions refers to the amino acid sequence of full length wild type PCV2 ORF2 protein (SEQ ID NO:2 or SEQ ID NO:5). Hence, the numbering of the amino positions as mentioned herein is with reference to a wild type PCV2 ORF2 protein sequence having 234 or 233 amino acid residues, including a methionine residue at the (N-terminal) amino acid position 1.

Thus, the phrase "wherein the numbering of the amino acid positions refers to the amino acid sequence of wild type PCV2 ORF2 protein", as used in the context of the present invention, relates to the sequence of a naturally occurring PCV2 ORF2 protein, as exemplarily set forth in SEQ ID NO:2 or SEQ ID NO:5.

Mutations of the six amino acid positions typical for PCV2b ORF2 protein unexpectedly showed that one mutation of the position within the amino acid sequence of the BC loop of the PCV2 ORF2 protein, namely a substitution of the arginine residue or lysine residue at position 63, was sufficient to increase the expression of a PCV2 ORF2 protein significantly in comparison to a PCV2 ORF2 protein that does not contain such mutation.

In one aspect, the invention thus relates to a polypeptide selected from the group consisting of the following (a), (b), and (c): (a) a PCV2 ORF2 protein having: at amino acid position 59 an arginine residue or a lysine residue, and/or at amino acid position 88 a proline residue, and/or at amino acid position 151 a threonine residue, and/or at amino acid position 206 an isoleucine residue, and/or at amino acid position 232 an asparagine residue, and having at amino acid position 63 an amino acid residue other than an arginine residue or a lysine residue, wherein the numbering of the amino acid positions refers to the amino acid sequence of wild type PCV2 ORF2 protein; (b) a PCV2 ORF2 protein characterized in that it (i) contains at least one mutation in the BC loop and (ii) is preferably expressed in a significantly higher amount compared to a PCV2 ORF2 protein that does not contain such mutation; and (c) a combination of (a) and (b).

Preferably, said polypeptide, which is also termed "polypeptide of the present invention" hereinafter, is an isolated polypeptide.

In particular, the polypeptide of the present invention is a non-naturally-occurring polypeptide.

According to the first aspect (a), the polypeptide of the invention is thus a PCV2 ORF2 protein having one, two, three, four, or five amino acid residues (single letter code in brackets) selected from the group consisting of an arginine residue (R) or a lysine residue (K) at amino acid position 59, a proline residue (P) at amino acid position 88, a threonine residue (T) at amino acid position 151, an isoleucine residue (I) at amino acid position 206, and an asparagine residue (N) at amino acid position 232, and having at amino acid position 63 an amino acid residue other than an arginine residue or a lysine residue.

In particular, the amino acid residue other than an arginine residue or a lysine residue at position 63 is a naturally occurring, preferably a genetically encoded, amino acid residue other than an arginine residue or a lysine residue.

Subsequently, also the following abbreviations are used:
  "R59" as abbreviation for "an arginine residue at amino acid position 59",
  "K59" as abbreviation for "a lysine residue at amino acid position 59",
  "P88" as abbreviation for "a proline residue at amino acid position 88",
  "T151" as abbreviation for "a threonine residue at amino acid position 151",
  "I206" as abbreviation for "an isoleucine residue at amino acid position 206",
  "N232" as abbreviation for "an asparagine residue at amino acid position 232".

Preferably, the polypeptide according to aspect (a) is thus a PCV2 ORF2 protein having P88,
  or having T151,
  or having I206,
  or having N232,
  or having R59 or K59,
  or having P88 and T151,
  or having P88 and I206,
  or having P88 and N232,
  or having P88 and R59 or K59,
  or having T151 and I206,
  or having T151 and N232,
  or having T151 and R59 or K59,
  or having I206 and N232,
  or having I206 and R59 or K59,
  or having N232 and R59 or K59,
  or having P88 and T151 and I206,
  or having P88 and T151 and N232,
  or having P88 and T151 and R59 or K59,
  or having P88 and I206 and N232,
  or having P88 and I206 and R59 or K59,
  or having P88 and N232 and R59 or K59,
  or having T151 and I206 and N232, or having T151 and I206 and R59 or K59,
or having T151 and N232 and R59 or K59,
or having I206 and N232 and R59 or K59,
or having P88 and T151 and I206 and N232,
or having P88 and T151 and I206 and R59 or K59,
or having P88 and T151 and N232 and R59 or K59,
or having P88 and I206 and N232 and R59 or K59,
or having T151 and I206 and N232 and R59 or K59,
or having P88 and T151 and I206 and N232 and R59 or K59.

More preferably, the polypeptide according to aspect (a) is hence selected from the group consisting of
PCV2 ORF 2 protein having P88,
PCV2 ORF 2 protein having T151,
PCV2 ORF 2 protein having I206,
PCV2 ORF 2 protein having N232,
PCV2 ORF 2 protein having R59
PCV2 ORF 2 protein having K59,
PCV2 ORF 2 protein having P88 and T151,
PCV2 ORF 2 protein having P88 and I206,
PCV2 ORF 2 protein having P88 and N232,
PCV2 ORF 2 protein having P88 and R59,
PCV2 ORF 2 protein having P88 and K59,
PCV2 ORF 2 protein having T151 and I206,
PCV2 ORF 2 protein having T151 and N232,
PCV2 ORF 2 protein having T151 and R59,
PCV2 ORF 2 protein having T151 and K59,
PCV2 ORF 2 protein having I206 and N232,
PCV2 ORF 2 protein having I206 and R59,
PCV2 ORF 2 protein having I206 and K59,
PCV2 ORF 2 protein having N232 and R59,
PCV2 ORF 2 protein having N232 and K59,
PCV2 ORF 2 protein having P88 and T151 and I206,
PCV2 ORF 2 protein having P88 and T151 and N232,
PCV2 ORF 2 protein having P88 and T151 and R59,
PCV2 ORF 2 protein having P88 and T151 and K59
PCV2 ORF 2 protein having P88 and I206 and N232,
PCV2 ORF 2 protein having P88 and I206 and R59,
PCV2 ORF 2 protein having P88 and I206 and K59,
PCV2 ORF 2 protein having P88 and N232 and R59,
PCV2 ORF 2 protein having P88 and N232 and K59,
PCV2 ORF 2 protein having T151 and I206 and N232,
PCV2 ORF 2 protein having T151 and I206 and R59,
PCV2 ORF 2 protein having T151 and I206 and K59,
PCV2 ORF 2 protein having T151 and N232 and R59,
PCV2 ORF 2 protein having T151 and N232 and K59,
PCV2 ORF 2 protein having I206 and N232 and R59,
PCV2 ORF 2 protein having I206 and N232 and K59,
PCV2 ORF 2 protein having P88 and T151 and I206 and N232,
PCV2 ORF 2 protein having P88 and T151 and I206 and R59,
PCV2 ORF 2 protein having P88 and T151 and I206 and K59,
PCV2 ORF 2 protein having P88 and T151 and N232 and R59,
PCV2 ORF 2 protein having P88 and T151 and N232 and K59,
PCV2 ORF 2 protein having P88 and I206 and N232 and R59,
PCV2 ORF 2 protein having P88 and I206 and N232 and K59,
PCV2 ORF 2 protein having T151 and I206 and N232 and R59,
PCV2 ORF 2 protein having T151 and I206 and N232 and K59,
PCV2 ORF 2 protein having P88 and T151 and I206 and N232 and R59, and
PCV2 ORF 2 protein having P88 and T151 and I206 and N232 and K59.

According to the second aspect (b), the polypeptide of the invention is in particular a PCV2 ORF2 protein characterized in that it (i) contains at least one mutation in the BC loop and (ii) is expressed, in particular in a baculovirus expression system, in a significantly higher amount, preferably in a higher amount by at least a factor 2, more preferably in a higher amount by at least a factor 3, still more preferably in a higher amount by at least a factor 5, yet more preferably in a higher amount by at least a factor 8, compared to a PCV2 ORF2 protein that does not contain such mutation, wherein the PCV2 ORF2 protein that does not contain such mutation preferably has an amino acid sequence identical to the polypeptide of the invention except the at least one mutation in the BC loop.

It is thus in particular understood, that the amino acid sequences of both PCV2 ORF2 proteins the expression of which is compared according to this aspect of the invention are identical except said at least one mutation in the BC loop.

The term "BC loop", within the context of the invention, in particular refers to the part of the PCV2 ORF2 amino acid sequence located between the first two N-terminal amino acid stretches folding into B sheet secondary structures, as can be seen in the crystal structure of PCV2 ORF2 protein as published by Khayat et al. J Virol 85:7856-62 (2011), which is incorporated herein by reference. In particular Khayat et al. describes loops connecting β strands BC, DE, FG, and HI as four to nine amino acid residues long, and loops BC and HI as defining knob-like protrusions extending furthest from the PCV capsid surface and decorating the 5-fold axes.

To determine if the PCV2 ORF2 protein containing at least one mutation in the BC loop is expressed in a higher amount compared to the PCV2 ORF2 protein that does not contain such mutation, preferably a method as described hereinafter in Example 1 is used.

Thus, in one example, to determine if the PCV2 ORF2 protein containing at least one mutation in the BC loop is expressed in a higher amount compared to the PCV2 ORF2 protein that does not contain such mutation, a baculovirus expression system is used in a method comprising the steps of: infecting Sf+ cells with baculovirus at a target MOI of 0.1, allowing the infection to progress for 5-7 days, harvesting by centrifugation at 20,000 g for 20 min to remove cellular debris and insoluble protein, 0.2 μm filtering of the harvest supernatants, and evaluating directly for PCV2 ORF2 expression by western blot using α-PCV2 antibodies.

Preferably, said method further comprises the preparation of baculovirus to be used for the step of infecting Sf+ cells at a target MOI of 0.1, and in particular further comprises one or more of the following steps: cloning a coding sequence which encodes the PCV2 ORF2 protein containing at least one mutation in the BC loop into a baculovirus transfer vector, cloning a coding sequence which encodes the PCV2 ORF2 protein that does not contain such mutation into a baculovirus transfer vector, co-transfecting said baculovirus transfer vector including the coding sequence which encodes the PCV2 ORF2 protein containing at least one mutation in the BC loop with baculovirus DNA in Sf9 cells, co-transfecting said baculovirus transfer vector including the coding sequence which encodes the PCV2 ORF2 protein that does not contain such mutation with baculovirus DNA in Sf9 cells.

More preferably, said method additionally further comprises one or more of the following steps: checking the resulting recombinant baculovirus for expression of PCV2 ORF2 protein by IFA, preparing an amplified stock of each recombinant baculovirus on Sf+ cells, titrating said amplified stock via the TCID$_{50}$ method to determine the baculoviral titer.

In particular, the polypeptide of the invention being a PCV2 ORF2 protein containing at least one mutation in the BC loop is expressed in a higher amount compared to the PCV2 ORF2 protein that does not contain such mutation under the same and/or comparable ambient conditions, preferably in a baculovirus expression system.

More particular, said PCV2 ORF2 protein that does not contain such mutation is a wild type PCV2 ORF2 protein.

Preferably, the at least one mutation in the BC loop according to the invention is at least one mutation in the region of the amino acid positions 58 to 66 and in particular comprises or consists of a deletion, substitution, and/or an addition of one to 7 amino acid residues in the region of the amino acid positions 60 to 66.

More preferably, the at least one mutation in the BC loop is a deletion, substitution, and/or an addition of one amino acid residue at amino acid position 63, wherein a substitution of the amino acid residue at amino acid position 63 by an amino acid residue other than an arginine residue or a lysine residue is most preferred.

Still more preferably, the substitution of the amino acid residue at amino acid position 63 by an amino acid residue other than an arginine residue or a lysine residue is a substitution by a naturally occurring, preferably a genetically encoded, amino acid residue other than an arginine residue or a lysine residue.

Preferred sequences of the BC loop according to the invention including a substitution of the amino acid residue at amino acid position 63 by an amino acid residue other than an arginine residue or a lysine residue are set forth in SEQ ID NOs: 10-45.

Thus, in particular, the at least one mutation in the BC loop in accordance with the invention comprises or is a substitution of an arginine residue or a lysine residue at amino acid position 63 by an amino acid residue other than an arginine residue or a lysine residue.

Thus, the PCV2 ORF2 protein that does not contain such mutation, as described herein, preferably has an arginine residue or a lysine residue at amino acid position 63, which is then substituted according to this preferred embodiment of the invention, thereby resulting in a polypeptide according to the invention.

Most preferably, the polypeptide of the present invention comprises a sequence selected from the group consisting of SEQ ID NOs: 10-45, wherein said sequence is in particular located at amino acid positions 58 to 66 of the sequence of the polypeptide of the present invention.

According to the third aspect (c), the polypeptide of the invention is any combination of the PCV2 ORF2 protein according to aspect (a) and aspect (b), as described herein, and is thus any PCV2 ORF2 protein having:
at amino acid position 59 an arginine residue or a lysine residue, and/or
at amino acid position 88 a proline residue, and/or
at amino acid position 151 a threonine residue, and/or
at amino acid position 206 an isoleucine residue, and/or
at amino acid position 232 an asparagine residue,
and having at amino acid position 63 an amino acid residue other than an arginine residue or a lysine residue, wherein the numbering of the amino acid positions refers to the amino acid sequence of wild type PCV2 ORF2 protein; and being characterized in that it (i) contains at least one mutation in the BC loop and (ii) is preferably expressed in a significantly higher amount compared to a PCV2 ORF2 protein that does not contain such mutation.

The term "genetically encoded amino acid residue other than an arginine residue or a lysine residue", as described in the context of the present invention, in particular refers to an amino acid residue (single letter code in brackets) selected from the group consisting of alanine residue (A), aspartate residue (D), asparagine residue (N), cysteine residue (C), glutamine residue (Q), glutamate residue (E), phenylalanine residue (F), glycine residue (G), histidine residue (H), isoleucine residue (I), leucine residue (L), methionine residue (M), proline residue (P), serine residue (S), threonine residue (T), valine residue (V), tryptophan residue (W), and tyrosine residue (Y).

More particular, said amino acid residue other than an arginine residue or a lysine residue amino is selected from the group consisting of amino acid residue with a polar but uncharged side chain, amino acid residue with a hydrophobic side chain, and glycine residue, wherein preferably the amino acid residue with a polar but uncharged side chain is selected from the group consisting of serine residue, threonine residue, tyrosine residue, asparagine residue, and glutamine residue, and/or wherein said amino acid residue with a hydrophobic side chain is preferably selected from the group consisting of alanine residue, valine residue, leucine residue, isoleucine residue, phenylalanine residue, and tryptophan residue.

Most preferably, the amino acid residue other than an arginine residue or a lysine residue, as mentioned in the context of the present invention, is selected from the group consisting of serine residue and threonine residue.

In a further preferred aspect, the polypeptide of the present invention is a recombinant PCV2 ORF2 protein, such as a recombinant baculovirus expressed PCV2 ORF2 protein.

The term "recombinant PCV2 ORF2 protein", as used herein, in particular refers to a protein molecule which is expressed from a recombinant DNA molecule, such as a polypeptide which is produced by recombinant DNA techniques. An example of such techniques includes the case when DNA encoding the expressed protein is inserted into a suitable expression vector, preferably a baculovirus expression vector, which is in turn used to transfect, or in case of a baculovirus expression vector to infect, a host cell to produce the protein or polypeptide encoded by the DNA. The term "recombinant PCV2 ORF2 protein", as used herein, thus in particular refers to a protein molecule which is expressed from a recombinant DNA molecule.

According to a particular example, the recombinant PCV2 ORF2 protein is produced by a method with the following steps: The gene for PCV2 ORF2 is cloned into a baculovirus transfer vector; the transfer vector is used to prepare recombinant baculovirus containing said gene by homologous recombination in insect cells; and the PCV2 ORF2 protein is then expressed in insect cells during infection with the recombinant baculovirus.

According to an alternative example, the recombinant PCV2 ORF2 protein is expressed in insect cells from a recombinant expression plasmid. In the case of this alternative example baculovirus is not needed.

It is further understood that the term "recombinant PCV2 protein consisting of a sequence" in particular also concerns any cotranslational and/or posttranslational modification or modifications of the sequence affected by the cell in which the polypeptide is expressed. Thus, the term "recombinant PCV2 ORF2 protein consisting of a sequence", as described herein, is also directed to the sequence having one or more modifications effected by the cell in which the polypeptide is expressed, in particular modifications of amino acid residues effected in the protein biosynthesis and/or protein processing, preferably selected from the group consisting of glycosylations, phosphorylations, and acetylations.

Preferably, the recombinant PCV2 ORF2 protein according to the invention is produced or obtainable by a baculovirus expression system, in particular in cultured insect cells.

In another preferred aspect, the polypeptide of the present invention is a PCV2 subtype b (PCV2b) ORF2 protein.

In yet a further preferred aspect, the polypeptide of the present invention is a PCV2 ORF2 protein comprising or consisting of an amino acid sequence having at least 90%, preferably at least 92%, more preferably at least 94%, even more preferably at least 96%, still more preferably at least 98%, or in particular 100% sequence identity with the amino acid sequence of SEQ ID NO: 1.

Figure 8:
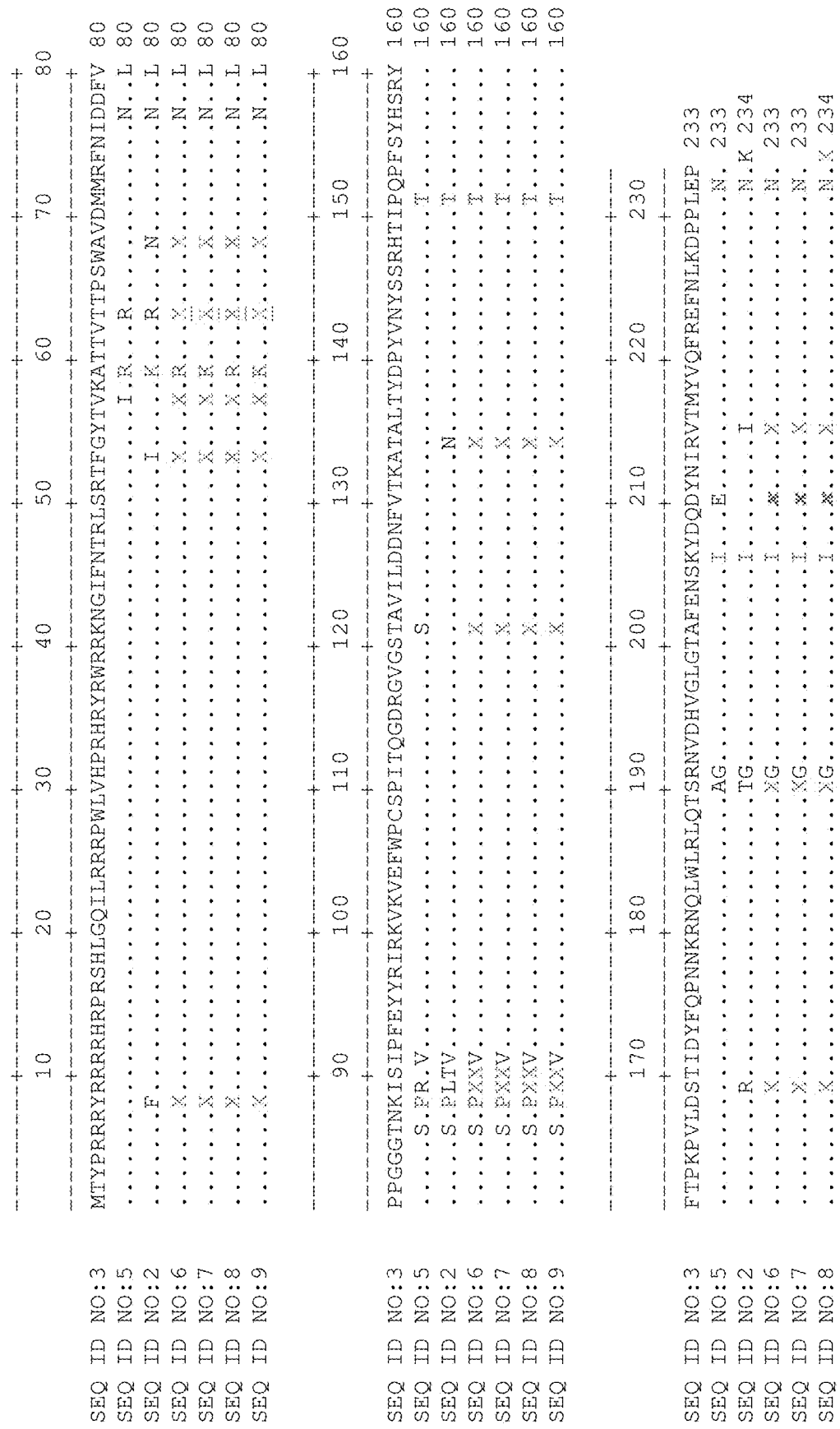
FIG. 8—Alignment of PCV2b ORF2 wild type and mutant amino acid sequences, wherein the sequences designated SEQ ID NO: 5 and SEQ ID NO: 2 are PCV2b ORF2 wild type sequences and the sequences designated SEQ ID NO: 6, SEQ ID NO: 7, SEQ ID NO: 8, and SEQ ID NO: 9 are mutant sequences, and wherein SEQ ID NO: 3 corresponds to the sequence of a wild type PCV2a ORF2 protein. In the sequences designated SEQ ID NO:6, SEQ ID NO:7, SEQ ID NO:8, and SEQ ID NO:9: "X" (at positions 8, 53, 57, 68, 89, 90, 121, 134, 169, 190, 215, and 234) is any amino acid residue selected from the group consisting of A, C, D, E, F, G, H, I, K, L, M, N, P, Q, R, S, T, V, W, and Y; "X" (at position 63) is any amino acid residue selected from the group consisting of A, C, D, E, F, G, H, I, L, M, N, P, Q, S, T, V, W, and Y; and "K" (at position 210) is any amino acid residue selected from the group consisting of D and E.

Most preferably, the polypeptide of the present invention is selected from the group consisting of the sequences of SEQ ID NOs: 6-9, which are also shown in FIG. 8. Thus, the polypeptide of the present invention is preferably selected from the following sequences (i)-(iv):

(i)
(SEQ ID NO: 6)
MTYPRRRXRRRRHRPRSHLGQILRRRPWLVHPRHRYRWRRKNGIFNTRLS

RTXGYTXKRTTVXTPSWXVDMMRFNINDFLPPGGGSNPXXVPFEYYRIRK

VKVEFWPCSPITQGDRGVGSXAVILDDNFVTKAXALTYDPYVNYSSRHTI

TQPFSYHSRYFTPKPVLDXTIDYFQPNNKRNQLWLRLQTXGNVDHVGLGT

AFENSIYDQ*YNIRXTMYVQFREFNLKDPPLNP, (ii)
(SEQ ID NO: 7)
MTYPRRRXRRRRHRPRSHLGQILRRRPWLVHPRHRYRWRRKNGIFNTRLS

RTXGYTXKKTTVXTPSWXVDMMRFNINDFLPPGGGSNPXXVPFEYYRIRK

VKVEFWPCSPITQGDRGVGSXAVILDDNFVTKAXALTYDPYVNYSSRHTI

TQPFSYHSRYFTPKPVLDXTIDYFQPNNKRNQLWLRLQTXGNVDHVGLGT

AFENSIYDQ*YNIRXTMYVQFREFNLKDPPLNP, (iii)
(SEQ ID NO: 8)
MTYPRRRXRRRRHRPRSHLGQILRRRPWLVHPRHRYRWRRKNGIFNTRLS

RTXGYTXKRTTVXTPSWXVDMMRFNINDFLPPGGGSNPXXVPFEYYRIRK

VKVEFWPCSPITQGDRGVGSXAVILDDNFVTKAXALTYDPYVNYSSRHTI

TQPFSYHSRYFTPKPVLDXTIDYFQPNNKRNQLWLRLQTXGNVDHVGLGT

AFENSIYDQ*YNIRXTMYVQFREFNLKDPPLNPX, (iv)
(SEQ ID NO: 9)
MTYPRRRXRRRRHRPRSHLGQILRRRPWLVHPRHRYRWRRKNGIFNTRLS

RTXGYTXKKTTVXTPSWXVDMMRFNINDFLPPGGGSNPXXVPFEYYRIRK

VKVEFWPCSPITQGDRGVGSXAVILDDNFVTKAXALTYDPYVNYSSRHTI

TQPFSYHSRYFTPKPVLDXTIDYFQPNNKRNQLWLRLQTXGNVDHVGLGT

AFENSIYDQ*YNIRXTMYVQFREFNLKDPPLNPX, wherein in said sequences (i)-(iv):
"X" is any amino acid residue selected from the group consisting of A, C, D, E, F, G, H, I, K, L, M, N, P, Q, R, S, T, V, W, and Y;
"X" is any amino acid residue selected from the group consisting of A, C, D, E, F, G, H, I, L, M, N, P, Q, S, T, V, W, and Y; and
"x" is any amino acid residue selected from the group consisting of D and E.

For explanatory purposes and in a non-limiting example, the polypeptide according to the invention is a polypeptide consisting of the sequence:

(SEQ ID NO: 46)
MTYPRRRFRRRRHRPRSHLGQILRRRPWLVHPRHRYRWRRKNGIFNTRLS

RTIGYTVKKTTVXTPSWNVDMMRFNINDFLPPGGGSNPLTVPFEYYRIRK

VKVEFWPCSPITQGDRGVGSTAVILDDNFVTKANALTYDPYVNYSSRHTI

TQPFSYHSRYFTPKPVLDRTIDYFQPNNKRNQLWLRLQTTGNVDHVGLGT

AFENSIYDQDYNIRITMYVQFREFNLKDPPLNPK, wherein "X" is any amino acid residue selected from the group consisting of A, C, D, E, F, G, H, I, L, M, N, P, Q, S, T, V, W, and Y.

In still another preferred aspect of the present invention, the wild type PCV2 ORF2 protein, as described herein, is the protein set forth in SEQ ID NO: 2.

According to another aspect, the invention further provides an immunogenic composition containing the polypeptide of the present invention.

According to another preferred aspect, the invention further provides an immunogenic composition containing the polypeptide of the present invention, and a PCV2a ORF-2 polypeptide, wherein said PCV2a ORF-2 polypeptide is preferably a polypeptide that is at least 94% or preferably at least 95% identical to the sequence of SEQ ID NO: 3.

According to a further aspect, the invention also provides a polynucleotide comprising a sequence which encodes the polypeptide of the present invention, wherein said polynucleotide according to the invention is preferably an isolated polynucleotide.

For explanatory purposes and in a non-limiting example, the polynucleotide according to the invention is a polynucleotide comprising the sequence set forth in SEQ ID NO: 4.

Production of the polynucleotides described herein is within the skill in the art and can be carried out according to recombinant techniques described, among other places, in Sam brook et al., 2001, Molecular Cloning, A Laboratory Manual, Cold Spring Harbor Laboratory Press, Cold Spring Harbor, N.Y.; Amusable, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

Also, the invention in particular provides a baculovirus which contains a polynucleotide comprising a sequence which encodes the polypeptide of the present invention, wherein said baculovirus according to the invention is preferably an isolated baculovirus.

Further, the invention also provides a plasmid, preferably an expression vector, which comprises a polynucleotide comprising a sequence which encodes the polypeptide of the present invention, wherein said plasmid according to the invention is in particular an isolated plasmid.

The invention also provides a cell comprising a baculovirus which contains a polynucleotide comprising a sequence which encodes the polypeptide of the present invention, or a plasmid, preferably an expression vector, which comprises a polynucleotide comprising a sequence which encodes the polypeptide of the present invention, wherein said cell according to the invention is preferably an isolated cell.

In still another aspect, the invention also relates to the use of the polypeptide of the present invention; the baculovirus according to the invention; the immunogenic composition according to the invention; the polynucleotide according to the invention; the plasmid according to the invention; and/or the cell according to the invention for the preparation of a medicament, preferably of a vaccine.

In this context, the invention also provides a method of producing the polypeptide of the present invention of, wherein said method comprises the step of infecting a cell, preferably an insect cell, with the baculovirus of the invention.

Further, the invention also provides a method of producing the polypeptide of the present invention, wherein said method comprises the step of transfecting a cell with the plasmid according to the invention.

The polypeptide of the present invention is preferably expressed in high amounts sufficient for the stable self-assembly of virus like particles, which may then be used for a single shot vaccination, in particular if they are contained in an immunogenic composition, thereby allowing the reduction and prevention of clinical signs caused by an infection with PCV2, such as an infection with PCV2b and/or PCV2a.

The invention is thus in particular further based on the polypeptide of the present invention or on the immunogenic composition according to the invention, respectively, wherein said polypeptide of the present invention or said immunogenic composition comprising the polypeptide of the present invention may be used for particular purposes.

In one aspect, the invention thus relates to the polypeptide of the present invention or an immunogenic composition comprising the polypeptide of the present invention for use in a method for the treatment or prevention of an infection with PCV2, the reduction, prevention or treatment of clinical signs caused by an infection with PCV2, or the prevention or treatment of a disease caused by an infection with PCV2.

The invention also provides a method for the treatment or prevention of an infection with PCV2, the reduction, prevention or treatment of clinical signs caused by an infection with PCV2, or the prevention or treatment of a disease caused by an infection with PCV2, comprising administering the polypeptide of the present invention or an immunogenic composition comprising the polypeptide of the present invention to an animal, in particular to an animal in need thereof.

Also, the invention provides the use of the polypeptide of the present invention or of an immunogenic composition comprising the polypeptide of the present invention for the preparation of a medicament for the treatment or prevention of an infection with PCV2, the reduction, prevention or treatment of clinical signs caused by an infection with PCV2, or the treatment or prevention of a disease caused by an infection with PCV2.

In a preferred aspect, the infection with PCV2, as described herein, is an infection with PCV2 subtype b (PCV2b) and/or an infection with PCV2 of a subtype other than subtype 2b.

As used herein, the term "infection with PCV2" is equivalent to the term "PCV2 infection".

In particular, the infection with PCV2 of a subtype other than subtype 2b, as mentioned herein, is an infection with PCV2 subtype a (PCV2a) and/or PCV2 subtype c (PCV2c), and is preferably an infection with PCV2a.

The term "PCV2 subtype b (PCV2b) ORF2 protein", as described herein, relates to the protein encoded by the ORF2 gene of a PCV-2b as defined by the standardized nomenclature for PCV2 genotype definition (Segales, J. et al., 2008, PCV-2 genotype definition and nomenclature, Vet Rec 162:867-8) which is incorporated herein by reference).

According to another preferred aspect, the infection with PCV2 of a subtype other than subtype 2b, as described herein, is a concurrent infection with (i) PCV2 of a subtype other than subtype 2b and (ii) PCV2b, in particular a concurrent infection with PCV2a and PCV2b.

The terms "PCV2a", "PCV2b" and "PCV2c", respectively, as described herein, relate to PCV-2a, PCV-2b and PCV-2c, respectively, according to the standardized nomenclature for PCV2 genotype definition (Segales, J. et al., 2008, PCV-2 genotype definition and nomenclature, Vet Rec 162:867-8, which is incorporated herein by reference).

In particular, the infection with PCV2b, as mentioned herein, is an infection with (i) a PCV2 comprising a polypeptide that is at least 94%, preferably at least 95%, more preferably at least 96%, still more preferably at least 97%, yet more preferably at least 98%, and most preferably at least 99% identical to the sequence of SEQ ID NO: 2 or (ii) a PCV2 comprising a polynucleotide which comprises a sequence encoding a polypeptide that is at least 94%, preferably at least 95%, more preferably at least 96%, still more preferably at least 97%, yet more preferably at least 98%, and most preferably at least 99% identical to the sequence of SEQ ID NO:2.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X, respectively. In this context, "X" is any integer selected from 1 to 3 so that "SEQ ID NO: X" represents any of the SEQ ID NOs mentioned herein.

Preferably, the infection with PCV2a, as described herein, is an infection with (i) a PCV2 comprising a polypeptide that is at least 94%, preferably at least 95%, more preferably at least 96%, still more preferably at least 97%, yet more preferably at least 98%, and most preferably at least 99% identical to the sequence of SEQ ID NO:3 or (ii) a PCV2 comprising a polynucleotide which comprises a sequence encoding a polypeptide that is at least 94%, preferably at least 95%, more preferably at least 96%, still more preferably at least 97%, yet more preferably at least 98%, and most preferably at least 99% identical to the sequence of SEQ ID NO:3.

Preferably, in the context of the present invention, the treatment or prevention of an infection with PCV2 is based on or comprises or consists of the induction of an immune response against said PCV2, the clinical signs, as mentioned herein, are selected from the group consisting of lymphoid depletion, lymphoid inflammation, positive IHC for PCV2 antigen of lymphoid tissue, viremia, nasal shedding, pyrexia, reduced average daily weight gain, lung inflammation, positive IHC for PCV2 antigen of lung tissue, and/or the disease, as mentioned herein, is PMWS.

In particular, in the context of the present invention, the treatment or prevention of an infection with PCV2 of a subtype other than 2b is based on or comprises or consists of the induction of an immune response against said PCV2 of a subtype other than 2b or the concurrent induction of an immune response against said PCV2 of a subtype other than 2b and PCV2b.

The term "prevention" or "reduction" or "preventing" or "reducing", respectively, as used herein, means, but is not limited to a process which includes the administration of a PCV2 antigen, namely of the polypeptide of the present invention, which is included in the composition of the invention, to an animal, wherein said PCV2 antigen, when administered to said animal elicits or is able to elicit an immune response in said animal against PCV2. Altogether, such treatment results in reduction of the clinical signs of a disease caused by PCV2 or of clinical signs associated with PCV2 infection, respectively. More specifically, the term "prevention" or "preventing", as used herein, means generally a process of prophylaxis in which an animal is exposed to the immunogenic composition of the present invention prior to the induction or onset of the disease process caused by PCV2.

Herein, "reduction of clinical signs associated with PCV2 infection" means, but is not limited to, reducing the number of infected subjects in a group, reducing or eliminating the number of subjects exhibiting clinical signs of infection, or reducing the severity of any clinical signs that are present in the subjects, in comparison to wild-type infection. For example, it should refer to any reduction of pathogen load, pathogen shedding, reduction in pathogen transmission, or reduction of any clinical sign symptomatic of PCV2 infection. Preferably these clinical signs are reduced in subjects receiving the composition of the present invention by at least 10% in comparison to subjects not receiving the composition and may become infected. More preferably, clinical signs are reduced in subjects receiving the composition of the present invention by at least 20%, preferably by at least 30%, more preferably by at least 40%, and even more preferably by at least 50%.

The term "reduction of viremia" means, but is not limited to, the reduction of PCV2 virus entering the bloodstream of an animal, wherein the viremia level, i.e., the number of PCV2 RNA copies per mL of blood serum or the number of plaque forming colonies per deciliter of blood serum, is reduced in the blood serum of subjects receiving the composition of the present invention by at least 50% in comparison to subjects not receiving the composition and may become infected. More preferably, the viremia level is reduced in subjects receiving the composition of the present invention by at least 90%, preferably by at least 99.9%, more preferably by at least 99.99%, and even more preferably by at least 99.999%.

As used herein, the term "viremia" is particularly understood as a condition in which PCV2 particles reproduce and circulate in the bloodstream of an animal.

The term "animal", as used herein, in particular relates to a mammal, preferably to swine, more preferably to a pig, most preferably to a piglet.

According to a particular preferred aspect of the invention, the polypeptide of the present invention or the immunogenic composition according to the invention is administered only once.

Preferably, in the context of the present invention, the polypeptide of the present invention or the immunogenic composition according to the invention is to be administered or is administered, respectively, in particular only once, to an animal, preferably to a swine, more preferably to a pig, in particular preferably to a piglet.

The present invention overcomes the problems inherent in the prior art and provides a distinct advance in the state of the art. According to another aspect, the present invention also provides a method for the treatment or prevention of a PCV2 infection or for reduction of clinical signs caused by or associated with a PCV2 infection in animals, preferably animals having anti-PCV2 antibodies, comprising the step of administering an effective amount of the polypeptide of the present invention or the immunogenic composition according to the invention to that animal in need of such treatment.

The terms "vaccine" or "immunogenic composition" (both terms are used synonymously) as used herein refers to any pharmaceutical composition containing the polypeptide of the present invention, which composition can be used to prevent or treat a PCV2 infection-associated disease or condition in a subject. A preferred immunogenic composition can induce, stimulate or enhance the immune response against PCV2. The term thus encompasses both subunit immunogenic compositions, as described below, as well as compositions containing whole killed, or attenuated and/or inactivated PCV2b mutant.

It is in particular understood that the term "PCV2b mutant", as described herein, relates to a PCV2b mutant comprising the polypeptide of the present invention and/or the polynucleotide according to the invention.

According to another aspect, the present invention also provides a method for the treatment or prevention of a PCV2 infection or for reduction of clinical signs caused by or associated with a PCV2 infection in animals, preferably animals having anti-PCV2 antibodies, in particular maternal derived anti-PCV2 antibodies, comprising the step of administering an effective amount of the polypeptide of the present invention or an immunogenic composition comprising the polypeptide of the present invention to that animal in need of such treatment, wherein the immunogenic composition is subunit immunogenic composition, a compositions containing whole killed, or attenuated and/or inactivated PCV2b.

The term "subunit immunogenic composition" as used herein refers to a composition containing at least one immunogenic polypeptide or antigen, but not all antigens, derived from or homologous to an antigen from a PCV2b mutant. Such a composition is substantially free of intact PCV2b mutant. Thus, a "subunit immunogenic composition" is prepared from at least partially purified or fractionated (preferably substantially purified) immunogenic polypeptides from a PCV2b mutant, or recombinant analogs thereof. A subunit immunogenic composition can comprise the subunit antigen or antigens of interest substantially free of other antigens or polypeptides from a PCV2b mutant, or in fractionated from. A preferred immunogenic subunit composition comprises the polypeptide of the present invention as described herein.

An "immune response" means but is not limited to the development in a host of a cellular and/or antibody-mediated immune response to the composition or vaccine of interest. Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the signs associated with PCV2 infections, in particular an infection with PCV2 subtype b (PCV2b) and/or an infection with PCV2 of a subtype other than subtype 2b, in delay of onset of viremia, in a reduced viral persistence, in a reduction of the overall viral load and/or a reduction of viral excretion.

The term "antigen" as used herein refer to an amino acid sequence which elicits an immunological response as described above.

According to a further aspect, the immunogenic composition as used herein most preferably comprises the polypeptide of the present invention, or a fragment thereof, expressed by the polypeptide according to the invention. A preferred polypeptide of the present invention is that of SEQ ID NO: 1. However, it is understood by those of skill in the art that this sequence could vary by as much as 1-5% in sequence homology and still retain the antigenic characteristics that render it useful in immunogenic compositions according to invention.

"Sequence identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1): 387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus, according to a further aspect, the present invention also provides a method for the treatment or prevention of a PCV2 infection or for reduction of clinical signs caused by or associated with a PCV2 infection in animals, preferably animals having anti-PCV2 antibodies, in particular maternal derived anti-PCV2 antibodies, comprising the step of administering an effective amount of the polypeptide of the present invention or an immunogenic composition comprising the polypeptide of the present invention to that animal in need of such treatment, wherein said the polypeptide of the present invention is anyone of those, described herein. Preferably, the polypeptide of the present invention protein is: (i) a polypeptide comprising or consisting of the sequence of SEQ ID NO: 1; or (ii) any polypeptide that is at least 95% homologous to the polypeptide of (i).

According to a further aspect, the polypeptide of the present invention is provided in the immunogenic composition at a protein inclusion level effective for inducing the desired immune response, namely reducing the incidence of, lessening the severity of, or preventing or reducing one or more clinical signs resulting from or associated with a PCV2 infection. Preferably, the inclusion level of the polypeptide of the present invention is at least 0.2 μg protein/ml of the final immunogenic composition (μg/ml), more preferably from about 0.2 to about 400 μg/ml, still more preferably from about 0.3 to about 200 μg/ml, even more preferably from about 0.35 to about 100 μg/ml, still more preferably from about 0.4 to about 50 μg/ml, still more preferably from about 0.45 to about 30 μg/ml, still more preferably from about 0.5 to about 18 μg/ml, even more preferably from about 0.6 to about 15 μg/ml even more preferably from about 0.75 to about 8 μg/ml, even more preferably from about 1.0 to about 6 μg/ml, still more preferably from about 1.3 to about 3.0 μg/ml, even more preferably from about 1.4 to about 2.5 μg/ml, even more preferably from about 1.5 to about 2.0 μg/ml, and most preferably about 1.6 μg/ml.

According to a further aspect, the protein inclusion level is at least 0.2 μg/PCV2b ORF-2 protein as described above per dose of the final immunogenic composition (μg/dose), more preferably from about 0.2 to about 400 μg/dose, still more preferably from about 0.3 to about 200 μg/dose, even more preferably from about 0.35 to about 100 μg/dose, still more preferably from about 0.4 to about 50 μg/dose, still more preferably from about 0.45 to about 30 μg/dose, still more preferably from about 0.5 to about 18 μg/dose, even more preferably from about 0.6 to about 15 μg/ml, even more preferably from about 0.75 to about 8 μg/dose, even more preferably from about 1.0 to about 6 μg/dose, still more preferably from about 1.3 to about 3.0 μg/dose, even more preferably from about 1.4 to about 2.5 μg/dose, even more preferably from about 1.5 to about 2.0 μg/dose, and most preferably about 1.6 μg/dose. Also, an inclusion level of the polypeptide of the present invention (antigen content) of less than 20 μg/dose, preferably of about 0.5 to 18 μg/dose is suitable to confer immunity in young animals and/or in animals which are positive for PCV2 antibodies, in particular which are positive for anti-PCV2 maternal derived antibodies. Thus, according to a further aspect, the present invention also provides a method for the treatment or prevention of a PCV2 infection or for reduction of clinical signs caused by or associated with a PCV2 infection in animals, preferably animals having anti-PCV2 antibodies, in particular maternal derived anti-PCV2 antibodies, comprising the step of administering less than 20 μg/dose, preferably of about 0.5 to 18 μg/dose of the polypeptide of the present invention or an immunogenic composition comprising the polypeptide of the present invention to that animal in need of such treatment. Said polypeptide of the present invention is anyone described in this patent application.

The polypeptide of the present invention used in the immunogenic composition in accordance with the present invention can be derived in any fashion including isolation and purification of the polypeptide of the present invention, standard protein synthesis, and recombinant methodology. Preferred methods for obtaining the polypeptide of the present invention are provided in WO06/072065, the teachings and content of which are hereby incorporated by reference in its entirety, since surprisingly it has been found that the methods described therein for obtaining PCV2a ORF-2 polypeptide can be used accordingly for obtaining the polypeptide of the present invention. Briefly, susceptible cells are infected with a recombinant viral vector containing DNA coding sequences encoding the polypeptide of the present invention, the polypeptide of the present invention protein is expressed by the recombinant virus, and the expressed polypeptide of the present invention is recovered from the supernatant by filtration and inactivated by any conventional method, preferably using binary ethylenimine, which is then neutralized to stop the inactivation process.

The immunogenic composition as used herein also refers to a composition that comprises i) any of the polypeptides of the present invention described above, preferably in concentrations described above, and ii) at least a portion of the viral vector expressing said polypeptide of the present invention, preferably of a recombinant baculovirus. Moreover, the immunogenic composition can comprise i) any of the polypeptides of the present invention described above, preferably in concentrations described above, ii) at least a portion of the viral vector expressing said polypeptide of the present invention, preferably of a recombinant baculovirus, and iii) a portion of the cell culture supernatant.

Thus, according to a further aspect, the present invention also provides a method for the treatment or prevention of a PCV2 infection or for reduction of clinical signs caused by or associated with a PCV2 infection in animals, preferably animals having anti-PCV2 antibodies, in particular maternal derived anti-PCV2 antibodies, comprising the step of administering an effective amount of the polypeptide of the present invention or an immunogenic composition comprising the polypeptide of the present invention to that animal in need of such treatment, wherein the polypeptide of the present invention is a recombinant, preferably a baculovirus expressed, polypeptide of the present invention. Preferably those recombinant or baculovirus expressed polypeptides of the present invention having the sequence as described above.

The immunogenic composition as used herein also refers to a composition that comprises i) any of the polypeptides of the present invention described above, preferably in concentrations described above, ii) at least a portion of the viral vector expressing said polypeptide of the present invention, preferably of a recombinant baculovirus, and iii) a portion of the cell culture; wherein about 90% of the components have a size smaller than 1 μm.

The immunogenic composition as used herein also refers to a composition that comprises i) any of the polypeptides of the present invention described above, preferably in concentrations described above, ii) at least a portion of the viral vector expressing said polypeptide of the present invention, iii) a portion of the cell culture, iv) and inactivating agent to inactivate the recombinant viral vector preferably BEI, wherein about 90% of the components i) to iii) have a size smaller than 1 μm. Preferably, BEI is present in concentrations effective to inactivate the baculovirus, preferably in an amount of 2 to about 8 mM BEI, preferably of about 5 mM BEI.

The immunogenic composition as used herein also refers to a composition that comprises i) any of the polypeptides of the present invention described above, preferably in concentrations described above, ii) at least a portion of the viral vector expressing said polypeptide of the present invention, iii) a portion of the cell culture, iv) an inactivating agent to inactivate the recombinant viral vector preferably BEI, and v) an neutralization agent to stop the inactivation mediated by the inactivating agent, wherein about 90% of the components i) to iii) have a size smaller than 1 μm. Preferably, if the inactivating agent is BEI, said composition comprises sodium thiosulfate in equivalent amounts to BEI.

The protein is incorporated into a composition that can be administered to an animal susceptible to PCV2 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises the polypeptide of the present invention as provided herewith, preferably in concentrations described above, which is mixed with an adjuvant, preferably Carbopol, and physiological saline.

Those of skill in the art will understand that the composition used herein may incorporate known injectable, physiologically acceptable sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g., anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g., vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Carbopol, in particular the use of Carbopol 971P, preferably in amounts of about 500 μg to about 5 mg per dose, even more preferred in an amount of about 750 μg to about 2.5 mg per dose and most preferred in an amount of about 1 mg per dose.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, or muramyl dipeptide among many others.

Preferably, the adjuvant is added in an amount of about 100 μg to about 10 mg per dose. Even more preferably, the adjuvant is added in an amount of about 100 μg to about 10 mg per dose. Even more preferably, the adjuvant is added in an amount of about 500 μg to about 5 mg per dose. Even more preferably, the adjuvant is added in an amount of about 750 μg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith, contains polypeptide of the present invention recovered from the supernatant of in vitro cultured cells, wherein said cells were infected with a recombinant viral vector containing DNA encoding the polypeptide of the present invention and expressing the polypeptide of the present invention, and wherein said cell culture was treated with about 2 to about 8 mM BEI, preferably with about 5 mM BEI to inactivate the viral vector, and an equivalent concentration of a neutralization agent, preferably sodium thiosulfate solution to a final concentration of about 2 to about 8 mM, preferably of about 5 mM.

The present invention also relates to an immunogenic composition that comprises i) any of the polypeptides of the present invention described above, preferably in concentrations described above, ii) at least a portion of the viral vector expressing said polypeptide of the present invention, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; and vi) a suitable adjuvant, preferably Carbopol 971 in amounts described above; wherein about 90% of the components i) to iii) have a size smaller than 1 μm. According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic composition as used herein also refers to a composition that comprises per one ml (i) at least 1.6 μg of the polypeptide of the present invention described above, preferably less than 20 μg (ii) at least a portion of baculovirus expressing said polypeptide of the present invention (iii) a portion of the cell culture, (iv) about 2 to 8 mM BEI, (v) sodium thiosulfate in equivalent amounts to BEI; and (vi) about 1 mg Carbopol 971, and (vii) phosphate salt in a physiologically acceptable concentration; wherein about 90% of the components (i) to (iii) have a size smaller than 1 μm and the pH of said immunogenic composition is adjusted to about 6.5 to 7.5.

The immunogenic compositions can further include one or more other immuno-modulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 μg to about 2000 μg of adjuvant and preferably about 250 μg/ml dose of the vaccine composition. Thus, the immunogenic composition as used herein also refers to a composition that comprises from about 1 ug/ml to about 60 μg/ml of antibiotics, and more preferably less than about 30 μg/ml of antibiotics.

The immunogenic composition as used herein also refers to a composition that comprises (i) any of the polypeptides of the present invention described above, preferably in concentrations described above; (ii) at least a portion of the viral vector expressing said polypeptide of the present invention; (iii) a portion of the cell culture; (iv) an inactivating agent to inactivate the recombinant viral vector preferably BEI; and (v) an neutralization agent to stop the inactivation mediated by the inactivating agent, preferably sodium thiosulfate in equivalent amounts to BEI; (vi) a suitable adjuvant, preferably Carbopol 971 in amounts described above; (vii) a pharmaceutical acceptable concentration of a saline buffer, preferably of a phosphate salt; and (viii) an anti-microbiological active agent; wherein about 90% of the components (i) to (iii) have a size smaller than 1 μm.

For investigation of a possible interference of the polypeptide of the present invention with the maternal antibody a study may be conducted in which the antibody titers of study animals are determined at the time of vaccination which are then grouped into a low, moderate and high antibody class: Geometric mean titers of <1:100 are considered as low antibody titers, titers of 1:100 to 1:1000 are considered as moderate antibody titers and titers of >1:1000 are considered as high antibody titers. This grouping pattern is comparable to that done in a Canadian field study where antibody titers of 1:80 were considered as low, antibody titers of 1:640 as moderate and antibody titers of >1:1280 as high (Larochelle et al., 2003, Can. J. Vet. Res.; 67: 114-120). In order to analyze the impact of low, medium and high antibody titers at the time of vaccination on viremia, vaccinated and placebo-treated animals are compared with regard to the onset, end, duration of viremia, the number of positive sampling days and the virus load. The presence of anti-PCV2 antibodies, in particular of maternal derived antibodies, preferably has no significant impact of any of those parameters. In other words, the efficacy of the polypeptide of the present invention in prevention and treatment of a PCV2 infection or in reduction of clinical signs caused by or associated with a PCV2 infection in animals is preferably not affected at the day of vaccination by the presence of anti-PCV2 antibodies, preferably by anti-PCV2 antibody titers of up to 1:100, preferably of more than 1:100, even more preferably of more than 1:250, even more preferably of more than 1:500, even more preferably of 1:640; even more preferably of more than 1:750, most preferably of more than 1:1000. This effect can be shown in a one shot vaccination experiment, which means that the polypeptide of the present invention is administered only once and without any subsequent administration of the polypeptide of the present invention.

Methods for detection and quantification of anti-PCV2 antibodies are well known in the art. For example detection and quantification of PCV2 antibodies can be performed by indirect immunofluorescence as described in Magar et al., 2000, Can. J. Vet Res.; 64: 184-186 or Magar et al., 2000, J. Comp. Pathol.; 123: 258-269. Further assays for quantification of anti-PCV2 antibodies are described in Opriessnig et al., 2006, 37th Annual Meeting of the American Association of Swine Veterinarians. Moreover, an indirect immunofluorescence assay, that can be used by a person skilled in the art comprises the steps of: seeding about 20.000 to 60.000 PK15 or VIDO R1 cells per well onto a 96 well plate; infecting cells with a PCV2 isolate, when monolayers are approximately 65 to 85% confluent; incubating infected cells for 48 hours; removing medium and washing cells 2 times with PBS; discarding the wash buffer and treating cells with cold 50/50 methanol/acetone fixative (~100 μl/well) for about 15 min at about −20° C.; discarding the fixative and air drying of the plates; preparing serial dilutions of porcine serum samples in PBS and serial dilutions of an anti-PCV2 positive and negative control sample (Positive Control and Negative Control Samples); adding the serial dilutions to the plates and incubating to allow antibodies to bind if present in the serum samples for about 1 hr. at 36.5±1° C.; washing the plates three times with PBS an discarding the PBS; staining the plates with a commercial Goat anti-Swine FITC conjugate diluted 1:100 in PBS and incubated for about 1 hr. at 36.5±1° C.; removing microplates are removed from incubator, the conjugate is discarded and the plates are washed 2 times with PBS; reading the plates using UV microscopy and reporting individual wells as positive or negative, wherein the Positive Control and Negative Control samples are used to monitor the test system; and calculating the serum antibody titers using the highest dilution showing specific IFA reactivity and the number of wells positive per dilution, or a 50% endpoint is calculated using the appropriate Reed-Muench formula.

Such an assay is described in Example 2 of WO 2008/076915 A2.

In cases of controversial results and in any question of doubt, anti-PCV2 titers as mentioned herein, refer to those which are/can be estimated by this assay.

Thus according to a further aspect, the present invention provides a method for the treatment or prevention of a PCV2 infection or for reduction of clinical signs caused by or associated with a PCV2 infection in animals, preferably animals having anti-PCV2 antibodies, in particular maternal antibodies, comprising the step of administering an effective amount of a polypeptide of the present invention to that animal in need of such treatment, preferably of less than 20 µg/dose wherein said animal have a detectable anti-PCV2 antibody titer of up to 1:100, preferably of more than 1:100, even more preferably of more than 1:250, even more preferably of more than 1:500, even more preferably of 1:640, even more preferably of more than 1:750, most preferably of more than 1:1000. Preferably, those anti-PCV2 antibody titer is detectable and quantifiable in a specific anti-PCV2 immune assay, preferably in the assay as described above, as exemplarily described in Example 2 of WO 2008/076915 A2. More preferably, those anti-PCV-2 antibodies are maternal derived antibodies. Most preferably, the polypeptide of the present invention is only administered once, preferably with a dose of less than 20 µg/dose.

Piglets with only low titers (<1:100) or moderate titers (<1:1000) of maternal derived anti-PCV2 antibodies are not sufficient protected against PCV2 infections which occur prior to week 3 of age. Therefore, vaccination at a very early stage of life is desirable. Within the context of the invention, vaccination/treatment of animals at or before 3 weeks of age is preferred. Moreover, anti-PCV2 antibody titers of more than 1:1000 preferably have no influence on the efficacy of the PCV2 vaccine regardless of the level of the existing initial antibody titer. For example, vaccination of high-titer animals (anti-PCV2 antibody titer>1:1000) preferably result in a shorter duration of viremia, an earlier end of viremia, less viremic sampling days and a reduction of the sum of genomic equivalents/ml as compared to non-vaccinated control animals. Upon comparison of vaccinated "high", "moderate" and "low titer animals" no significant differences are preferably observed with regard to the different parameters of PCV2 viraemia. Also in the presence of high anti-PCV2 antibody titers the polypeptide of the present invention used for vaccination preferably still significantly reduces viremia in blood (end of viremia, duration of viremia, virus load). Preferably, no differences are found with regard to the live body weight when comparing low and high titer animals of the vaccinated group. Furthermore, vaccinated animals with a high anti-PCV2 antibody titer at the time of vaccination/treatment (>1:1000) also preferably show a significantly higher body weight after the onset of viremia compared to placebo-treated animals with initial high antibody titers. Consequently, according to a preferred aspect, vaccination/treatment of animals of 1 day of age or older with the polypeptide of the present invention is possible. However, vaccination should be done within the first 8, preferably within the first 7 weeks of age. Thus according to a further aspect, the present invention provides a method for the treatment or prevention of a PCV2 infection or for reduction of clinical signs caused by or associated with a PCV2 infection in animals, comprising the step of administering to that animal in need of such treatment at day 1 of age or later, preferably but not later than at week 8 of age an effective amount of the polypeptide of the present invention. According to a preferred embodiment, less than 20 µg/dose polypeptide of the present invention are required to confer immunity in such animal. According to a more preferred embodiment, the polypeptide of the present invention, preferably less than a 20 µg/dose thereof is only administered once to the animal in need of such treatment.

According to a further, more general aspect, the present invention provides a method for the treatment or prevention of a PCV2 infection or for reduction of clinical signs caused by or associated with a PCV2 infection in young animals, comprising the step of administering an effective amount of the polypeptide of the present invention to that animal in need of such treatment.

The term "young animal" as used herein refers to an animal of 1 to 22 days of age. Preferably, by the term young animal, an animal of 1 to 20 days of age is meant. More preferably, the term young animal refers to an animal of 1 to 15 days of age, even more preferably of 1 day of age to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, most preferably to an animal of 1 day of age. Thus according to a further aspect, the present invention provides a method for the treatment or prevention of a PCV2 infection or for reduction of clinical signs caused by or associated with a PCV2 infection in young animals, comprising the step of administering an effective amount of the polypeptide of the present invention to an animal of 1 to 22 days of age, preferably of 1 to 20 days of age, more preferably of 1 to 15 days of age, even more preferably of 1 to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, most preferably at 1 day of age in need of such treatment. For example, the vaccination/treatment on 19 to 22 days of age preferably shows high efficacy of vaccination. Moreover, vaccination/treatment at 12 to 18, preferably 12 to 14 days of age is preferably very effective in reduction of clinical signs associated with PCV2 infections, reduction of overall viral load, reduction of duration of viremia, delay in onset of viremia, weight gain. Moreover, vaccination at 1 week of age is preferably very effective in reduction of clinical signs associated with PCV2 infections, reduction of overall viral load, reduction of duration of viremia, delay in onset of viremia, weight gain. Preferably less than 20 µg/dose of the polypeptide of the present invention is required to confer immunity in those young animals. According to a more preferred embodiment, the polypeptide of the present invention, preferably less than 20 µg is only administered once to that young animal in need of such treatment.

Due to the ubiquity of PCV2 in the field most of the young piglets are seropositive in respect to PCV2. Thus according to a further aspect, the present invention provides a method for the treatment or prevention of a PCV2 infection or for reduction of clinical signs caused by or associated with a PCV2 infection in young animals, preferably animals having anti-PCV2 antibodies at the day of vaccination, comprising the step of administering an effective amount of the polypeptide of the present invention to an animal of 1 to 22 days of age, preferably of 1 to 20 days of age, more preferably of 1 to 15 days of age, even more preferably of 1 to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably at 1 or 2 day(s) of age, most preferably at 1 day of age in need of such treatment. Preferably, said young animals, at the day of vaccination/treatment, have a detectable anti-PCV2 antibody titer of up to 1:100, preferably of more than 1:100, even more preferably of more than 1:250, even more preferably of more than 1:500, even more preferably of 1:640, even more preferably of more than 1:750, most preferably of more than 1:1000 at the day of vaccination/treatment. Preferably less than 20 µg/dose of the polypeptide of the present invention are required to confer a sufficient immunity in those young animals. According to more preferred embodiment, the polypeptide of the present invention, preferably less than 20 µg is only administered once to that young animal in need of such treatment.

As described above, vaccination/treatment of young animals with the polypeptide of the present invention preferably results in shortening of viremic phase as compared to non-vaccinated control animals. The average shortening time may preferably, for instance, be 9.5 days as compared to non-vaccinated control animals of the same species. Therefore, according to a further aspect, the present invention also provides a method for the treatment or prevention of a PCV2 infection or for reduction of clinical signs caused by or associated with a PCV2 infection in young animals, comprising the step of administering an effective amount of the polypeptide of the present invention to that animal in need of such treatment, wherein the treatment or prevention results in shortening of the viremia phase of 5 or more days, preferably 6 or more days, even more preferably of 7 or more days, even more preferably of 8 or more days, even more preferably of 9, even more preferably of 10, even more preferably of 12, even more preferably of 14, most preferably of more than 16 days as compared to animals of a non-treated control group of the same species. In some cases, the viremic phase is preferably shortening for more than 20 days. In general, the vaccination of young piglets preferably results in a reduction in the loss of weight gain, a shorter duration of viremia, an earlier end to viremia, and a lower virus load. Therefore, according to a further aspect, the present invention provides a method for the treatment or prevention of a PCV2 infection or for reduction of clinical signs caused by or associated with a PCV2 infection in young animals, comprising the step of administering an effective amount of the polypeptide of the present invention to that animal in need of such treatment, wherein said treatment or prevention of PCV2 infection results in an improvement in comparison to animals of a non-treated control group of the same species in a vaccine efficacy parameter selected from the group consisting of a reduction in the loss of weight gain, a shorter duration of viremia, an earlier end to viremia, a lower virus load, or combinations thereof. Preferably less than 20 µg/dose polypeptide of the present invention are required to cause any of the improved vaccine efficacy parameter mentioned above. Moreover such improved vaccine efficacy parameter are achieved by a singly administration of only one dose.

The term "an effective amount" as used herein means but is not limited to an amount of the polypeptide of the present invention, that elicits or is able to elicit an immune response in an animal, to which said effective dose of the polypeptide of the present invention is administered. Preferably, an effective amount is defined as an amount of the polypeptide of the present invention that confers at least a 10 weeks duration of immunity (DOI), preferably at least a 12 weeks (DOI), more preferably at least a 15 weeks (DOI), most preferably at least a 20 weeks (DOI).

The amount that is effective depends on the ingredients of the vaccine and the schedule of administration. Typically, when an inactivated virus or a modified live virus preparation is used in the combination vaccine, an amount of the vaccine containing about $10^{2.0}$ to about $10^{9.0}$ TCID$_{50}$ per dose, preferably about $10^{3.0}$ to about $10^{8.0}$ TCID$_{50}$ per dose, more preferably, about $10^{4.0}$ to about $10^{8.0}$ TCID$_{50}$ per dose. In particular, when modified live PCV2 is used in the vaccines, the recommended dose to be administered to the susceptible animal is preferably about $10^{3.0}$ TCID$_{50}$ (tissue culture infective dose 50% end point)/dose to about $10^{6.0}$ TCID$_{50}$/dose and more preferably about $10^{4.0}$ TCID$_{50}$/dose to about $10^{5.0}$ TCID$_{50}$/dose. In general, the quantity of antigen will be between 0.2 and 5000 micrograms, and between $10^{2.0}$ and $10^{9.0}$ TCID$_{50}$, preferably between $10^{3.0}$ and $10^{6.0}$ TCID$_{50}$, more preferably between $10^{4.0}$ and $10^{5.0}$ TCID$_{50}$, when purified antigen is used.

Sub-unit vaccines are normally administered with an protein inclusion level of at least 0.2 µg protein per dose, preferably with about 0.2 to about 400 µg/dose, still more preferably with about 0.3 to about 200 µg/dose, even more preferably with about 0.35 to about 100 µg/dose, still more preferably with about 0.4 to about 50 µg/dose, still more preferably with about 0.45 to about 30 µg/dose, still more preferably with about 0.5 to about 18 µg/dose, still more preferably with about 0.6 to about 16 µg/dose, even more preferably with about 0.75 to about 8 µg/dose, even more preferably with about 1.0 to about 6 µg/dose, still more preferably with about 1.3 to about 3.0 µg/dose.

Preferably, the prophylactic use of the immunogenic compositions described supra, is effective for reduction of clinical signs caused by or associated with PCV2 infections, preferably in young animals and/or in animals having passive immunity against PCV2 at the day of treatment. In particular, the prophylactic use of the immunogenic compositions as described herein, and specifically of compositions comprising the polypeptide of the present invention, is preferably effective for reducing lymphadenopathy, lymphoid depletion and/or multinucleated/giant histiocytes in animals infected with PCV2 and having maternal anti-PCV-2 antibodies at the day of treatment/vaccination. For example it was discovered that the prophylactic use of the immunogenic compositions as described herein is effective for reducing lymphoid depletion, lymphoid inflammation, positive IHC for PCV2 antigen of lymphoid tissue, viremia, nasal shedding, pyrexia, reduced average daily weight gain, lung inflammation, positive IHC for PCV2 antigen of lung tissue.

Furthermore, the prophylactic use of the immunogenic compositions as described herein is preferably effective for reducing (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc., (7) Pia like lesions, normally known to be associated with Lawsonia intracellularis infections (leitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14) reduced growth variability (15), reduced frequency of 'runts' (16), reduced co-infections with Porcine Reproductive and Respiratory Disease Complex (PRRSV). Such immunogenic composition is also effective in improving economically important growth parameters such as time to slaughter, carcass weight, and lean meat ratio. Thus the term "clinical signs" as used herein, means, but is not limited to (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc., (7) Pia-like lesions, normally known to be associated with Lawsonia intracellularis infections (Ileitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14) reduced growth variability (15) reduced frequency of 'runts' (16) reduced co-infections with Porcine Reproductive and Respiratory Disease Complex (PRRSV), (17) lymphoid inflammation, (18) positive IHC for PCV2 antigen of lymphoid tissue, (19) viremia, (20) nasal shedding, (21) pyrexia, (22) reduced average daily weight gain, (23) lung inflammation, (24) positive IHC for PCV2 antigen of lung tissue. Moreover, the immunogenic composition described herein reduces the overall circovirus load including a later onset, a shorter duration, an earlier end of viremia, and a reduced viral load and its immunosuppressive impact in young animals, in particular in those having anti-PCV2 antibodies at the day of vaccination, thereby resulting in a higher level of general disease resistance and a reduced incidence of PCV2 associated diseases and clinical signs.

Thus, according to a further aspect, the present invention provides a method for the treatment or prevention of a PCV2 infection or for reduction of clinical signs caused by or associated with a PCV2 infection in young animals and/or in animals, preferably animals having anti-PCV2 antibodies, comprising the step of administering an effective amount of the polypeptide of the present invention or an immunogenic composition comprising the polypeptide of the present invention to that animal in need of such treatment, wherein those clinical signs are selected from the group consisting of: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc., (7) Pia-like lesions, normally known to be associated with Lawsonia intracellularis infections (leitis), (8) lymphadenopathy, (9) lymphoid depletion and/or (10) multinucleated/giant histiocytes (11), Porcine Dermatitis and Nephropathy Syndrome (PDNS), (12) PCVAD associated mortality, (13) PCVAD associated weight loss, (14) reduced growth variability (15) reduced frequency of 'runts', (16) reduced co-infections with Porcine Reproductive and Respiratory Disease Complex (PRRSV), (17) lymphoid inflammation, (18) positive IHC for PCV2 antigen of lymphoid tissue, (19) viremia, (20) nasal shedding, (21) pyrexia, (22) reduced average daily weight gain, (23) lung inflammation, (24) positive IHC for PCV2 antigen of lung tissue. According to a further aspect, the present invention provides a method for the treatment or prevention of a PCV2 infection or for reduction of clinical signs caused by or associated with a PCV2 infection in young animals, comprising the step of administering an effective amount of the polypeptide of the present invention to that animal in need of such treatment, wherein those clinical signs are selected from the group consisting of: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc., (7) Pia-like lesions, normally known to be associated with Lawsonia intracellularis infections (Ileitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14) reduced growth variability (15) reduced frequency of 'runts' (16) reduced co-infections with Porcine Reproductive and Respiratory Disease Complex (PRRSV), (17) lymphoid inflammation, (18) positive IHC for PCV2 antigen of lymphoid tissue, (19) viremia, (20) nasal shedding, (21) pyrexia, (22) reduced average daily weight gain, (23) lung inflammation, (24) positive IHC for PCV2 antigen of lung tissue.

The composition according to the invention may be applied, orally, intradermally, intratracheally, or intravaginally. The composition preferably may be applied intramuscularly or intranasally, most preferably intramuscularly. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the invention may be administered once or several times, also intermittently, for instance on a daily basis for several days, weeks or months and in different dosages.

Preferably, one dose of the immunogenic composition as described above is intramuscularly administered to the subject in need thereof. According to a further aspect, the polypeptide of the present invention or the immunogenic composition comprising any such polypeptide of the present invention as described herein is bottled in and administered at one (1) mL per dose. Thus, according to a further aspect, the present invention also provides a 1 ml immunogenic composition, comprising the polypeptide of the present invention as described herein, for the treatment or prevention of a PCV2 infection or for reduction of clinical signs caused by or associated with a PCV2 infection in young animals, comprising the step of administering an effective amount of the polypeptide of the present invention protein to that animal in need of such treatment. According to a further aspect, the present invention also provides a 1 ml immunogenic composition, comprising the polypeptide of the present invention as described herein, for the treatment or prophylaxis of a PCV2 infection or for reduction of clinical signs caused by or associated with a PCV2 infection in animals, preferably animals having anti-PCV2 antibodies, comprising the step of administering an effective amount of the polypeptide of the present invention or an immunogenic composition comprising the polypeptide of the present invention to that animal in need of such treatment.

According to a further aspect, at least one further administration of at least one dose of the immunogenic composition as described above is given to a subject in need thereof, wherein the second or any further administration is given at least 14 days beyond the initial or any former administrations. Preferably, the immunogenic composition is administered with an immune stimulant. Preferably, said immune stimulant is given at least twice. Preferably, at least 3 days, more preferably at least 5 days, even more preferably at least 7 days are in between the first and the second or any further administration of the immune stimulant. Preferably, the immune stimulant is given at least 10 days, preferably 15 days, even more preferably 20, even more preferably at least 22 days beyond the initial administration of the immunogenic composition provided herein. A preferred immune stimulant is, for example, keyhole limpet hemocyanin (KLH), preferably emulsified with incomplete Freund's adjuvant (KLH/ICFA). However, it is herewith understood, that any other immune stimulant known to a person skilled in the art can also be used. The term "immune stimulant" as used herein, means any agent or composition that can trigger the immune response, preferably without initiating or increasing a specific immune response, for example the immune response against a specific pathogen. It is further instructed to administer the immune stimulant in a suitable dose.

DETAILED DESCRIPTION OF THE PREFERRED EMBODIMENTS

The following examples set forth preferred materials and procedures in accordance with the present invention. Although any methods and materials similar or equivalent to those described herein can be used in the practice or testing of the present invention, the preferred methods, devices, and materials are now described. It is to be understood, however, that these examples are provided by way of illustration only, and nothing therein should be deemed a limitation upon the overall scope of the invention.

Example 1

Materials & Procedure/Design of Mutants

The PCV2a ORF2 amino acid sequence of the PCV2 ORF2 protein included in the product CIRCOFLEX® was aligned with the PCV2b ORF2 BDH amino acid sequence and a number of other published PCV2a and PCV2b ORF2 amino acid sequences from Genbank using the Clustal W method. Positions of major amino acid differences between PCV2a and PCV2b ORF2 sequences were identified as potential positions for mutation (see FIG. 1). Using the identified major amino acid changes, seven PCV2b ORF2 coding sequences were prepared exchanging the amino acid from PCV2b ORF2 BDH for the corresponding amino acid from PCV2a ORF2. PCV2a ORF2 (CIRCOFLEX) codons were used to code for the mutant amino acids. The seven PCV2b ORF2 mutant constructs are detailed below:
1. PCV2b ORF2 BDH K59A
2. PCV2b ORF2 BDH R63T
3. PCV2b ORF2 BDH R63K
4. PCV2b ORF2 BDH SFCO P88K T151P**
5. PCV2b ORF2 BDH G191R
6. PCV2b ORF2b BDH I206K
7. PCV2b ORF2 BDH N232E All coding sequences were synthesized at Integrated DNA Technologies except #4 which was created by site-directed mutagenesis of a synthesized PCV2b ORF2b BDH SFCO coding sequence.

** SFCO=codon optimized for *Spodoptera frugiperda*. This construct was created prior to the alignment described above through a preliminary sequence assessment. The two mutations were also identified in this sequence assessment.

Preparation of Mutant PCV2b ORF2 Baculovirus

Each of the seven PCV2b ORF2 mutant coding sequences, as well as the unmutated PCV2b ORF2 BDH coding sequence, were cloned into baculovirus transfer vector pVL1393 and co-transfected with baculovirus DNA in Sf9 cells. Each resulting recombinant baculovirus was checked for PCV2b ORF2 expression by IFA. Amplified stocks of each recombinant baculovirus were prepared on Sf+ cells and titrated via the $TCID_{50}$ method to determine the baculoviral titer.

Expression Evaluation of Mutant PCV2b ORF2 Baculovirus

Figure 3:
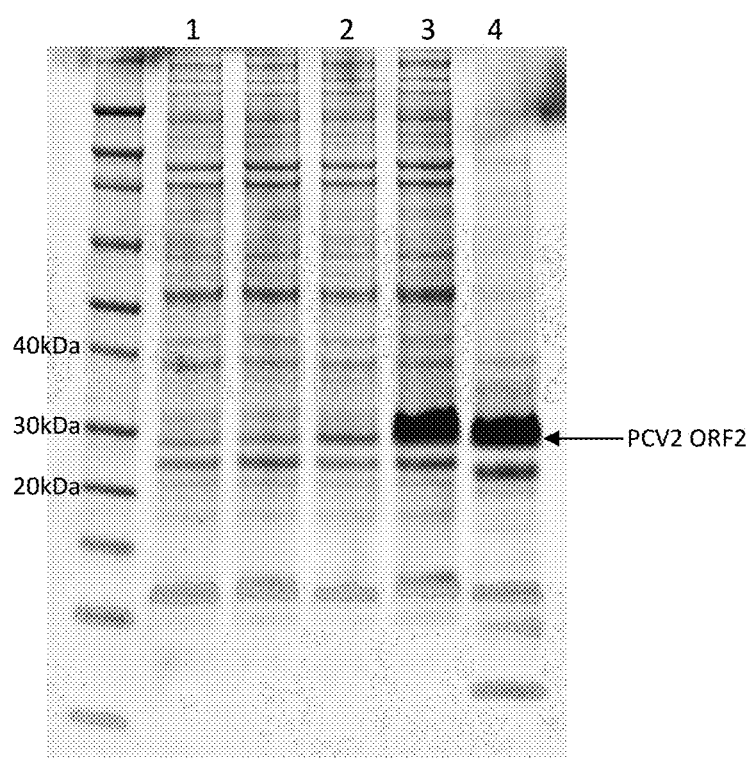
FIG. 3—Evaluation of 100,000 g pellets for PCV2b ORF2. Lane 1=PCV2b ORF2 BDH, Lane 2=PCV2b ORF2 BDH R63K, Lane 3=PCV2b ORF2 BDH R63T, Lane 4=Circoflex WSV (PCV2a ORF2).
Figure 4:
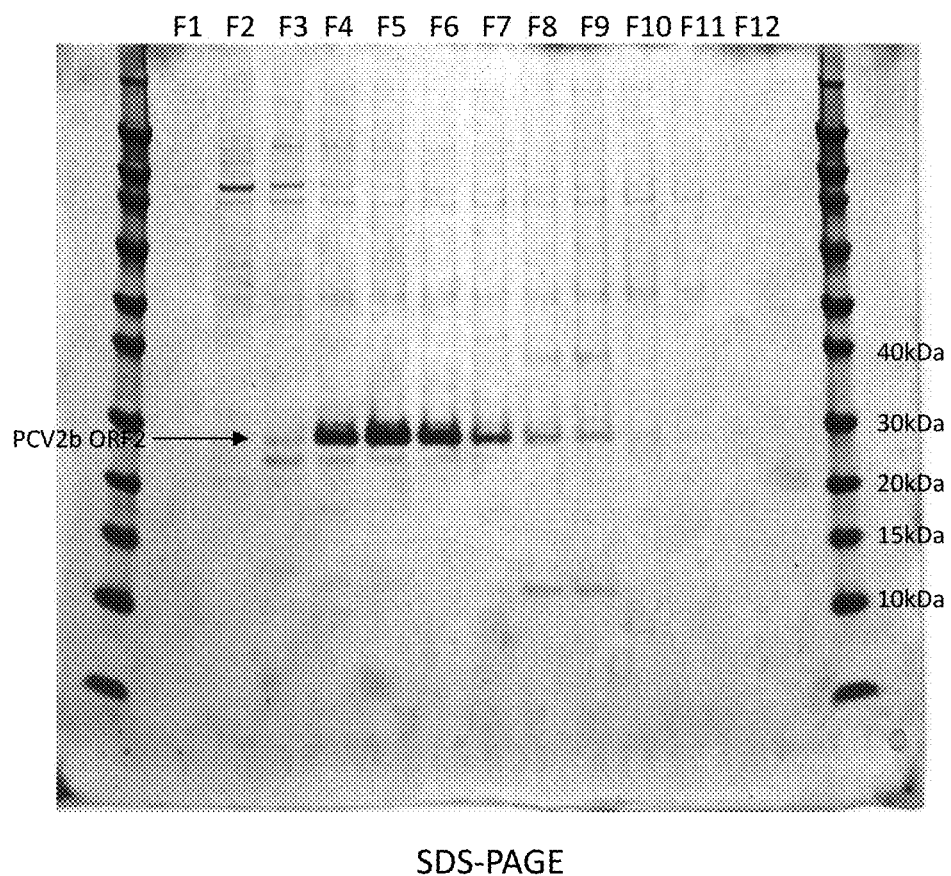
FIG. 4—SDS-PAGE separation of sucrose gradient fractions. F1-F12=Fractions 1-12.

Each recombinant baculovirus was evaluated for expression of its PCV2b ORF2 coding sequence by infecting Sf+ cells at a target MOI of 0.1. The infections were allowed to progress for 5-7 days then were harvested by centrifugation at 20,000 g for 20 min to remove cellular debris and insoluble protein. The harvest supernatants were 0.2 µm filtered and evaluated directly for PCV2b ORF2 expression by western blot using α-PCV2 antibodies (e.g. FIG. 2). The harvest supernatants were also evaluated for the presence of macromolecular structures. Briefly, a sample of each harvest supernatant was centrifuged at 100,000 g for two hours. The resulting pellets were resuspended in a small volume of TBS and separated by SDS-PAGE. PCV2b ORF2 bands were detected in stained gels by size comparison to PCV2a ORF2 (e.g. FIG. 3). Resuspended pellets were also separated on a 10%-60% discontinuous sucrose gradient by centrifugation at 100,000 g for two hours to partially purify the PCV2b ORF2 proteins for quantitation and VLP confirmation by electron microscopy (EM) (e.g., FIG. 4).

Figure 5B:
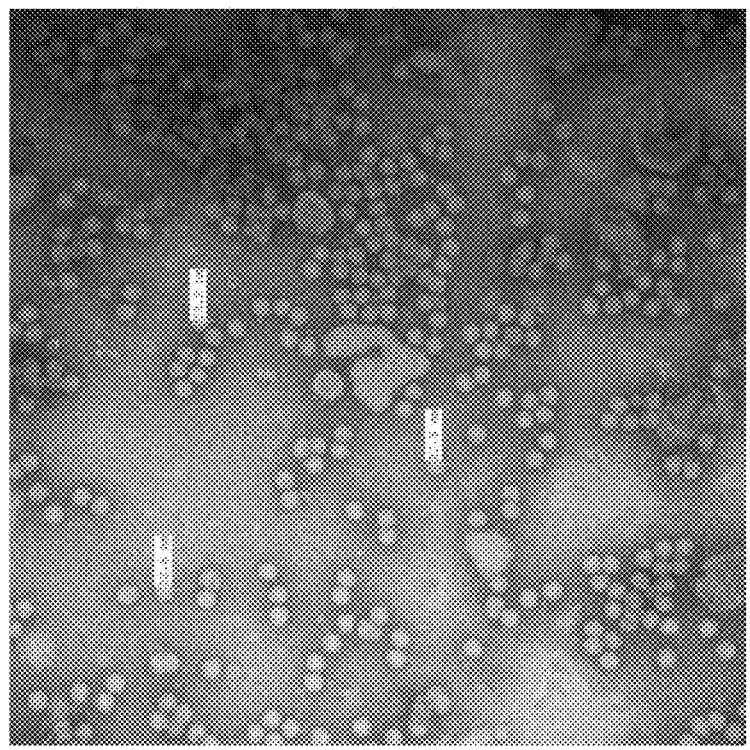
FIG. 5A and FIG. 5B—Confirmation of VLP formation by EM
Figure 5A:
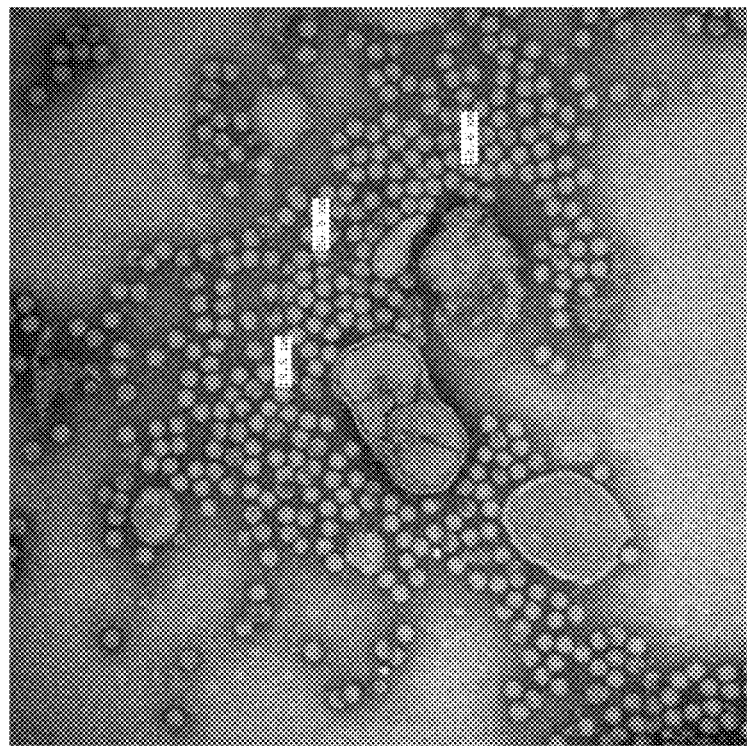

After sucrose gradient separation, the PCV2b ORF2 containing fractions were pooled and the PCV2b ORF2 concentration was determined by SDS-PAGE gel densitometry compared to a BSA standard curve. In addition, a sample of the sucrose gradient-purified material was further concentrated and submitted for VLP confirmation by EM using phosphotungstic acid as a negative stain (e.g., FIG. 5).

A table of the results from the evaluation of the PCV2b ORF2 BDH mutant constructs is shown in FIG. 6. The results demonstrated that a single amino acid mutation from arginine to threonine at position 63 increased expression of PCV2b ORF2 BDH in Sf+ cells nearly ten-fold. The single R63T mutation increased PCV2b ORF2 BDH expression in Sf+ cells to levels similar to PCV2a ORF2. An analysis of the amino acid sequence of PCV2b ORF2 BDH suggests that the BC loop may be susceptible to cleavage by trypsin-like proteases. Structural data published by Khayat et al. in 2011 suggests that arginine 63 is on the BC loop that projects out furthest from the PCV2 viral capsid formed by the ORF2 protein, leaving it susceptible to proteases released after the lysis of Sf+ cells during baculovirus replication.

In addition to threonine substitution at position 63, in another embodiment of the invention the arginine is substituted by other uncharged polar amino acids including serine, tyrosine, asparagine and glutamine to obtain the same stabilizing effect. In addition, nonpolar amino acids including glycine, alanine, valine, leucine, isoleucine, phenylalanine and tryptophan may achieve the same effect as well.

Example 2

This study demonstrates the efficacy of one embodiment of the Porcine Circovirus Type 2 ORF2b Vaccine against a PCV2a and/or PCV2b challenge. Cesarean-derived colostrum-deprived (CDCD) piglets are used in this study and separated into 2 groups; 1) pigs vaccinated with an experimental Porcine Circovirus Vaccine including the PCV2b ORF2 R63T variant of Example 1 (Killed Baculovirus Vector) that are challenged with virulent PCV2b and, 2) non-vaccinated challenged control pigs that are challenged with virulent PCV2b. On Day 0, Group 1 is administered 1 mL of vaccine intramuscularly (IM) whereas Group 2, non-vaccinated challenge control pigs do not receive any treatment. On Day 28, all pigs in groups 1 and 2 are challenged with virulent PCV2b 1 mL intranasally (IN) and 1 mL IM with an approximate dosage of 3.0 $\text{Log}_{10}$ $\text{TCID}_5$/mL of live virus. All pigs receive 2.0 mL Keyhole Limpet Hemocyanin emulsified in Incomplete Freunds Adjuvant (KLH/ICFA) IM on Days 25 and 31. Pigs are monitored daily for clinical signs, and blood is drawn for serologic testing periodically. On Day 56 all pigs are necropsied and select tissues are collected and gross pathology observations are made.

As a whole, vaccinated animals exhibit reduction when compared to their respective challenge control group in all parameters tested.

Example 3

Several other substitutions at amino acid site 63 were produced to compare to the PCV2b ORF BDH native strain. The results from the evaluation of the PCV2b ORF2 BDH mutant constructs are shown in FIGS. 7A and 7B. The results demonstrate that in addition to the amino acid mutation from arginine (R) to threonine (T) at position 63, arginine (R) 63 to glycine (G), arginine (R) 63 to glutamine (Q), and arginine (R) 63 to aspartate (D) increased the expression of PCV2b ORF2 BDH in Sf+ cells at least Four-fold as compared to the wild type. In particular the single mutations R63G and R63Q increased PCV2b ORF2 BDH expression in Sf+ cells to levels similar to PCV2a ORF2.

Generation of Recombinant Baculovirus Encoding PCV2b ORF2 R63 Mutants

Point mutations in the coding sequence of PCV2b ORF2 at amino acid position 63 were generated by site-directed mutagenesis. Briefly, baculovirus transfer plasmid pVL1393-PCV2b ORF2 was subjected to site-directed mutagenesis using primers in Table 1. The resulting baculovirus transfer vectors were sequenced to confirm proper mutation of the coding sequence and then co-transfected with linearized baculovirus DNA into Sf9 cells. Co-transfections were harvested after 5 days and evaluated for PCV2b ORF2 expression by IFA using PCV2-specific antibodies. Amplified stocks of each baculovirus were generated on Sf9 cells and titered via an IFA-based $\text{TCID}_{50}$ method using an α-baculovirus gp64 monoclonal antibody.

TABLE 1

Primers for site-directed mutagenesis.

| Primer | Sequence |
|---|---|
| Forward | 5'-CTGTCAAGAAAACCACAGTCX$^1$X$^2$X$^3$ACGCCCTCC TGGAATGTG-3' |
| Reverse | Reverse complement of Forward |

| Mutation | X$^1$ | X$^2$ | X$^3$ |
|---|---|---|---|
| R63D | G | A | C |
| R63Q | C | A | G |
| R63G | G | G | A |
| R63L | T | T | G |
| R63T | A | C | A |

Expression and Quantitation of PCV2b ORF2 VLPs

SF+ cells in spinner flasks were infected with recombinant baculovirus at an MOI of 0.1 and incubated at 27° C. with constant agitation at approximately 100 rpm. Infected cultures were harvested once SF+ cell viability dropped below 30% or at 7 days post infection. Raw baculovirus harvests were centrifuged at 20,000 g for 20 minutes at 4° C. to pellet cells and insoluble debris and then 0.2 μm filtered. Clarified baculovirus harvest fluids (35 mL) were subjected to centrifugation at 100,000 g RCF for 2 hours at 4° C. to pellet PCV2b ORF2 VLPs. The resulting pellets were resuspended in TBS and further separated on a 10%-60% discontinuous sucrose gradient at 100,000 g RCF for 2 hrs at 4° C. The fractions containing the majority of the PCV2b ORF2, as determined by SDS-PAGE and Western blot utilizing 0-PCV2 antibodies, were pooled and evaluated by densitometry. Briefly, pooled PCV2b ORF2-containing fractions were separated by SDS-PAGE and stained with SIMPLYBLUE™ Safe Stain. Gel images were captured and analyzed using an Alpha View camera and software. The mass of PCV2b ORF2 bands were calculated using a BSA standard curve included on each gel. The PCV2b ORF2 concentration of the pool was calculated by dividing the mass of the PCV2b ORF2 band(s) by the total volume of sample loaded on the gel. PCV2b ORF2 concentrations in harvest material were calculated by multiplying the PCV2b ORF2 concentration in the pool by the volume of the pool and then dividing the result by the starting volume of harvest fluids used for centrifugation.

Example 4

This study evaluates the efficacy of Porcine Circovirus Type 2 ORF2b Prototype Vaccine (including recombinant baculovirus expressed PCV2b ORF2 protein of SEQ ID NO: 1) against a PCV2b challenge when given at three weeks of age.

Forty two healthy CDCD pigs (X pigs from each of X litters and X pigs from each of X litters) were blocked and housed amongst six pens. Pigs within a pen were equally randomized to 1 of 5 treatment groups: Group 1 (Strict Negative Controls) consisted of X pigs and received no treatment, Group 2 (Challenge Controls, n=X) received no treatment, Group 3 (Experimental PCV2b comprising SEQ ID NO: 1+ carbopol vaccine, n=X), Group 4 (Experimental PCV2b comprising SEQ ID NO: 1+ISA207VG vaccine, n=X). An overview of the treatment groups is provided in Table 2.

TABLE 2

| Group | No. of Pigs | Treatment | Day 0 | Day 11 and Day 17 | Day 14 | Day 42 |
|---|---|---|---|---|---|---|
| 1 | ≥5 | Strict Neg Cont | n/a | n/a | Necropsy | n/a |
| 2 | ≥20 | Challenge Control | n/a | KLH/ICFA Treatment | PCV2b challenge | Necropsy |
| 3 | ≥20 | PCV2b ORF2 protein + Carbopol | Vaccinate | KLH/ICFA Treatment | PCV2b challenge | Necropsy |
| 4 | >20 | PCV2b ORF2 protein + ISA207VG | Vaccinate | KLH/ICFA Treatment | PCV2b challenge | Necropsy |
| 5 | ≥20 | PCV2a/ PCV2b ORF2 protein + Carbopol | Vaccinate | KLH/ICFA Treatment | PCV2b challenge | Necropsy |

On D0 pigs were 24 days of age and Group 3 pigs are administered a 1 mL dose of vaccine intramuscularly (IM). On D11 and D17, all pigs receive a 2.0 mL dose of KLH/ICFA, intramuscularly (IM). On D14 all pigs are challenged with approximately 5.0 $\log_{10}$ $TCID_{50}$/mL of live virulent PCV2b 1.0 mL IM in the right neck and 1.0 mL intranasally. Pigs are examined daily for overall health. Blood samples are collected on D-4, D14, D21, D28, D33 and D42, and sera were tested for PCV2 viremia by quantitative real time polymerase chain reaction on all days with the exception of Day −4. Animals vaccinated show significantly lower viremia and reduced to no clinical symptoms compared to non-vaccinated animals after the PCV2b challenge.

Within the context of the invention made and the experimental data provided herewith, in particular the following was considered:

- with respect to lymphoid depletion: to support evidence of "aid in the prevention of lymphoid depletion", a pig was considered positive if one or more of the 4 lymphoid tissue samples (tonsil, TBLN, MLN or ILN) was histologically positive for lymphoid depletion;
- with respect to lymphoid inflammation: to support evidence of "aid in the prevention of lymphoid inflammation", a pig was considered positive if one or more of the 4 lymphoid tissue samples (tonsil, TBLN, MLN or ILN) was histologically positive for lymphoid inflammation;
- with respect to lymphoid colonization: to support evidence that pigs cleared infection by 4 weeks post-virus exposure, a pig was considered positive if one or more of the 4 lymphoid tissue samples (tonsil, TBLN, MLN or ILN) was positive for PCV2 lymphoid colonization by IHC;
- with respect to viremia: to support evidence of "aid in the prevention of viremia", a pig was considered positive on the day of sampling if the serum rt-PCR test was ≥1.0×104 PCV2 genomic equivalents (the linear lower level); and
- with respect to mortality: to support evidence of "aid in the prevention of mortality", a pig was considered positive for mortality if it succumbed to challenge (died or required euthanasia for humane reasons with attributable clinical signs, gross lesions and/or histological lesions consistent with PCV2).

In the Sequence Listing:

- SEQ ID NO: 1 corresponds to SEQ ID NO: 2 including the substitution R63T.
- SEQ ID NO: 2 corresponds to the sequence of a wild type PCV2b ORF2 protein.
- SEQ ID NO: 3 corresponds to the sequence of a wild type PCV2a ORF2 protein.
- SEQ ID NO: 4 corresponds to a polynucleotide sequence encoding SEQ ID NO: 1.
- SEQ ID NO: 5 corresponds to the sequence of a wild type PCV2b ORF2 protein.
- SEQ ID NO: 6 corresponds to the sequence of a polypeptide of the present invention being 233 amino acid residues in length and having at amino acid position 59 an arginine residue.
- SEQ ID NO:7 corresponds to the sequence of a polypeptide of the present invention being 233 amino acid residues in length and having at amino acid position 59 a lysine residue.
- SEQ ID NO:8 corresponds to the sequence of a polypeptide of the present invention being 234 amino acid residues in length and having at amino acid position 59 an arginine residue.
- SEQ ID NO:9 corresponds to the sequence of a polypeptide of the present invention being 234 amino acid residues in length and having at amino acid position 59 a lysine residue.
- SEQ ID NO:10 corresponds to the sequence of amino acid positions 58-66 (also referred to as "BC-loop" herein) of a polypeptide of the present invention having at amino acid position 59 an arginine residue and having at amino acid position 63 an alanine residue.
- SEQ ID NO:11 corresponds to the sequence of amino acid positions 58-66 (also referred to as "BC-loop" herein) of a polypeptide of the present invention having at amino acid position 59 an arginine residue and having at amino acid position 63 a cysteine residue.
- SEQ ID NO:12 corresponds to the sequence of amino acid positions 58-66 (also referred to as "BC-loop" herein) of a polypeptide of the present invention having at amino acid position 59 an arginine residue and having at amino acid position 63 an aspartate residue.
- SEQ ID NO:13 corresponds to the sequence of amino acid positions 58-66 (also referred to as "BC-loop" herein) of a polypeptide of the present invention having at amino acid position 59 an arginine residue and having at amino acid position 63 a glutamate residue.
- SEQ ID NO:14 corresponds to the sequence of amino acid positions 58-66 (also referred to as "BC-loop" herein) of a polypeptide of the present invention having at amino acid position 59 an arginine residue and having at amino acid position 63 a phenylalanine residue.
- SEQ ID NO:15 corresponds to the sequence of amino acid positions 58-66 (also referred to as "BC-loop" herein) of a polypeptide of the present invention having at amino acid position 59 an arginine residue and having at amino acid position 63 a glycine residue.
- SEQ ID NO:16 corresponds to the sequence of amino acid positions 58-66 (also referred to as "BC-loop" herein) of a polypeptide of the present invention having at amino acid position 59 an arginine residue and having at amino acid position 63 a histidine residue.
- SEQ ID NO:17 corresponds to the sequence of amino acid positions 58-66 (also referred to as "BC-loop" herein)

of a polypeptide of the present invention having at amino acid position 59 an arginine residue and having at amino acid position 63 an isoleucine residue.

SEQ ID NO:18 corresponds to the sequence of amino acid positions 58-66 (also referred to as "BC-loop" herein) of a polypeptide of the present invention having at amino acid position 59 an arginine residue and having at amino acid position 63 a leucine residue.

SEQ ID NO:19 corresponds to the sequence of amino acid positions 58-66 (also referred to as "BC-loop" herein) of a polypeptide of the present invention having at amino acid position 59 an arginine residue and having at amino acid position 63 a methionine residue.

SEQ ID NO:20 corresponds to the sequence of amino acid positions 58-66 (also referred to as "BC-loop" herein) of a polypeptide of the present invention having at amino acid position 59 an arginine residue and having at amino acid position 63 an asparagine residue.

SEQ ID NO:21 corresponds to the sequence of amino acid positions 58-66 (also referred to as "BC-loop" herein) of a polypeptide of the present invention having at amino acid position 59 an arginine residue and having at amino acid position 63 a proline residue.

SEQ ID NO:22 corresponds to the sequence of amino acid positions 58-66 (also referred to as "BC-loop" herein) of a polypeptide of the present invention having at amino acid position 59 an arginine residue and having at amino acid position 63 a glutamine residue.

SEQ ID NO:23 corresponds to the sequence of amino acid positions 58-66 (also referred to as "BC-loop" herein) of a polypeptide of the present invention having at amino acid position 59 an arginine residue and having at amino acid position 63 a serine residue.

SEQ ID NO:24 corresponds to the sequence of amino acid positions 58-66 (also referred to as "BC-loop" herein) of a polypeptide of the present invention having at amino acid position 59 an arginine residue and having at amino acid position 63 a threonine residue.

SEQ ID NO:25 corresponds to the sequence of amino acid positions 58-66 (also referred to as "BC-loop" herein) of a polypeptide of the present invention having at amino acid position 59 an arginine residue and having at amino acid position 63 a valine residue.

SEQ ID NO:26 corresponds to the sequence of amino acid positions 58-66 (also referred to as "BC-loop" herein) of a polypeptide of the present invention having at amino acid position 59 an arginine residue and having at amino acid position 63 a tryptophan residue.

SEQ ID NO:27 corresponds to the sequence of amino acid positions 58-66 (also referred to as "BC-loop" herein) of a polypeptide of the present invention having at amino acid position 59 an arginine residue and having at amino acid position 63 a tyrosine residue.

SEQ ID NO:28 corresponds to the sequence of amino acid positions 58-66 (also referred to as "BC-loop" herein) of a polypeptide of the present invention having at amino acid position 59 an arginine residue and having at amino acid position 63 an alanine residue.

SEQ ID NO:29 corresponds to the sequence of amino acid positions 58-66 (also referred to as "BC-loop" herein) of a polypeptide of the present invention having at amino acid position 59 a lysine residue and having at amino acid position 63 a cysteine residue.

SEQ ID NO:30 corresponds to the sequence of amino acid positions 58-66 (also referred to as "BC-loop" herein) of a polypeptide of the present invention having at amino acid position 59 a lysine residue and having at amino acid position 63 an aspartate residue.

SEQ ID NO:31 corresponds to the sequence of amino acid positions 58-66 (also referred to as "BC-loop" herein) of a polypeptide of the present invention having at amino acid position 59 a lysine residue and having at amino acid position 63 a glutamate residue.

SEQ ID NO:32 corresponds to the sequence of amino acid positions 58-66 (also referred to as "BC-loop" herein) of a polypeptide of the present invention having at amino acid position 59 a lysine residue and having at amino acid position 63 a phenylalanine residue.

SEQ ID NO:33 corresponds to the sequence of amino acid positions 58-66 (also referred to as "BC-loop" herein) of a polypeptide of the present invention having at amino acid position 59 a lysine residue and having at amino acid position 63 a glycine residue.

SEQ ID NO:34 corresponds to the sequence of amino acid positions 58-66 (also referred to as "BC-loop" herein) of a polypeptide of the present invention having at amino acid position 59 a lysine residue and having at amino acid position 63 a histidine residue.

SEQ ID NO:35 corresponds to the sequence of amino acid positions 58-66 (also referred to as "BC-loop" herein) of a polypeptide of the present invention having at amino acid position 59 a lysine residue and having at amino acid position 63 an isoleucine residue.

SEQ ID NO:36 corresponds to the sequence of amino acid positions 58-66 (also referred to as "BC-loop" herein) of a polypeptide of the present invention having at amino acid position 59 a lysine residue and having at amino acid position 63 a leucine residue.

SEQ ID NO:37 corresponds to the sequence of amino acid positions 58-66 (also referred to as "BC-loop" herein) of a polypeptide of the present invention having at amino acid position 59 a lysine residue and having at amino acid position 63 a methionine residue.

SEQ ID NO:38 corresponds to the sequence of amino acid positions 58-66 (also referred to as "BC-loop" herein) of a polypeptide of the present invention having at amino acid position 59 a lysine residue and having at amino acid position 63 an asparagine residue.

SEQ ID NO:39 corresponds to the sequence of amino acid positions 58-66 (also referred to as "BC-loop" herein) of a polypeptide of the present invention having at amino acid position 59 a lysine residue and having at amino acid position 63 a proline residue.

SEQ ID NO:40 corresponds to the sequence of amino acid positions 58-66 (also referred to as "BC-loop" herein) of a polypeptide of the present invention having at amino acid position 59 a lysine residue and having at amino acid position 63 a glutamine residue.

SEQ ID NO:41 corresponds to the sequence of amino acid positions 58-66 (also referred to as "BC-loop" herein) of a polypeptide of the present invention having at amino acid position 59 a lysine residue and having at amino acid position 63 a serine residue.

SEQ ID NO:42 corresponds to the sequence of amino acid positions 58-66 (also referred to as "BC-loop" herein) of a polypeptide of the present invention having at amino acid position 59 a lysine residue and having at amino acid position 63 a threonine residue.

SEQ ID NO:43 corresponds to the sequence of amino acid positions 58-66 (also referred to as "BC-loop" herein) of a polypeptide of the present invention having at amino acid position 59 a lysine residue and having at amino acid position 63 a valine residue.

SEQ ID NO:44 corresponds to the sequence of amino acid positions 58-66 (also referred to as "BC-loop" herein) of a polypeptide of the present invention having at amino acid position 59 a lysine residue and having at amino acid position 63 a tryptophan residue.

SEQ ID NO:45 corresponds to the sequence of amino acid positions 58-66 (also referred to as "BC-loop" herein) of a polypeptide of the present invention having at amino acid position 59 a lysine residue and having at amino acid position 63 a tyrosine residue.

SEQ ID NO:46 corresponds to the sequence of a polypeptide of the present invention being 234 amino acid residues in length and having at amino acid position 63 a threonine residue.

What is claimed is:

1. An immunogenic composition comprising
a modified PCV2 ORF2 protein having
at amino acid position 59 an arginine residue or a lysine residue, and
at amino acid position 88 a proline residue, and
at amino acid position 151 a threonine residue, and
at amino acid position 206 an isoleucine residue, and
at amino acid position 232 an asparagine residue,
and having at amino acid position 63 an amino acid residue other than an arginine residue or a lysine residue,
wherein the numbering of the amino acid positions refers to the amino acid sequence of wild type PCV2 ORF2 protein; and
wherein said immunogenic composition further contains a PCV2a ORF2 polypeptide.

2. The immunogenic composition of claim 1, wherein the modified PCV2 ORF2 protein has at amino acid position 63 an amino acid residue selected from the group consisting of amino acid residue with a polar but uncharged side chain, amino acid residue with a hydrophobic side chain, and glycine residue.

3. The immunogenic composition of claim 2, wherein said amino acid residue with a polar but uncharged side chain is selected from the group consisting of serine residue, threonine residue, tyrosine residue, asparagine residue, and glutamine residue, and/or wherein said amino acid residue with a hydrophobic side chain is selected from the group consisting of alanine residue, valine residue, leucine residue, isoleucine residue, phenylalanine residue, and tryptophan residue.

4. The immunogenic composition of claim 1, wherein the modified PCV2 ORF2 protein having at amino acid position 63 an amino acid residue selected from the group consisting of serine residue and threonine residue.

5. The immunogenic composition of claim 1, wherein the modified PCV2 ORF2 protein containing the at least one mutation in the BC loop is expressed in a baculovirus expression system in a higher amount, or in a higher amount by at least a factor 2, or in a higher amount by at least a factor 3, or in a higher amount by at least a factor 5, or in a higher amount by at least a factor 8 compared to a PCV2 ORF2 protein that does not contain such mutation, and/or the modified PCV2 ORF2 protein containing the at least one mutation in the BC loop is expressed in a higher amount in a baculovirus expression system compared to the modified PCV2 ORF2 protein that does not contain such mutation and/or wherein the modified PCV2 ORF2 protein that does not contain such mutation is a wild type PCV2 ORF2 protein.

6. The immunogenic composition of claim 1, wherein the at least one mutation in the BC loop is at least one mutation in the region of the amino acid positions 58 to 66, and wherein the numbering of the amino acid positions refers to the amino acid sequence of wild type PCV2 ORF2 protein.

7. The immunogenic composition of claim 1, wherein the at least one mutation in the BC loop comprises or consists of a deletion, substitution, and/or an addition of one to 7 amino acid residues in the region of the amino acid positions 60 to 66, and wherein the numbering of the amino acid positions refers to the amino acid sequence of wild type PCV2 ORF2 protein.

8. The immunogenic composition of claim 1, wherein the at least one mutation in the BC loop is a deletion, substitution, and/or an addition of one amino acid residue at amino acid position 63, and wherein the numbering of the amino acid position refers to the amino acid sequence of wild type PCV2 ORF2 protein.

9. The immunogenic composition of claim 1, wherein the at least one mutation in the BC loop is a substitution of the amino acid residue at amino acid position 63 by an amino acid residue other than an arginine residue or a lysine residue, and wherein the numbering of the amino acid position refers to the amino acid sequence of wild type PCV2 ORF2 protein.

10. The immunogenic composition of claim 9, wherein said amino acid residue other than an arginine residue or a lysine residue amino is a naturally occurring, or a genetically encoded, amino acid residue.

11. The immunogenic composition of claim 9, wherein said amino acid residue other than an arginine residue or a lysine residue amino is selected from the group consisting of amino acid residue with a polar but uncharged side chain, amino acid residue with a hydrophobic side chain, and glycine residue.

12. The immunogenic composition of claim 11, wherein said amino acid residue with a polar but uncharged side chain is selected from the group consisting of serine residue, threonine residue, tyrosine residue, asparagine residue, and glutamine residue, and/or wherein said amino acid residue with a hydrophobic side chain is selected from the group consisting of alanine residue, valine residue, leucine residue, isoleucine residue, phenylalanine residue, and tryptophan residue.

13. The immunogenic composition of claim 9, wherein said amino acid residue other than an arginine residue or a lysine residue is selected from the group consisting of serine residue and threonine residue.

14. The immunogenic composition of claim 1, wherein the at least one mutation in the BC loop is a substitution of an arginine residue or a lysine residue at amino acid position 63 by an amino acid residue other than an arginine residue or a lysine residue and/or wherein the modified PCV2 ORF2 that does not contain such mutation has the arginine residue or the lysine residue at amino acid position 63, and wherein the numbering of the amino acid position refers to the amino acid sequence of wild type PCV2 ORF2 protein.

15. The immunogenic composition of claim 1, wherein said polypeptide is a recombinant PCV2 ORF2 protein, or a recombinant baculovirus expressed PCV2 ORF2 protein.

16. The immunogenic composition of claim 1, wherein said polypeptide is a PCV2 subtype b (PCV2b) ORF2 protein.

17. The immunogenic composition of claim 1, wherein said polypeptide is a PCV2 ORF2 protein comprising an amino acid sequence having at least 90% sequence identity with the amino acid sequence of SEQ ID NO: 1.

18. The immunogenic composition of claim 1, wherein said polypeptide is selected from the group consisting of the sequences set forth in SEQ ID NOs:6-9;
and/or wherein said polypeptide comprises a sequence selected from the group consisting of SEQ ID NOs: 10-45.

19. The immunogenic composition of claim 1, wherein said wild type PCV2 ORF2 protein is the protein set forth in SEQ ID NO:2.

20. The immunogenic composition of claim 1, wherein said PCV2a ORF2 polypeptide is at least 94% or at least 95% identical to the sequence of SEQ ID NO:3.

21. A polynucleotide comprising a sequence which encodes the immunogenic composition of claim 1.

22. A plasmid, or an expression vector, which comprises a polynucleotide comprising a sequence which encodes the immunogenic composition of claim 1.

23. A cell comprising a plasmid, or an expression vector, which comprises a polynucleotide comprising a sequence which encodes the immunogenic composition of claim 1.

24. A virus like particle composed of a plurality of the immunogenic composition of claim 1.

25. A baculovirus containing a polynucleotide comprising a sequence which encodes the immunogenic composition of claim 1.

26. A cell, or an insect cell, comprising a baculovirus which contains a polynucleotide comprising a sequence which encodes the immunogenic composition of claim 1.

27. A method for the treatment or prevention of an infection with PCV2, the reduction, prevention or treatment of clinical signs caused by an infection with PCV2, and/or the prevention or treatment of a disease caused by an infection with PCV2 comprising administering the immunogenic composition of claim 20 to an animal in need thereof.

28. The method of claim 27, wherein said infection with PCV2 is an infection with PCV2 subtype b (PCV2b) and/or with PCV2 of a subtype other than subtype 2b.

29. The method of claim 28, wherein said infection with PCV2b is an infection with a PCV2 comprising a polypeptide that is at least 94% or at least 95% identical to the sequence of SEQ ID NO:2 or comprising a polynucleotide which comprises a sequence encoding a polypeptide that is at least 94% or at least 95% identical to the sequence of SEQ ID NO:2.

30. The method of claim 27, wherein said infection with PCV2 is an infection with PCV2 of a subtype other than subtype 2b.

31. The method of claim 30, wherein the treatment or prevention of an infection with PCV2 of a subtype other than 2b comprises the induction of an immune response against said PCV2 of a subtype other than 2b or the concurrent induction of an immune response against said PCV2 of a subtype other than 2b and PCV2b.

32. The method of claim 27, wherein said infection with PCV2 is a concurrent infection with (i) PCV2b and (ii) PCV2 of a subtype other than subtype 2b.

33. The method of claim 27, wherein said infection with PCV2 of a subtype other than subtype 2b is an infection with PCV2 subtype a (PCV2a) and/or PCV2 subtype c (PCV2c).

34. The method of claim 33, wherein said infection with PCV2a is an infection with a PCV2 comprising a polypeptide that is at least 94% or at least 95% identical to the sequence of SEQ ID NO:3 or comprising a polynucleotide which comprises a sequence encoding a polypeptide that is at least 94% or at least 95% identical to the sequence of SEQ ID NO:3.

35. The method of claim 27, wherein the infection with PCV2 of a subtype other than subtype 2b is an infection with PCV2a.

36. The method of claim 27, wherein said infection with PCV2 is a concurrent infection with (i) PCV2b and (ii) PCV2a.

37. The method of claim 27, wherein the clinical signs of an infection with PCV2 are selected from the group consisting of lymphoid depletion, lymphoid inflammation, positive IHC for PCV2 antigen of lymphoid tissue, viremia, nasal shedding, pyrexia, reduced average daily weight gain, lung inflammation, positive IHC for PCV2 antigen of lung tissue, or said disease is PMWS.

38. A method for the treatment or prevention of an infection with PCV2, the reduction, prevention or treatment of clinical signs caused by an infection with PCV2, and/or the prevention or treatment of a disease caused by an infection with PCV2, comprising administering the immunogenic composition of claim 20 to an animal, wherein said infection with PCV2 is an infection with PCV2 subtype b (PCV2b) and/or with PCV2 of a subtype other than subtype 2b.

39. A method for the treatment or prevention of an infection with PCV2, the reduction, prevention or treatment of clinical signs caused by an infection with PCV2 or for the treatment or prevention of a disease caused by an infection with PCV2, comprising administering the immunogenic composition of claim 1 to an animal, wherein said infection with PCV2 is an infection with PCV2 subtype b (PCV2b) and/or with PCV2 of a subtype other than subtype 2b.

40. The method of claim 39, wherein the said clinical signs are selected from the group consisting of lymphoid depletion, lymphoid inflammation, positive IHC for PCV2 antigen of lymphoid tissue, viremia, nasal shedding, pyrexia, reduced average daily weight gain, lung inflammation positive IHC for PCV2 antigen of lung tissue, or said disease is PMWS.

41. The method of claim 39, wherein said immunogenic composition is administered only once.

42. A method of producing the immunogenic composition polypeptide of claim 1, comprising transfecting a cell with the plasmid, or an expression vector, wherein said expression vector comprises a polynucleotide encoding said immunogenic composition.

43. A method of producing the immunogenic composition claim 1, comprising infecting a cell, or an insect cell, with the baculovirus containing a polynucleotide encoding said immunogenic composition.

* * * * *